US010662474B2

(12) United States Patent
Rava

(10) Patent No.: US 10,662,474 B2
(45) Date of Patent: May 26, 2020

(54) IDENTIFICATION OF POLYMORPHIC SEQUENCES IN MIXTURES OF GENOMIC DNA BY WHOLE GENOME SEQUENCING

(75) Inventor: Richard P. Rava, Redwood City, CA (US)

(73) Assignee: VERINATA HEALTH, INC., San Diego, CA (US)

( * ) Notice: Subject to any disclaimer, the term of this patent is extended or adjusted under 35 U.S.C. 154(b) by 0 days.

(21) Appl. No.: 13/009,718

(22) Filed: Jan. 19, 2011

(65) Prior Publication Data

US 2011/0230358 A1 Sep. 22, 2011

Related U.S. Application Data

(63) Continuation-in-part of application No. 12/958,347, filed on Dec. 1, 2010, now abandoned.

(60) Provisional application No. 61/296,358, filed on Jan. 19, 2010, provisional application No. 61/360,837, filed on Jul. 1, 2010.

(51) Int. Cl.
*C12Q 1/6827* (2018.01)
*C12Q 1/6883* (2018.01)
*C12Q 1/6809* (2018.01)
*C12Q 1/6869* (2018.01)
*C12Q 1/6886* (2018.01)

(52) U.S. Cl.
CPC ......... *C12Q 1/6883* (2013.01); *C12Q 1/6827* (2013.01); *C12Q 1/6886* (2013.01); *C12Q 2600/16* (2013.01); *C12Q 2600/172* (2013.01)

(58) Field of Classification Search
None
See application file for complete search history.

(56) References Cited

U.S. PATENT DOCUMENTS

| | | |
|---|---|---|
| 5,432,054 A | 7/1995 | Saunders et al. |
| 5,994,057 A | 11/1999 | Mansfield |
| 6,258,540 B1 | 7/2001 | Lo et al. |
| 6,440,705 B1 | 8/2002 | Stanton et al. |
| 6,440,706 B1 | 8/2002 | Vogelstein |
| 6,555,315 B1 | 4/2003 | Short |
| 6,960,437 B2 | 11/2005 | Enzelberger et al. |
| 7,252,946 B2 | 8/2007 | Szasz |
| 7,332,277 B2 | 2/2008 | Dhallan |
| 7,645,576 B2 | 1/2010 | Lo et al. |
| 7,888,017 B2 | 2/2011 | Quake et al. |
| 8,008,018 B2 | 8/2011 | Quake et al. |
| 8,137,912 B2 | 3/2012 | Kapur et al. |
| 8,195,415 B2 | 6/2012 | Fan et al. |
| 8,318,430 B2 | 11/2012 | Chuu et al. |
| 8,532,936 B2 | 9/2013 | Rava |
| 2002/0142324 A1 | 10/2002 | Wang et al. |
| 2003/0022207 A1 | 1/2003 | Balasubramanian et al. |
| 2003/0044388 A1 | 3/2003 | Dennis et al. |
| 2003/0064368 A1 | 4/2003 | Sakai et al. |
| 2003/0194704 A1 | 10/2003 | Penn et al. |
| 2004/0137470 A1 | 7/2004 | Dhallan |
| 2004/0209299 A1 | 10/2004 | Pinter et al. |
| 2005/0164241 A1 | 7/2005 | Hahn et al. |
| 2005/0221341 A1 | 10/2005 | Shimkets et al. |
| 2005/0252773 A1 | 11/2005 | McBride et al. |
| 2006/0046258 A1 | 3/2006 | Lapidus et al. |
| 2006/0121452 A1 | 6/2006 | Dhallan |
| 2006/0134599 A1 | 6/2006 | Toner et al. |
| 2006/0257895 A1 | 11/2006 | Pinkel et al. |
| 2006/0286558 A1 | 12/2006 | Novoradovskaya et al. |
| 2007/0134658 A1 | 6/2007 | Bohmer et al. |
| 2007/0207466 A1 | 9/2007 | Cantor et al. |
| 2008/0020390 A1 | 1/2008 | Mitchell et al. |
| 2008/0050739 A1 | 2/2008 | Stoughton et al. |
| 2008/0064098 A1 | 3/2008 | Allickson |
| 2008/0070792 A1 | 3/2008 | Stoughton et al. |
| 2008/0138809 A1 | 6/2008 | Kapur et al. |
| 2008/0193927 A1 | 8/2008 | Mann et al. |
| 2008/0220422 A1 | 9/2008 | Shoemaker |
| 2008/0299562 A1 | 12/2008 | Oeth et al. |
| 2009/0026082 A1 | 1/2009 | Rothberg et al. |
| 2009/0029377 A1 | 1/2009 | Lo et al. |
| 2009/0087847 A1 | 4/2009 | Lo et al. |
| 2009/0098547 A1 | 4/2009 | Ghosh |
| 2009/0117542 A1 | 5/2009 | Maybruck et al. |
| 2009/0215042 A1 | 8/2009 | Sella-Tavor et al. |
| 2009/0270601 A1 | 10/2009 | Benner et al. |
| 2009/0291433 A1 | 11/2009 | Pollack et al. |
| 2009/0291443 A1 | 11/2009 | Stoughton et al. |
| 2009/0299645 A1 | 12/2009 | Colby et al. |

(Continued)

FOREIGN PATENT DOCUMENTS

| CA | 2693081 | 7/2008 |
|---|---|---|
| EP | 2334812 A2 | 6/2011 |

(Continued)

OTHER PUBLICATIONS

Shendure et al. Next-generation DNA sequencing. Nat Biotechnol. Oct. 2008;26(10):1135-45.*
Bentley, et al. Accurate whole human genome sequencing using reversible terminator chemistry. Nature. Nov. 6, 2008;456(7218):53-9.
Chiu, et al. Noninvasive prenatal diagnosis of fetal chromosomal aneuploidy by massively parallel genomic sequencing of DNA in maternal plasma. Proc Natl Acad Sci U S A. Dec. 23, 2008;105(51):20458-63.
Chu, et al. Statistical model for whole genome sequencing and its application to minimally invasive diagnosis of fetal genetic disease. Bioinformatics. May 15, 2009;25(10):1244-50.

(Continued)

*Primary Examiner* — Channing S Mahatan
(74) *Attorney, Agent, or Firm* — Illumina, Inc; Brent C. Moore

(57) ABSTRACT

The present invention relates to methods comprising whole genome sequencing for identifying polymorphisms in samples comprising mixtures of genomes, and for determining and/or monitoring the presence or absence of disorders associated with the identified polymorphisms.

10 Claims, 6 Drawing Sheets

Specification includes a Sequence Listing.

(56) References Cited

U.S. PATENT DOCUMENTS

| | | |
|---|---|---|
| 2009/0307181 A1 | 12/2009 | Colby et al. |
| 2009/0317817 A1 | 12/2009 | Oeth et al. |
| 2009/0317818 A1 | 12/2009 | Ehrich et al. |
| 2010/0068711 A1 | 3/2010 | Umansky et al. |
| 2010/0093835 A1 | 4/2010 | McSwiggen et al. |
| 2010/0112575 A1 | 5/2010 | Fan et al. |
| 2010/0112590 A1 | 5/2010 | Lo et al. |
| 2010/0138165 A1 | 6/2010 | Fan et al. |
| 2010/0167954 A1 | 7/2010 | Earnshaw et al. |
| 2010/0184043 A1 | 7/2010 | Mitchell et al. |
| 2010/0184075 A1 | 7/2010 | Cantor et al. |
| 2010/0216151 A1 | 8/2010 | Lapidus et al. |
| 2010/0216153 A1 | 8/2010 | Lapidus et al. |
| 2010/0285537 A1 | 11/2010 | Zimmerman |
| 2011/0105353 A1 | 5/2011 | Lo et al. |
| 2011/0118145 A1 | 5/2011 | Akmaev et al. |
| 2011/0177517 A1 | 7/2011 | Rava et al. |
| 2011/0201507 A1 | 8/2011 | Rava et al. |
| 2011/0224087 A1 | 9/2011 | Quake et al. |
| 2011/0230358 A1 | 9/2011 | Rava |
| 2011/0245085 A1 | 10/2011 | Rava et al. |
| 2011/0312503 A1 | 12/2011 | Chuu et al. |
| 2011/0319272 A1 | 12/2011 | Fan |
| 2012/0010085 A1 | 1/2012 | Rava et al. |
| 2012/0034603 A1 | 2/2012 | Oliphant et al. |
| 2012/0034685 A1 | 2/2012 | Sparks et al. |
| 2012/0040859 A1 | 2/2012 | Sparks et al. |
| 2012/0094849 A1 | 4/2012 | Rava et al. |
| 2012/0100548 A1 | 4/2012 | Rava et al. |
| 2012/0149582 A1 | 6/2012 | Rava et al. |
| 2012/0149583 A1 | 6/2012 | Rava et al. |
| 2012/0184449 A1 | 7/2012 | Hixon et al. |
| 2012/0214678 A1 | 8/2012 | Rava et al. |
| 2012/0214680 A1 | 8/2012 | Oeth et al. |
| 2012/0237928 A1 | 9/2012 | Rava et al. |
| 2012/0238738 A1 | 9/2012 | Hendrickson |
| 2013/0029852 A1 | 1/2013 | Rava et al. |
| 2013/0034546 A1 | 2/2013 | Rava et al. |
| 2013/0096011 A1 | 4/2013 | Rava et al. |
| 2013/0103320 A1 | 4/2013 | Dzakula et al. |
| 2014/0038830 A1 | 2/2014 | Srinivasan et al. |
| 2014/0199691 A1 | 7/2014 | Chuu et al. |

FOREIGN PATENT DOCUMENTS

| | | |
|---|---|---|
| EP | 2496717 | 9/2012 |
| EP | 1981995 | 7/2013 |
| GB | 2479471 A | 10/2011 |
| GB | 2479476 A | 10/2011 |
| GB | 2479080 B | 1/2012 |
| GB | 2485635 | 11/2012 |
| WO | WO 1996/19586 | 6/1996 |
| WO | WO 1998/14275 | 4/1998 |
| WO | 199839474 A1 | 9/1998 |
| WO | WO 98/44151 A1 | 10/1998 |
| WO | WO 1998/44151 | 10/1998 |
| WO | WO 00/18957 A1 | 4/2000 |
| WO | WO 2000/18957 | 4/2000 |
| WO | WO 2003/004677 | 1/2003 |
| WO | 2005/010145 | 2/2005 |
| WO | WO 2006/010610 | 2/2006 |
| WO | WO 2006/028152 | 3/2006 |
| WO | WO 2006/028153 | 3/2006 |
| WO | 2007/092473 | 8/2007 |
| WO | 2007100911 | 9/2007 |
| WO | WO 2007/100911 | 9/2007 |
| WO | 2007/147073 | 12/2007 |
| WO | 2007/147074 | 12/2007 |
| WO | 2007147074 | 12/2007 |
| WO | 2007147079 | 12/2007 |
| WO | WO 2009/013492 | 1/2009 |
| WO | WO 2009/013496 | 1/2009 |
| WO | 2009/046445 | 9/2009 |
| WO | WO 2010/033578 | 3/2010 |
| WO | 2009114543 | 4/2010 |
| WO | WO 2011/051283 A1 | 5/2011 |
| WO | 2011/090556 | 7/2011 |
| WO | 2011/090557 | 7/2011 |
| WO | 2011/090558 | 7/2011 |
| WO | WO 2012/019187 | 2/2012 |
| WO | WO 2012/019193 | 2/2012 |
| WO | WO 2012/019198 | 2/2012 |
| WO | WO 2012/019200 | 2/2012 |
| WO | 2012/071621 | 6/2012 |
| WO | 2012/078792 | 6/2012 |
| WO | 2012/088348 | 6/2012 |
| WO | 2012/103031 | 8/2012 |
| WO | 2012/108920 | 8/2012 |

OTHER PUBLICATIONS

Dhallan, et al. A non-invasive test for prenatal diagnosis based on fetal DNA present in maternal blood: a preliminary study. Lancet. Feb. 10, 2007;369(9560):474-81.

Fan, et al. Microfluidic digital PCR enables rapid prenatal diagnosis of fetal aneuploidy. Am J Obstet Gynecol. May 2009;200(5):543.e1-7.

Harris, et al. Single-molecule DNA sequencing of a viral genome. Science. Apr. 4, 2008;320(5872):106-9.

International search report and written opinion dated Feb. 28, 2011 for PCT Application No. US10/58606.

International search report and written opinion dated Mar. 1, 2011 for PCT Application No. US10/58614.

International search report and written opinion dated Apr. 4, 2011 for PCT Application No. US10/58609.

International search report and written opinion dated Apr. 11, 2011 for PCT Application No. US11/21729.

Jorgez, et al. Improving enrichment of circulating fetal DNA for genetic testing: size fractionation followed by whole gene amplification. Fetal Diagn Ther. 2009;25(3):314-9.

Leon, et al. Free DNA in the serum of cancer patients and the effect of therapy. Cancer Res. Mar. 1977;37(3):646-50.

Lo, Y. M. Noninvasive prenatal detection of fetal chromosomal aneuploidies by maternal plasma nucleic acid analysis: a review of the current state of the art. BJOG, 2009, vol. 116, 152-157.

Lun, et al. Microfluidics Digital PCR Reveals a Higher than Expected Fraction of Fetal DNA in Maternal Plasma. Clinical Chemistry, 2008, vol. 54, No. 10, 1664-1672.

McKernan, et al. Sequence and structural variation in a human genome uncovered by short-read, massively parallel ligation sequencing using two-base encoding. Genome Res. Sep. 2009;19(9):1527-41.

Nakamoto, et al. Detection of microsatellite alterations in plasma DNA of malignant mucosal melanoma using whole genome amplification. Bull Tokyo Dent Coll. May 2008;49(2):77-87.

Nicklas, et al. A real-time multiplex SNP melting assay to discriminate individuals. J Forensic Sci. Nov. 2008;53(6):1316-24.

Wright, et al. The use of cell-free fetal nucleic acids in maternal blood for non-invasive prenatal diagnosis. Hum Reprod Update. Jan.-Feb. 2009;15(1):139-51.

International search report dated May 19, 2011 for PCT/US2010/058612.

Ju, et al. Four-color DNA sequencing by synthesis using cleavable fluorescent nucleotide reversible terminators. Proc Natl Acad Sci USA. 2006; 103(52):19635-19640.

U.S. Appl. No. 61/371,605, filed Aug. 6, 2010, Oliphant et al.
U.S. Appl. No. 13/087,842, filed Apr. 15, 2011, Rava.
U.S. Appl. No. 13/191,366, filed Jul. 26, 2011, Rava et al.
U.S. Appl. No. 13/333,832, filed Dec. 21, 2011, Rava et al.
U.S. Appl. No. 13/364,809, filed Feb. 2, 2012, Rava et al.
U.S. Appl. No. 13/365,134, filed Feb. 2, 2012, Rava et al.
U.S. Appl. No. 13/365,240, filed Feb. 2, 2012, Quake et al.
U.S. Appl. No. 13/400,028, filed Feb. 17, 2012, Rava et al.
U.S. Appl. No. 13/433,232, filed Mar. 28, 2012, Stoughton et al.
European Search Report dated Feb. 22, 2012 in EP Patent Application 10825822.9.
European Search Report dated Feb. 22, 2012 in EP Patent Application 10830939.4.

(56) References Cited

OTHER PUBLICATIONS

European Search Report dated Feb. 22, 2012 in EP Patent Application 10830938.6.
Examination Report dated Jun. 24, 2011 in U.K. Patent Application No. 1106394.8.
Examination Report dated Jul. 15, 2011 in U.K. Patent Application No. 1107268.3.
Examination Report dated Jul. 15, 2011 in U.K. Patent Application No. 1108795.4.
Examination Report dated Jul. 15, 2011 in U.K. Patent Application No. 1108794.7.
Examination Report dated Nov. 15, 2011 in U.K. Patent Application No. 1107268.3.
Examination Report dated Dec. 07, 2011 in U.K. Patent Application No. 1114713.9.
Examination Report dated Dec. 16, 2011 in U.K. Patent Application No. 1108795.4.
Examination Report dated Mar. 16, 2012 in EP Patent Application No. 10830939.4.
Examination Report dated Mar. 16, 2012 in EP Patent Application No. 10830938.6.
Examination Report dated Mar. 19, 2012 in EP Patent Application No. 10825822.9.
Lazinski & Camilli, Modified protocol for Illumina paired-end library construction. Available online at http://genomics.med.tufts.edu/documents/htseq_protocol_for_illumina_paired.pdf on Feb. 27, 2009.
Lo, Y.M., Noninvasive prenatal detection of fetal chromosomal aneuploidies by maternal plasma nucleic acid analysis. Clin Chem. Jan. 2008; 54(3):461-466.
Notice of Allowance dated Mar. 1, 2012 in U.S. Appl. No. 12/696,509, with allowed claims.
Office Action dated Mar. 13, 2012 in U.S. Appl. No. 13/368,035.
Sehnert et al., Optimal Detection of Fetal Chromosomal Abnormalities by Massively Parallel DNA Sequencing of Cell-Free Fetal DNA from Maternal Blood. Clinical Chemistry, Jul. 2011, vol. 57 No. 7:1042-1049. E-pub on Apr. 25, 2011 as doi:10.1373/clinchem.2011.165910.
Vogelstein & Kinzler, Digital PCR. Proc Natl Acad Sci Aug. 1999; 96:9236-9241.
Zimmerman & Pheiffer, Macromolecular crowding allows blunt-end ligation by DNA ligase from rat liver or Escheridia coli. Proc Natl Acas Sci USA. Oct. 1983; 80(19)5852-6.
U.S. Appl. No. 12/958,347, filed Dec. 1, 2010, Rava et al.
U.S. Appl. No. 12/958,352, filed Dec. 1, 2010, Rava et al.
U.S. Appl. No. 12/958,353, filed Dec. 1, 2010, Rava et al.
U.S. Appl. No. 12/958,356, filed Dec. 1, 2010, Quake et al.
U.S. Appl. No. 13/012,222, filed Jan. 24, 2011, Chuu et al.
Botezatu, et al. Genetic analysis of DNA excreted in urine: a new approach for detecting specific genomic DNA sequences from cells dying in an organism. Clin Chem. Aug. 2000;46(8 Pt 1):1078-84.
Butler, et al. The development of reduced size STR amplicons as tools for analysis of degraded DNA. J Forensic Sci. Sep. 2003;48(5):1054-64.
Butler. Short tandem repeat typing technologies used in human identity testing. Biotechniques. Oct. 2007;43(4):ii-v.
Chan, et al. Size distributions of maternal and fetal DNA in maternal plasma. Clin Chem. Jan. 2004;50(1):88-92.
Chen, et al. Microsatellite alterations in plasma DNA of small cell lung cancer patients. Nat Med. Sep. 1996;2(9):1033-5.
Chiu, et al. Maternal plasma DNA analysis with massively parallel sequencing by ligation for noninvasive prenatal diagnosis of trisomy 21. Clin Chem. Mar. 2010;56(3):459-63.
Chiu, et al. Non-invasive prenatal assessment of trisomy 21 by multiplexed maternal plasma DNA sequencing: large scale validity study. BMJ. Jan. 11, 2011;342:e7401.
Chiu, et al. Non-invasive prenatal diagnosis by single Molecule counting technologies. Trends Genet. Jul. 2009;25(7):324-31.
Coble, et al. Characterization of new miniSTR loci to aid analysis of degraded DNA. J Forensic Sci. Jan. 2005;50(1):43-53.
Dixon, et al. Analysis of artificially degraded DNA using STRs and SNPs—results of a collaborative European (EDNAP) exercise. Forensic Sci Int. Dec. 1, 2006;164(1):33-44.
Ehrich, et al. Noninvasive detection of fetal trisomy 21 by sequencing of DNA in maternal blood: a study in a clinical setting. Am J Obstet Gynecol. Mar. 2011;204(3):205.e1-11.
Fan, et al. Analysis of the size distributions of fetal and maternal cell-free DNA by paired-end sequencing. Clin Chem. Aug. 2010;56(8):1279-86.
Fan, et al. Detection of aneuploidy with digital polymerase chain reaction. Anal Chem. Oct. 1, 2007;79(19):7576-9.
Fan, et al. In principle method for noninvasive determination of the fetal genome. Nature Precedings: Nature Precedings 10.1038/npre.2010.5373.1 . 2010.
Fan, et al. Noninvasive diagnosis of fetal aneuploidy by shotgun sequencing DNA from maternal blood. Proc Natl Acad Sci U S A. Oct. 21, 2008;105(42):16266-71.
Fan, et al. Sensitivity of noninvasive prenatal detection of fetal aneuploidy from maternal plasma using shotgun sequencing is limited only by counting statistics. PLoS One. May 3, 2010;5(5):e10439.
Fan, et al. Whole Genome Molecular Haplotyping of Single Cells. Nat Biotechnol. Jan. 2011;29(1):51-7.
Ghanta, et al. Non-invasive prenatal detection of trisomy 21 using tandem single nucleotide polymorphisms. PLoS One. Oct. 8, 2010;5(10):e13184.
Grubweiser, et al. A new miniSTR-mulitplex displaying reduced amplicon lengths for the analysis of degraded DNA. Int J Legal Med. Mar. 2006;120(2):115-20.
Hanson, et al. Whole genome amplification strategy for forensic genetic analysis using single or few cell equivalents of genomic DNA. Anal Biochem. Nov. 15, 2005;346(2):246-57.
Harrison, et al. Polymer-stimulated ligation: enhanced ligation of oligo- and polynucleotides by T4 RNA ligase in polymer solutios. Nucleic Acids Res. Nov. 12, 1984;12(21):8235-51.
Hayashi, et al. Regulation of inter- and intramolecular ligation with T4 DNA ligase in the presence of polyethylene glycol. Nucleic Acids Res. Oct. 10, 1986;14(19):7617-31.
Hill, et al. "Characterization of 26 new miniSTR loci" Poster #44—17th International Symposium on Human Identification, Nashville, TN, Oct. 10-12, 2006.
Huang, et al. Isolation of cell-free DNA from maternal plasma using manual and automated systems. Methods Mol Biol. 2008;444:203-8.
Hung, et al. Detection of circulating fetal nucleic acids: a review of methods and applications. J Clin Pathol. Apr. 2009;62(4):308-13.
Illumina. Preparing samples for CHIP sequencing of DNA. Epub at grcf.jhmi.edu/hts/protocols/11257047_ChIP_Sample_Prep.pdf. 2007.
International. The International HapMap Project. Nature. 2003; 426:789-96.
Jama, et al. Quantification of Cell-Free Fetal DNA Levels in Maternal Plasma by STR Analysis. ACMG Annual Clinical Genetics Meeting Poster 398; Mar. 24-28, 2010. Available online at http://acmg.omnibooksonline.com/2010/data/papers/398.pdf and http://acmg.omnibooksonline.com/2010/index.html.
Kidd, et al. Developing a SNP panel for forensic identification of individuals. Forensic Sci Int. Dec. 1, 2006;164(1):20-32.
Koide, et al. Fragmentation of cell-free fetal DNA in plasma and urine of pregnant women. Prenat Diagn. Jul. 2005;25(7):604-7.
Kozarewa, et al. Amplification-free Illumina sequencing-library preparation facilitates improved mapping and assembly of GC-biased genomes. Nat Methods. Apr. 2009;6(4):291-5.
Lazinski, et al. Modified protocol for Illumina paired-end library construction. Available online at http://genomics.med.tufts.edu/docurnents/htseq_protocol_for_illumina_paired.pdf Accessed Jun. 21, 2011.
Levy, et al. The Diploid Genome Sequence of an Individual Human. PLoS Biol. Sep. 4, 2007;5(10):e254.
Li, et al. Size separation of circulatory DNA in maternal plasma permits ready detection of fetal DNA polymorphisms. Clin Chem. Jun. 2004;50(6):1002-11.
Liao, et al. Targeted massively parallel sequencing of maternal plasma DNA permits efficient and unbiased detection of fetal alleles. Clin Chem. Jan. 2011;57(1):92-101.

(56) References Cited

OTHER PUBLICATIONS

Liu, et al. Feasibility study of using fetal DNA in maternal plasma for non-invasive prenatal diagnosis. Acta Obstet Gynecol Scand. 2007;86(5):535-41.
Lo, et al. Digital PCR for the molecular detection of fetal chromosomal aneuploidy. Proc Natl Acad Sci U S A. Aug. 7, 2007;104(32):13116-21.
Lo, et al. Increased fetal DNA concentrations in the plasma of pregnant women carrying fetuses with trisomy 21. Clin Chem. Oct. 1999;45(10):1747-51.
Lo, et al. Maternal plasma DNA sequencing reveals the genome-wide genetic and mutational profile of the fetus. Sci Transl Med. Dec. 8, 2010;2(61):61ra91.
Lo, et al. Presence of fetal DNA in maternal plasma .Lancet. Aug. 16, 1997;350(9076):485-7.
Lo, et al. Quantitative analysis of fetal DNA in maternal plasma and serum: implications for noninvasive prenatal diagnosis. Am J Hum Genet. Apr. 1998;62(4):768-75.
Lo, et al. Rapid clearance of fetal DNA from maternal plasma. Am J Hum Genet. Jan. 1999;64(1):218-24.
Metzker. Sequencing technologies—the next generation. Nat Rev Genet. Jan. 2010;11(I):31-46.
Pakstis, et al. Candidate SNPs for a universal individual identification panel. Hum Genet. May 2007;121(3-4):305-17.
Pakstis, et al. SNPs for a universal individual identification panel. Hum Genet. Mar. 2010;127(3):315-24.
Pathak, et al. Circulating cell-free DNA in plasma/serum of lung cancer patients as a potential screening and prognostic tool. Clin Chem. Oct. 2006;52(10):1833-42.
Pertl, et al. Detection of male and female DNA in maternal plasma by multiplex fluorescent polymerase chain reaction amplification of short tandem repeats. Hum Genet. Jan. 2000;106(1):45-9.
Pheiffer, et al. Polymer-stimulated liagtion: enhanced blunt- or cohesive-end liagtion of DNA or deoxyribooligonucleotides by T4 DNA ligase in polymer solutions. Nucleic Acids Res. Nov. 25, 1983;11(22):7853-71.
Pushkarev, et al. Single-molecule sequencing of an individual human genome. Nat Biotechnol. Sep. 2009;27(9):847-50.
Quail, et al. A large genome center's improvements to the Illumina sequencing system. Nat Methods. Dec. 2008;5(12):1005-10.
Schwartzenbach, et al. Cell-free tumor DNA in blood plasma as a marker for circulating tumor cells in prostate cancer. Clin Cancer Res. Feb. 1, 2009;15(3):1032-8.
Schwartzenbach, et al. Comparative evaluation of cell-free tumor DNA in blood and disseminated tumor cells in bone marrow of patients with primary breast cancer. Breast Cancer Res. 2009;11(5):R71.
Su, et al. Human urine contains small, 150 to 250 nucleotide-sized, soluble DNA derived from the circulation and may be useful in the detection of colorectal cancer. J Mol Diagn. May 2004;6(2):101-7.
Tong, et al. Noninvasive prenatal detection of trisomy 21 by an epigenetic-genetic chromosome-dosage approach. Clin Chem. Jan. 2010;56(1):90-8.
Vallone, et al. Demonstration of rapid multiplex PCR amplification involving 16 genetic loci. Forensic Sci Int Genet. Dec. 2008;3(1):42-5.
Voelkerding, et al. Digital Fetal Aneuploidy Diagnosis by Next-Generation Sequencing. Clin Chem. Mar. 2010;56(3):336-8.
Voelkerding, et al. Next-generation sequencing: from basic research to diagnostics Clin Chem. Apr. 2009;55(4):641-58.
Wheeler, et al. The complete genome of an individual by massively parallel DNA sequencing. Nature. Apr. 17, 2008;452(7189):872-6.
Zimmerman, et al. Macromolecular crowding allows blunt-end ligation by DNA ligase from rat liver or *Escheridia coli*. Proc Natl Acad Sci U S A. Oct. 1983;80(19):5852-6.
Bentley, et al., "Accurate whole human genome sequencing using reversible terminator chemistry", Nature, vol. 456, No. 7218, Nov. 6, 2008, 53-59.
Beroukhim, et al., "The landscape of somatic copy-number alteration across human cancers", Nature, vol. 463, Feb. 2010, 899-905.

Borsting, , "Multiplex PCR, amplicon size and hybridization efficiency on the NanoChip electronic microarray", Int J. Legal Med. vol. 118, 2004, 75.
Botezatu, et al., "Genetic Analysis of DNA excreted in urine: a new approach for detecting specific genomic DNA sequences from cells dying in an organism", Clin Chem. 46(8 Pt1), Aug. 2000, 1078-84.
Buck, et al., "Design Strategies and Performance of Custom DNA Sequencing Primers", Biotechniques vol. 27, 1999, 528-536.
Butler, et al., "Short tandem repeat typing technologies used in human identity testing", Biotechniques 43(4), Sep. 2003, ii-v.
Butler, et al., "The Development of reduced size STR amplicons as tools for analysis of degraded DNA", J. Forensic Sci 48(5), 2003, 1054-64.
Chan, et al., "Size Distributions of maternal and fetal DNA in Maternal Plasma", Clin. Chem 50(1), Jan. 2004, 88-92.
Chen, et al., "Microsatellite alterations in plasma DNA of small cell lung cancer patients", Nat Med. 2(9), 1996, 1033-5.
Chiang, et al., "High-resolution mapping of copy-number alterations with massively parallel sequencing", Nature Methods, vol. 6, No. 1 (2009), published online: doi:10.1038/nmeth.1276, Nov. 30, 2008, 99-103.
Chiu, et al., "Maternal Plasma DNA Analysis with Massively Parallel Sequencing by Ligation for Noninvasive Prenatal Diagnosis of Trisomy 21", Clinical Chemistry 56:3, 2010, 459-463.
Chiu, et al., "Non-invasive prenatal diagnosis by single molecule counting technologies", Trends Tenet. 25 (7), Jul. 2009, 324-31.
Chiu, et al., "Noninvasive prenatal diagnosis of fetal chromosomal aneuploidy by massively parallel genomic sequencing of DNA in maternal plasma", Proc Natl Acad Sci 105(51), Dec. 23, 2008, 20458-63.
Chu, et al., "Statistical model for whole genome sequencing and its application to minimally invasive of fetal genetic disease", Bioinformatics 25(10), May 15, 2009, 1244-40.
Clarke, et al., "Effects of chemotherapy and hormonal therapy for early breast cancer on recurrence and 15-year survival: an overview of randomised trials", Lancet vol. 365, 2005, 1687-1717.
Clarke, et al., "Effects of radiotherapy and of differences in the extent of surgery for early breast cancer on local recurrence and 15-year survival: an overview of the randomised trials", Lancet vol. 366, 2005, 2087-2106.
Coble, et al., "Characterization of New MiniSTR Loci to Aid Analysis of Degraded DNA", J Forensic Sci, 50(1), Jan. 2005, 43-53.
Deng, et al., "Enumeration and microfluidic chip separation of circulating fetal cells early in pregnancy from maternal blood", American journal of Obstetrics & Gynecology, vol. 199, Issue 6, Dec. 2008, S134.
Dhallan, et al., "A non-invasive test for prenatal diagnosis based on fetal DNA present in maternal blood: a preliminary study", Lancet 369(9560), Feb. 10, 2007, 474-81.
Ding, et al., "MS analysis of single-nucleotide differences in circulating nucleic acids: Application to noninvasive prenatal diagnosis", Proceedings of National Academy of Sciences 101(29), 2004, 10762-10767.
Dixon, et al., "Analysis of artificially degraded DNA using STRs and SNPs—results of a collaborative European (EDNAP) exercise", Forensic Sci Int 164(1), 2006, 33-44.
Fan, et al., "Analysis of the size distributions of fetal and maternal cell-free DNA by paired-end sequencing", Clin. Chem 56(8), Aug. 1, 2010, 1279-1286.
Fan, et al., "Detection of aneuploidy with digital polymerase chain reaction", Anal Chem. 79(19), Oct. 1, 2007, 7576-9.
Fan, et al., "In principle method for noninvasive determination of the fetal genome", Nature Precedings: Nature Precedings 10.1038/npre, 2010, 5373.1.
Fan, et al., "Microfluidic digital PCR enables rapid prenatal diagnosis of fetal aneuploidy", Am J Obstet Gynecol 200(5), May 2009, 543.e1-7.
Fan, et al., "Noninvasive diagnosis of fetal aneuploidy by shotgun sequencing DNA from maternal blood", Proc Natl Acad Sci 105(42), Oct. 21, 2008, 16266-71.

(56) References Cited

OTHER PUBLICATIONS

Fan, et al., "Sensitivity of noninvasive prenatal detection of fetal aneuploidy from maternal plasma using shotgun sequencing is limited only by counting statistics", PLoS One 5(5), May 3, 2010, e10439.

Fan, et al., "Whole-genome molecular haplotyping of single cells", Nature Biotechnology, Advanced Online Publication, Dec. 19, 2010, 9 pages.

Frohling, et al., "Chromosomal Abnormalities in Cancer", New England Journal of Medicine, vol. 359, 2008, 722-734.

Ghanta, et al., "Non-Invasive Prenatal Detection of Trisomy 21 Using Tandem Single Nucleotide Polymorphisms", PLos ONE, vol. 5, Issue 10, e13184, Oct. 2010, 10 pages.

Goossens, et al., "Simultaneous Mutation and Copy Number Variation (CNV) Detection by Multiplex PCR-Based GS-FLX Sequencing", Human Mutation, vol. 30, Issue 3, Dec. 2008, 472-476.

Grubweiser, et al., "A new "miniSTR-multiplex" displaying reduced amplicon lengths for the analysis of degrade DNA", Int J. Legal Med 120(2), 2006, 115-20.

Hanson, et al., "Whole genome amplification strategy for forensic genetic analysis using single or few cell equivalents of genomic DNA", Anal Biochem. 346(2), Nov. 15, 2005, 246-57.

Harris, et al., "Single-Molecule DNA Sequencing of a Viral Genome", Science 320, Apr. 4, 2008, 106-109 and Suppl. Materials 1-25.

Harrison, et al., "Polymer-stimulated ligation: enhanced ligation of oligo-and polynucleotides by T4 RNA ligase in polymer solutions", Nucleic Acids Research vol. 12 No. 21 1984, 1984, 8235-51.

Hayashi, et al., "Regulation of inter-and intramolecular ligation with T4 DNA ligase in the presence of polyethylene glycol", Nucleic Acids Res. 14(19), Oct. 10, 1986, 7617-31.

Hill, et al., "Characterization of 26 new miniSTR Loci", Poster #44—17th International Symposium on Human Identification, Nashville, TN, Oct. 10-12, 2006, 1.

Hoffman, et al., "The genome-enabled electronic medical record", Journal of Biomedical Informatics 10 (2007) published online, Mar. 15, 2006, 44-46.

Huang, , "Isolation of cell-free DNA from maternal plasma using manual and automated systems", Methods Mol Biol. 444, 2008, 203-8.

Hung, , "Detection of circulating fetal nucleic acids: a review of methods and applications", J Clin Pathol 62(4), 4/62/2009, 308-13.

Illumina, , "Preparing Samples for ChIP sequencing of DNA", E-pub at grcf.jhmi.edu/hts/protocols/11257047_ChIP_Sample_Prep. pdf., 2007, 15.

International, , "The International HapMap Consortium Project", Nature 426:789-96, 2003, 8.

Jama, et al., "Quantification of cell-free fetal DNA Levels on maternal plasma by STR analysis", 2010 ACMG Annual Clinical Genetics Meeting, 2010, 2.

Jorgez, et al., "Improving Enrichment of circulating fetal DNA for genetic testing: size fractionation followed by whole gene amplification", Fetal Diagn Ther 2009, 2009, 6.

Ju, et al., "Four-Color DNA Sequencing by Synthesis Using Cleavable Florescent Nucleotide Reversible Terminators", PNAS vol. 103, No. 52, 2006, 19635-19640.

Kidd, et al., "Developing a SNP panel for forensic identification of individuals", Forensic Science International 164 ( 2006), 2006, 20-32.

Kim, et al., "rSW-seq: algorithm for detection of copy number alterations in deep sequencing data", BMC Bioinformatics, vol. 11, Aug. 18, 2010, 432.

Koide, et al., "Fragmentation of cell-free fetal DNA in plasma and urine of pregnant women", www.interscience.wiley.com, Mar. 14, 2005, 4.

Kozarewa, et al., "Amplification-free Illumina sequencing-library preparation facilitates improved mapping and assembly of GC-biased genomes", UKPMC Funders Group Author Manuscript, Oct. 1, 2009, 12.

Lazinski, et al., "Modified Protocol for Illumina Paired-End Library Construction", http://genomics.med.tufts.edu/documents/htseq_protocol_for_illumina_paired.pdf, Feb. 27, 2009, 10.

Leon, et al., "Free DNA in the Serum of Cancer Patients and the Effect of Therapy", Cancer Research 37, Mar. 1, 1977, 646-650.

Levy, et al., "The Diploid Genome Sequence of an Individual Human", PLoS Biology, vol. 5, Issue 10, Oct. 2007, 2113-2144.

Li, et al., "Size separation of circulatory DNA in maternal plasma permits ready detection of fetal DNA polymorphisms", Clinical Chemistry 50:6, 2004, 1002-11.

Liu, et al., "Feasibility study of using fetal DNA in maternal plasma for non-invasive prenatal diagnosis", Acta Obstet Gynecol Scand. 86(5), 2007, 535-41.

Lo, et al., "Digital PCR for the molecular detection of fetal chromosomal aneuploidy", Proc Natl Acad Sci USA. 104(32), Aug. 7, 2007, 13116-21.

Lo, et al., "Increased fetal DNA concentrations in the plasma of pregnant women carrying fetuses with trisomy 21", Clinical Chemistry 45:10, 1999, 1747-51.

Lo, et al., "Maternal plasma DNA sequencing reveals the genome-wide genetic and mutational profile of the fetus", Sci Transl Med. 2(61):, Dec. 8, 2010, 61ra91.

Lo, et al., "Noninvasive prenatal detection of fetal chromosomal aneuploidies by maternal plasma nucleic acid analysis: a review of the current state of the art", BJOG, vol. 116, 2009, 152-157.

Lo, et al., "Noninvasive prenatal diagnosis of fetal chromosomal aneuploidies by maternal plasma nucleic acid analysis", Clin Chem. 54(3), Jan. 2008, 461-466.

Lo, et al., "Prenatal diagnosis of fetal RhD Status by molecular analysis of maternal plasma", The New England Journal of Medicine, Dec. 10, 1998, 1734-1738.

Lo, et al., "Presence of fetal DNA in maternal plasma and serum", Lancet. 350(9076), Aug. 16, 1997, 485-7.

Lo, et al., "Quantitative analysis of fetal DNA in maternal plasma and serum: implications for noninvasive prenatal diagnosis", Am J Hum Genet 62(4), Apr. 1998, 768-775.

Lo, et al., "Rapid Clearance of fetal DNA from Maternal Plasma", Am J Hum Genet. 64(1), 1999, 218-24.

Lun, et al., "Microfluidics digital PCR Reveals a Higher than expected fraction of fetal DNA in maternal plasma", Clinical Chemistry, vol. 54, No. 10, 2008, 1664-1672.

Lun, , "Noninvasive prenatal diagnosis of monogenic diseases by digital size selection and relative mutation dosage on DNA in maternal plasma", Proceedings of National Academy of Sciences 105(50), 2008, 19920-19925.

McKernan, et al., "Sequence and structural variation in a human genome uncovered by short-read, massively parallel ligation sequencing using two-base encoding", Genome Res. 19(9), Sep. 2009, 1527-41.

Metzker, , "Sequencing technologies—the next generation", Nat Rev Genet. 11(1), Jan. 2010, 31-46.

Meyerson, et al., "Advances in understanding cancer genomes through second-generation sequencing", Nature Reviews Genetics, vol. 11, 2010, 685-696.

Mullighan, et al., "Genome-wide profiling of genetic alterations in acute lymphoblastic leukemia: recent insights and future directions.", Leukemia vol. 23, Feb. 26, 2009, 1209-1218.

Nakamoto, , "Detection of Microsatellite alterations in Plasma DNA of Malignant Mucosal Melanoma Using Whole Genome Amplification", Bull Tokyo Dent Coll. May 2008; 49(2), May 2008, 77-87.

Nicklas, , "A real-time multiplex SNP melting assay to discriminate individuals", J. Forensic Sci. 53(6):, Nov. 2008, 1316-24.

Pakstis, et al., "Candidate SNPs fora universal individual identification panel", Hum Genet. 121(3-4), May 2007, 305-17.

Pakstis, et al., "Candidate SNPs for a universal individual identification panel", Hum Genet. 127(3):, Mar. 2010, 315-24.

Pandey, et al., "Chapter 3 Applied Biosystems SOLID Systems: Ligation-Based Sequencing", Next Generation Genome Sequencing: Towards Personalized Medicine 2008. Edited by Michael Janitz., 2008, 14.

Pathak, et al., "Circulating Cell-Free DNA in Plasma/Serum of Lung Cancer Patients as a Potential Screening and Prognostic Tool", Clin Chem. 52(10):, Oct. 2006, 1833-42.

(56) References Cited

OTHER PUBLICATIONS

Pertl, et al., "Detection of male and female fetal DNA in maternal plasma by multiplex fluorescent polymerase chain reaction amplification of short tandem repeats", Hum Genet. 106(1), Jan. 2000, 45-9.
Peters, D. et al., "Noninvasive Prenatal Diagnosis of a Fetal Microdeletion Syndrome", New England Journal of Medicine 365;19, Correspondence, Nov. 10, 2001, 1847-1848.
Pheiffer, et al., "Polymer-stimulated ligation: enhanced blunt- or cohesive-end ligation of DNA or deoxyribooligonucleotides by T4 DNA ligase in polymer solutions", Nucleic Acids Res.11(22), Nov. 25, 1983, 7853-71.
Pui, et al., "Acute lymphoblastic leukaemia", Lancet vol. 371, 2008, 1030-1043.
Pushkarev, et al., "Single-molecule sequencing of an individual human genome", Nat Biotechnol. 27(9):, Sep. 2009, 847-50.
Quail, et al., "A large genome centers improvements to the Illumine sequencing system", Nature Methods, 5, 2008, 1005-1010.
Schwarzenbach, et al., Cell-free Tumor DNA in Blood Plasma as a Marker for Circulating Tumor Cells in Prostate Cancer, Clin Cancer Res. 15(3):, Feb. 1, 2009, 1032-8.
Schwarzenbach, et al., Comparative evaluation of cell-free tumor DNA in blood and disseminated tumor cells in bone marrow of patients with primary breast cancer, Breast Cancer Res. 11(5), 2009, R71.
Shendure, et al., "Next-generation DNA sequencing", Nature Biotechnology 26(10), 2008, 1135-1145.
Su, et al., Human Urine Contains Small, 150 to 250 Nucleotide-Sized, Soluble DNA Derived from the Circulation and May be useful in the Detection of Colorectal Cancer, J Mol Diagn. 6(2), May 2004, 101-7.
Teixeira, et al., "Multiple numerical chromosome aberrations in cancer: what are their causes and what are their consequences?", Seminars in Cancer Biology, vol. 15, Issue 1, Feb. 2005, 3-12.
Thorstenson, et al., "An Automated Hydrodynamic Process for Controlled, Unbiased DNA Shearing", Genome Research 8, 1998, 848-855.
Tong, et al., "Noninvasive Prenatal Detection of Fetal Trisomy 18 by Epigenetic Allelic Ratio Analysis in Maternal Plasma: Theoretical and Empirical Considerations", Clinical Chemistry 52:12, 2006, 2194-2202.
Tong, et al., "Noninvasive prenatal detection of trisomy 21 by an epigenetic-genetic chromosome-dosage approach", Clin Chem. 56(1), Jan. 2010, 90-8.
Vallone, et al., "Demonstration of rapid multiplex PCR amplification involving 16 genetic loci", Forensic Sci Int Genet. 3(1), Dec. 2008, 42-5.
Voelkerding, et al., "Digital Fetal Aneuploidy diagnosis by next-generation sequencing", Clin Chem. 56(3), Mar. 2010, 336-8.
Voelkerding, et al., "Next-Generation Sequencing: From Basic Research to Diagnostics", Clinical Chemistry 55:4, 2009, 641-658.
Vogelstein, et al., "Digital PCR", PNAS USA, vol. 96, 1999, 9236-9241.
Wheeler, et al., "The complete genome of an individual by massively parallel DNA sequencing", Nature. 452(7189), Apr. 17, 2008, 872-6.
Wright, et al., "The use of cell-free fetal nucleic acids in maternal blood for non-invasive prenatal diagnosis", Hum Reprod Update. 15(1), Jan.-Feb. 2009, 139-51.
Yamazawa, et al., "Monozygotic female twins for Silver-Russell syndrome and hypomethylation of H19-DMR", J. Human Genetics, vol. 53, 2008, 950-955.
Zimmerman, et al., "Macromolecular crowding allows blunt-end ligation by DNA ligases from rat liver or *Escherichia coli*", Proc Natl Acas Sci USA. 80(19), Oct. 1983, 5852-6.
Examination Report in GB Patent Application No. 1108795.4, dated Mar. 9, 2012.

Amaral, et al., "Application of massive parallel sequencing to whole genome SNP discovery in the porcine genome", BMC Genomics, Biomed Central Ltd, London, UK, vol. 10, No. 1, Aug. 12, 2009, 374.
Angeloni, D. , "Molecular analysis of deletions in human chromosome 3p21 and the role of resident cancer genes in disease", Briefings Functional Genomics, vol. 6(1), May 24, 2007, 19-39.
Ashoor, et al., "Chromosome-selective sequencing of maternal plasma cell-free DNA for first-trimester detection of trisomy 21 and trisomy 18", Am J Obstet Gynecol, 206(4), Apr. 2012, 322.e1-5.
Ashoor, et al., "Fetal Fraction in maternal plasma cell-free DNA at 11-13 weeks' gestation: effect of maternal and fetal factors", Fetal Diagn Ther, published online, May 4, 2012, 7 pages.
Bianchi, et al., "Genome-Wide Fetal Aneuploidy Detection by Maternal Plasma DNA Sequencing", Obstetrics and Gynecology, vol. 119, No. 5, May 5, 2012, 890-901.
Bianchi, et al., "Isolation of fetal DNA from nucleated erythrocytes in maternal blood", Medical Sciences, vol. 87, 1990, 3279-3283.
Bischoff, et al., "Cell-free fetal DNA and intact fetal cells in maternal blood circulation: implications for first and second trimester non-invasive prenatal diagnosis", Human Reproduction Updated, vol. 8, No. 6, 2002, 493-500.
Bowcock, et al., "Exclusion of the Retinablastoma Gene and Chromosome 13q as the Site of a Primary Lesion for Human Breast Cancer", Am J Hum Genet, vol. 46, 1990, 12.
Braslavsky, et al., "Sequence information can be obtained from single DNA molecules", PNAS, 100(7), 2003, 3960-3964.
Brosens, et al., "Deletion of chromosome 4q predicts outcome in stage II colon cancer patients", Analytical Cellular Pathology / Cellular Oncology 33, 2010, 95-104.
Brown, et al., "Chemical synthesis and cloning of a tyrosine tRNA gene", Methods Enzmol., vol. 68, 1979, 109.
Bruch, et al., "Trophoblast-like cells sorted from peripheral maternal blood using flow cytometry: A multiparametric study involving transmission electron microscopy and fetal dna amplification", Prenatal Diagnosis, vol. 11, 1991, 787-798.
Bustina, et al., "Pitfalls of Quantitative Real-Time Reverse-Transcription Polymerase Chain Reaction", J. Biomol. Tech., vol. 15, 2004, 155-166.
Caramazza, et al., "Chromosome 1 abnormalities in myeloid malignancies: a literature survey and karyotype-phenotype associations", European Journal of Haematology, vol. 84, 2010, 191-200.
Chan, et al., "DNA Mapping Using Micro fluidic Stretch-ing and Single-Molecule Detection of Fluorescent Site-Specific Tags", Genome Research, vol. 14, 2004, 1137-1146.
Chang, et al., "Assessment of Plasma DNA Levels, Allelic Imbalance, and CA 125 as Diagnostic Tests for Cancer", Journal of the National Cancer Institute, vol. 94, No. 22, Nov. 22, 2002, 1697-1703.
Chen, et al., "Detection in Fecal DNA of Colon Cancer-Specific hylation of the Nonexpressed Vimentin Gene", Journal of the National Cancer Institute, vol. 97, No. 15,, Aug. 2, 2005, 1124-1132.
Chiu, et al., "Effects of Blood-Processing Protocols on Fetal and Total DNA Quantification in Maternal Plasma", Clinical Chemistry, vol. 47, No. 9, 2001, 1607-1613.
Chiu, et al., "Noninvasive Prenatal Diagnosis by Analysis of Fetal DNA in Maternal Plasma", Methods in Molecular Biology, 336, Clinical Applications of PCR, Second Edition, Edited by Y.M. Dennis Lo et al., Humana Press Inc., 2006, 101-109.
Dhallan, et al., "Methods to Increase the Percentage of Free Fetal DNA Recovered From the Maternal Circulation", J. Am. Med. Soc., vol. 291, No. 9, Mar. 2004, 1114-1119.
Dressman, et al., "Transforming single DNA molecules into fluorescent magnetic particles for detection and enumeration of genetic variations", PNAS, 100(15), 2003, 8817-8822.
Eisenmann, et al., "5q—myelodysplastic syndromes: chromosome 5q genes direct a tumor-suppression network sensing actin dynamics", Oncogene, vol. 28, 2009, 3429-3441.
Fan, et al., "Microfluidic digital PCR enables rapid prenatal diagnosis of fetal aneuploidy", American Journal of Obstetrics & Gynecology, May 2009, 543e1-543.-e7.

(56) References Cited

OTHER PUBLICATIONS

Fonatsch, C., "The role of chromosome 21 in hematology and oncology", Genes, Chromosomes and Cancer, vol. 49, Issue 6, Jun. 2010, 497-508.
Fuscoe, et al., "An Efficient Method for Selecting Unique-Sequence Clones from DNA Libraries and Its Application to Fluorescent Staining of Human Chromosome 21 Using in Situ Hybridization", Genomics, vol. 5, 1989, 100-109.
Gardiner, et al., "Analysis of human chromosome 21: correlation of physical and cytogenetic maps; gene and CpG island distributions", The EMBOJ Journal, vol. 9, No. 1, 1990, 25-34.
Grundevik, et al., "Molecular Diagnostics of Aneuploidies", Chalmers University of Technology, Sweden, Department of Molecular Biotechnology, May 17, 2005, 1-12.
Herzenberg, et al., "Fetal cells in the blood of pregnant women: Detection and enrichment by fluorescence-activated cell sorting", Proc. Natl. Acad. Sci. 76, 1979, 1453-1455.
Hesser, et al., "Down syndrome critical region protein 1 (DSCR1), a novel VEGF target gene that regulates expression of inflammatory markers on activated endothelial cells", Blood, vol. 104, No. 1, Jul. 1, 2004, 149-158.
Hochstenbach, et al., "Array analysis and karyotyping: workflow consequences based on a retrospective study of 36,325 patients with idiopathic developmental delay in the Netherlands", Eur. J. Med. Genet., 52(4), Jul. 1, 2009, 161-169.
Howe, et al., "Retinoblastoma growth suppressor and a 300-kDa protein appear to regulate cellular DNA synthesis", Proc. Natl. Acad. Sci. USA, vol. 87, Aug. 1990, 5883-5887.
Hromadnikova, et al., "Quantitative analysis of DNA levels in maternal plasma in normal and Down syndrome pregnancies", Bio Med Central, May 2002, 1-5.
Huber, et al., "High-resolution liquid chromatography of DNA fragments on non-porous poly(styrene-divinylbenzene) particles", Nucleic Acids Res., vol. 21, No. 5, Mar. 11, 1993, 1061-1066.
Illanes, et al., "Early detection of cell-free fetal DNA in maternal plasma", Early Human Development, vol. 83, 2007, 563-566.
Jensen, et al., "Detection of Microdeletion 22q11.2 in a Fetus by Next-Generation Sequencing of Maternal Plasma", Clinical Chemistry 58:7; doi:10.1373/clinchem.2011.180794, May 4, 2012, 1148-1151.
Jiang, et al., "FetalQuant: deducing fractional fetal DNA concentration from massively parallel sequencing of DNA in maternal plasma", Bioinformatics, vol. 28, No. 22, 2012, 2883-2890.
Jongsma, et al., "Molecular evidence for putative tumour suppressor genes on chromosome 13q specific to BRCA1 related ovarian and fallopian tube cancer", J Clin Pathol: Mol Pathol., vol. 55(5), 2002, 305-309.
Kaiser, J. , "An Earlier Look at Baby's Genes", Science, vol. 309, Sep. 2, 2005, 1476.
Kato, et al., "A New Packing for Separation of DNA Restriction Fragments by High Performance Liquid Chromatography", J. Biochem., vol. 95, No. 1, 1984, 83-86.
Langmead, et al., "Ultrafast and memory-efficient alignment of short DNA sequences to the human genome", Genome Biology, vol. 10, 2009, R25.1-R25.10.
Lee, et al., "Improving the efficiency of genomic loci capture using oligonucleotide arrays for high throughput resequencing", BMC Genomics, Biomed Central Ltd, London, UK, vol. 10, No. 646, Dec. 31, 2009, 1-12.
Li, et al., "Detection of paternally inherited fetal point mutations for beta-thalassemia using size-fractionated cell-free DNA in maternal plasma", J. Amer. Med. Assoc., vol. 293, Feb. 16, 2005, 843-849.
Li, et al., "SNP detection for massively parallel whole-genome resequencing", Genome Research, vol. 19, No. 6, Jun. 1, 2009, 1124-1132.
Lo, et al., "Fetal DNA in Maternal Plasma", Ann. NY Acad. Sci, vol. 906, Apr. 2000, 141-147.
Mann, et al., "Strategies for the rapid prenatal diagnosis of chromosome aneuploidy", European Journal of Human Genetics, vol. 12, 2004, 907-915.
Margulies, et al., "Genome sequencing in microfabricated high-density picolitre reactors", Nature, vol. 437, 2005, 376-380 and Supplemental Materials.
Narang, et al., "Improved phosphotriester method for the synthesis of gene fragments", Methods Enzmol., vol. 68, 1979, 90-98.
Ng, et al., "mRNA of placental origin is readily detectable in maternal plasma", Proc. Nat. Acad. Sci., vol. 100, No. 8, 2003, 4748-4753.
Ng, et al., "The Concentration of Circulating Corticotropin-releasing Hormone mRNA in Maternal Plasma is Increased in Preecla[mu]psia", Clin. Chem., vol. 49:5, 2003, 727-731.
Norton, et al., "Non-invasive chromosomal evaluation (NICE) study: results of multicenter, prospective, cohort study for detection of fetal trisomy 21 and trisomy 18", American Journal of Obstetrics and Gynecology, doi: 10.1016/j.ajog.2012.05.021., May 21, 2012, 30 pages.
Ottesen, et al., "Microfluidic Digital PCR Enables Multigene Analysis of Individual Environmental Bacteria", Science, vol. 314, Dec. 2006, 1464-1467.
Oudejans, et al., "Detection of Chromosome 21-encoded mRANA of Placental Origin in Maternal Plasma", Clinical Chemistry, vol. 49, 2003, 1445-1449.
Park, et al., "A single-tube protocol for next gen library construction increases complexity and simplifies parallel sample handling", Cancer Research 71(8): Suppl. 1, Abstract No. 4851, Apr. 15, 2011.
Park, et al., "Unraveling the Biologic and Clinical Complexities of HER2", Clinical Breast Cancer, vol. 8, Issue 5, Oct. 2008, 392-401.
Pennisi, E. , "Semiconductors Inspire New Sequencing Technologies", Science 327, Mar. 5, 2010, 1190.
Poon, et al., "Differential DNA Methylation between Fetus and Mother as a Strategy for Detecting Fetal DNA in Maternal Plasma", Clin. Chem., vol. 48, No. 1, 2002, 35-41.
Redon, et al., "Global Variation in copy number in the human genome", Nature 444(7118), 2006, 444-54.
Rygaard, et al., "Abnormalities in Structure and Expression of the Retinoblastoma Gene in Small Cell Lung Cancer Cell Lines and Xenografts in Nude Mice", Cancer Res., vol. 50, 1990, 5312-5317.
Sambrook, et al., "Molecular Cloning: A Laboratory Manual", 3rd Edition, Cold Spring Harbor Laboratory, New York, 2001.
Satiroglu Tufan, et al., "Analysis of cell-free fetal DNA from maternal plasma and serum using a conventional multiplex PCR: Factors influencing success", Turk J. Med Sci, No. 35, 2005, 85-92.
Sato, et al., "Allelotype of Breast Cancer: Cumulative Allele Losses Promote Tumor Progression in Primary Breast Cancer", Cancer Res., vol. 50, 1990, 7184-7189.
Shaikh, et al., "High-resolution mapping and analysis of copy number variations in the human genome: A data resource for clinical and research applications", Genome Res., vol. 19, 2009, 1682-1690.
Shendure, et al., "Accurate Multiplex Polony Sequencing of an Evolved Bacterial Genome", Science 309, Sep. 9, 2005, 1728-1732.
Soni, et al., "Progress toward Ultrafast DNA Sequencing Using Solid-State Nanopores", Clin Chem, 53(11), 2007, 1996-2001.
Sparks, et al., "Non-invasive prenatal detection and selective analysis of cell-free DNA obtained from maternal blood: evaluation for trisomy 21 and trisomy 18", American Journal of Obstetrics and Gynecology, doi: 10.1016/j.ajog.2012.01.030, Jan. 30, 2012, 33 pages.
Storchova, et al., "The consequences of tetraploidy and aneuploidy", Journal of Cell Science 121 (23), 2008, 3859-3866.
Thoma, et al., "Mechanisms of aneuploidy and its suppression by tumour suppressor proteins", Swiss Med Weekly, 141, 2011, w13170.
Turner, et al., "Methods for Genomic Partitioning", Annual Review of Genomics and Human Genetics, vol. 10, No. 1, Sep. 1, 2009, 263-284.
Varmus, H. , "The Molecular Genetics of Cellular Oncogenes", Ann Rev Genetics, vol. 18, 1984, 553-612.
Walsh, et al., "Rare Structural Variants Disrupt Multiple Genes in Neurodevelopmental Pathways in Schizophrenia", Science, vol. 320, 2008, 539-543.
Warren, et al., "Transcription factor profiling in individual hematopoietic progenitors by digital RT-PCR", PNAS, vol. 103 (47), 2006, 17807-17812.

(56) References Cited

OTHER PUBLICATIONS

Wong, et al., "Circulating placental RNA in maternal plasma is associated with a preponderance of 5" mRNA fragments: implications for noninvasive prenatal diagnosis and monitoring", Clinical Chemistry 51:10, 2005, 1786-1795.

Yamada, et al., "PrimerStation: a highly specific multiplex genomic PCR primer design server for the human genome", Nucleic Acids Res., vol. 34, Jul. 1, 2006, W665-W669.

Zhou, et al., "Counting alleles reveals a connection between chromosome 18q loss and vascular invasion", Nature Biotechnology, vol. 19, Jan. 2001, 78-81.

Zhou, et al., "Counting alleles to predict recurrence of early-stage colorectal cancers", The Lancet, vol. 359, Mechanisms of Disease, Jan. 19, 2002, 219-225.

Zhu, et al., "Single Molecule Profiling of Alternative Pre-mRNA Splicing", Science 301, 2003, 836-838.

Zimmermann, et al., "Novel real-time quantitative PCR test for trisomy 21", Clinical Chemistry 48, No. 2, 2002, 362-363.

Ncbi: NCBI assay ID ss3206919 for rr560681, Sep. 5, 2001.

Bauer, M. et al., "A prospective analysis of cell-free fetal DNA concentrationin maternal plasma as an indicator for adverse pregnancyoutcome", Prenatal Diagnosis, vol. 26, Jul. 11, 2006, 831-836.

\* cited by examiner

US 10,662,474 B2

IDENTIFICATION OF POLYMORPHIC SEQUENCES IN MIXTURES OF GENOMIC DNA BY WHOLE GENOME SEQUENCING

CROSS-REFERENCE

This application is a continuation-in-part of application Ser. No. 12/958,347 filed on Dec. 1, 2010, which application is incorporated by reference in its entirety. This application claims priority to U.S. Provisional Application Ser. No. 61/296,358, filed on Jan. 19, 2010; and U.S. Provisional Application Ser. No. 61/360,837, filed on Jul. 1, 2010, which applications are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Feb, 4, 2011, is named 32808770.txt and is 74,234 bytes in size.

FIELD OF THE INVENTION

The invention is applicable to the field of medical diagnostics and particularly relates to whole genome sequencing methods for identifying polymorphisms in samples comprising mixtures of genomes.

BACKGROUND OF THE INVENTION

Prenatal screening and diagnosis are a routine part of antenatal care. Currently, prenatal diagnosis of genetic and chromosomal conditions involves invasive testing, such as amniocentesis or chorionic villus sampling (CVS), performed from 11 weeks gestation and carrying a ~1% risk of miscarriage. The existence of circulating cell-free DNA in maternal blood (Lo et al., Lancet 350:485-487 [1997]) is being exploited for developing noninvasive processes that use fetal nucleic acids from a maternal peripheral blood sample to determine fetal chromosomal aneuploidies e.g. trisomy 21 (Fan H C and Quake S R Anal Chem 79:7576-7579 [2007]: Fan et al., Proc Natl Acad Sci 105:16266-16271 [2008]). These methods offer an alternative and safer source of fetal genetic material for prenatal diagnosis, and could effectively pronounce the end of invasive procedures.

Next Generation Sequencing (NGS) technologies have been used to determine entire human genome sequences (Levy et al. PLoS Biol 55, e254 [2007]; Wheeler et al. Nature 452:872-876 [2008]; Bentley et al., Nature 456:53-59 [2008]), and a broad interest exists in using NGS technologies for whole genome sequencing (WGS) to better understand human genetic variation and genome-related diseases, and ultimately to guide discoveries and decisions about the health of individuals. The extensive public genome-wide database of patterns of common human sequence variation provided by the International HapMap Project, and the increasing accessibility to whole genome sequencing technologies, will lead to the identification of new therapeutic targets and the development of targeted interventions for an individuals' medical care.

An additional need that remains is for identifying the disorder-associated genetic variations when two or more individual genomes are intermixed in a clinical sample e.g. mixtures of fetal and maternal genomes in biological fluid samples obtained from the mother, and mixtures of euploid and aneuploid genomes derived from cells of cancer patients.

The present invention addresses the need by providing a method for identifying polymorphisms in mixtures of genomes present in samples that can be obtained by noninvasive means. The method can be used for the non-invasive identification of multiple disease-associated polymorphisms in a variety of fields including but not limited to prenatal diagnostics, and oncology.

SUMMARY OF THE INVENTION

The present invention relates to methods comprising whole genome sequencing for identifying polymorphisms in samples comprising mixtures of genomes, and for determining and/or monitoring the presence or absence of disorders associated with the identified polymorphisms.

In one embodiment, the invention provides a method for identifying multiple polymorphisms in a first genome of a blood sample comprising a mixture of cfDNA of a first and a second genome, comprising: (a) whole genome sequencing at least a portion of the mixture of cfDNA, thereby obtaining a plurality of sequence tags, wherein the mixture is unenriched for the multiple polymorphisms; (b) comparing the sequence of the plurality of tags to the sequence of multiple reference polymorphisms; (c) identifying the multiple polymorphisms in the first and second genome of the mixture; and (d) associating the multiple polymorphisms identified in step (c) with the first and second genome, thereby identifying the multiple polymorphisms in the first genome of the mixture. The blood sample can be unenriched for polymorphic target sequences in the mixture of first and second genomes. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for identifying multiple polymorphisms in a first genome of a blood sample comprising a mixture of cfDNA of a first and a second genome, comprises: (a) whole genome sequencing at least a portion of the mixture of cfDNA, thereby obtaining a plurality of sequence tags, wherein the mixture is unenriched for the multiple polymorphisms; (b) comparing the sequence of the plurality of tags to the sequence of multiple reference polymorphisms; (c) identifying the multiple polymorphisms in the first and second genome of the mixture; and (d) associating the multiple polymorphisms identified in step (c) with the first and second genome, thereby identifying the multiple polymorphisms in the first genome of the mixture. Step (c) comprises genotyping the second genome in a sample that is substantially free of the first genome. The blood sample can be unenriched for polymorphic target sequences in the mixture of first and second genomes. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for identifying multiple polymorphisms in a first genome of a blood sample comprising a mixture of cfDNA of a first and a second genome, comprises: (a) whole genome sequencing at least a portion of the mixture of cfDNA, thereby obtaining a plurality of sequence tags, wherein the mixture is unenriched for the multiple polymorphisms; (b) comparing the sequence of the plurality of tags to the sequence of multiple reference polymorphisms; (c) identifying the multiple polymorphisms in the first and second genome of the mixture; and (d) associating the multiple polymorphisms identified in step (c) with the first and second genome, thereby identifying the multiple polymorphisms in the first genome of the mixture, wherein step (c) comprises counting sequence tags mapped to the multiple reference polymorphisms. The blood sample can be unenriched for polymorphic target sequences in the mixture of first and second genomes. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for identifying multiple polymorphisms in a first genome of a blood sample comprising a mixture of cfDNA of a first and a second genome, comprises: (a) whole genome sequencing at least a portion of the mixture of cfDNA, thereby obtaining a plurality of sequence tags, wherein the mixture is unenriched for the multiple polymorphisms; (b) comparing the sequence of the plurality of tags to the sequence of multiple reference polymorphisms; (c) identifying the multiple polymorphisms in the first and second genome of the mixture; and (d) associating the multiple polymorphisms identified in step (c) with the first and second genome, thereby identifying the multiple polymorphisms in the first genome of the mixture, wherein the multiple polymorphisms in the first genome are associated with at least one disorder. The blood sample can be unenriched for polymorphic target sequences in the mixture of first and second genomes. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for identifying multiple polymorphisms in a first genome of a blood sample comprising a mixture of cfDNA of a first and a second genome, comprises: (a) whole genome sequencing at least a portion of the mixture of cfDNA, thereby obtaining a plurality of sequence tags, wherein the mixture is unenriched for the multiple polymorphisms; (b) comparing the sequence of the plurality of tags to the sequence of multiple reference polymorphisms; (c) identifying the multiple polymorphisms in the first and second genome of the mixture; and (d) associating the multiple polymorphisms identified in step (c) with the first and second genome, wherein step (c) comprises genotyping said second genome in a sample that is substantially free of said first genome, and wherein the multiple polymorphisms in the first genome are associated with at least one disorder. The blood sample can be unenriched for polymorphic target sequences in the mixture of first and second genomes. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for identifying multiple polymorphisms in a first genome of a blood sample comprising a mixture of cfDNA of a first and a second genome, comprises: (a) whole genome sequencing at least a portion of the mixture of cfDNA, thereby obtaining a plurality of sequence tags, wherein the mixture is unenriched for the multiple polymorphisms; (b) comparing the sequence of the plurality of tags to the sequence of multiple reference polymorphisms; (c) identifying the multiple polymorphisms in the first and second genome of the mixture; and (d) associating the multiple polymorphisms identified in step (c) with the first and second genome, thereby identifying the multiple polymorphisms in the first genome of the mixture, wherein step (c) comprises counting sequence tags mapped to the multiple reference polymorphisms, and wherein the multiple polymorphisms in the first genome are associated with at least one disorder. The blood sample can be unenriched for polymorphic target sequences in the mixture of first and second genomes. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for identifying multiple polymorphisms in a first genome of a blood sample comprising a mixture of cfDNA of a first and a second genome, comprises: (a) whole genome sequencing at least a portion of the mixture of cfDNA, thereby obtaining a plurality of sequence tags, wherein the mixture is unenriched for the multiple polymorphisms; (b) comparing the sequence of the plurality of tags to the sequence of multiple reference polymorphisms; (c) identifying the multiple polymorphisms in the first and second genome of the mixture; and (d) associating the multiple polymorphisms identified in step (c) with the first and second genome, thereby identifying the multiple polymorphisms in the first genome of the mixture. The blood sample is obtained from a pregnant woman, and it can be unenriched for cfDNA of the first or second genome. The first genome is a fetal genome and the second genome is a maternal genome. Optionally, the method further comprises identifying the multiple polymorphisms in a paternal genome. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for identifying multiple polymorphisms in a first genome of a blood sample comprising a mixture of cfDNA of a first and a second genome, comprises: (a) whole genome sequencing at least a portion of the mixture of cfDNA, thereby obtaining a plurality of sequence tags, wherein the mixture is unenriched for the multiple polymorphisms; (b) comparing the sequence of the plurality of tags to the sequence of multiple reference polymorphisms; (c) identifying the multiple polymorphisms in the first and second genome of the mixture; and (d) associating the multiple polymorphisms identified in step (c) with the first and second genome, thereby identifying the multiple polymorphisms in the first genome of the mixture, wherein step (c) comprises genotyping the second genome in a sample that is substantially free of the first genome. The blood sample is obtained from a pregnant woman, and it can be unenriched for cfDNA of the first or second genome. The first genome is a fetal genome and the second genome is a maternal genome. Optionally, the method further comprises identifying the multiple polymorphisms in a paternal genome. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for identifying multiple polymorphisms in a first genome of a blood sample comprising a mixture of cfDNA of a first and a second genome, comprises: (a) whole genome sequencing at least a portion of the mixture of cfDNA, thereby obtaining a plurality of sequence tags, wherein the mixture is unenriched for the multiple polymorphisms; (b) comparing the sequence of the plurality of tags to the sequence of multiple reference polymorphisms; (c) identifying the multiple polymorphisms in the first and second genome of the mixture; and (d) associating the multiple polymorphisms identified in step (c) with the first and second genome, thereby identifying the multiple polymorphisms in the first genome of the mixture, wherein step (c) comprises counting sequence tags mapped to the multiple reference polymorphisms. The blood sample is obtained from a pregnant woman, and it can be unenriched for cfDNA of the first or second genome. The first genome is a fetal genome and the second genome is a maternal genome. Optionally, the method further comprises identifying the multiple polymorphisms in a paternal genome. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for identifying multiple polymorphisms in a first genome of a blood sample comprising a mixture of cfDNA of a first and a second genome, comprises: (a) whole genome sequencing at least a portion of the mixture of cfDNA, thereby obtaining a plurality of sequence tags, wherein the mixture is unenriched for the multiple polymorphisms; (b) comparing the sequence of the plurality of tags to the sequence of multiple reference polymorphisms; (c) identifying the multiple polymorphisms in the first and second genome of the mixture; and (d) associating the multiple polymorphisms identified in step (c) with the first and second genome, thereby identifying the multiple polymorphisms in the first genome of the mixture. The sample is a blood sample obtained from a subject that is known or suspected of having cancer. The blood sample can be unenriched for polymorphic target sequences in the mixture of first and second genomes. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for identifying multiple polymorphisms in a first genome of a blood sample comprising a mixture of cfDNA of a first and a second genome, comprises: (a) whole genome sequencing at least a portion of the mixture of cfDNA, thereby obtaining a plurality of sequence tags, wherein the mixture is unenriched for the multiple polymorphisms; (b) comparing the sequence of the plurality of tags to the sequence of multiple reference polymorphisms; (c) identifying the multiple polymorphisms in the first and second genome of the mixture; and (d) associating the multiple polymorphisms identified in step (c) with the first and second genome, thereby identifying the multiple polymorphisms in the first genome of the mixture, wherein step (c) comprises genotyping the second genome in a sample that is substantially free of the first genome. The sample is a blood sample obtained from a subject that is known or suspected of having cancer. The blood sample can be unenriched for polymorphic target sequences in the mixture of first and second genomes. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for identifying multiple polymorphisms in a first genome of a blood sample comprising a mixture of cfDNA of a first and a second genome, comprises: (a) whole genome sequencing at least a portion of the mixture of cfDNA, thereby obtaining a plurality of sequence tags, wherein the mixture is unenriched for the multiple polymorphisms; (b) comparing the sequence of the plurality of tags to the sequence of multiple reference polymorphisms; (c) identifying the multiple polymorphisms in the first and second genome of the mixture; and (d) associating the multiple polymorphisms identified in step (c) with the first and second genome, thereby identifying the multiple polymorphisms in the first genome of the mixture, wherein step (c) comprises counting sequence tags mapped to the multiple reference polymorphisms. The sample is a blood sample obtained from a subject that is known or suspected of having cancer. The blood sample can be unenriched for polymorphic target sequences in the mixture of first and second genomes. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the invention provides a method for determining the presence or absence of multiple disorders in a blood sample comprising a mixture of cfDNA of a first and a second genome, comprising: (a) whole genome sequencing at least a portion of the mixture of cfDNA, thereby providing a plurality of sequence tags; (b) identifying multiple polymorphisms in the plurality of sequence tags, wherein the multiple polymorphisms are associated with the number of disorders; and (c) associating the multiple polymorphisms with the first and/or second genome in the mixture, wherein the mixture is unenriched for the multiple polymorphisms. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for determining the presence or absence of multiple disorders in a blood sample comprising a mixture of cfDNA of a first and a second genome, comprises: (a) whole genome sequencing at least a portion of the mixture of cfDNA, thereby providing a plurality of sequence tags; (b) identifying multiple polymorphisms in the plurality of sequence tags, wherein the multiple polymorphisms are associated with the number of disorders; and (c) associating the multiple polymorphisms with the first and/or second genome in the mixture, wherein the mixture is unenriched for the multiple polymorphisms. The method further comprises comparing the sequence of the plurality of tags to the sequence of multiple reference polymorphisms, thereby identifying the multiple polymorphisms in the mixture of cfDNA. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for determining the presence or absence of multiple disorders in a blood sample comprising a mixture of cfDNA of a first and a second genome, comprises: (a) whole genome sequencing at least a portion of the mixture of cfDNA, thereby providing a plurality of sequence tags; (b) identifying multiple polymorphisms in the plurality of sequence tags, wherein the multiple polymorphisms are associated with the number of disorders; and (c) associating the multiple polymorphisms with the first and/or second genome in the mixture, wherein the mixture is unenriched for the multiple polymorphisms. In some embodiments, step (b) comprises counting sequence tags mapped to the multiple polymorphisms. Alternatively, step (b) comprises genotyping the second genome in a sample that is substantially free of the first genome. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for determining the presence or absence of multiple disorders in a blood sample comprising a mixture of cfDNA of a first and a second genome, comprises: (a) whole genome sequencing at least a portion of the mixture of cfDNA, thereby providing a plurality of sequence tags; (b) identifying multiple polymorphisms in the plurality of sequence tags, wherein the multiple polymorphisms are associated with the number of disorders; and (c) associating the multiple polymorphisms with the first and/or second genome in the mixture, wherein the mixture is unenriched for the multiple polymorphisms, wherein the first genome is a genome of an unaffected cell and the second genome is a genome from an affected cell. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for determining the presence or absence of multiple disorders in a blood sample comprising a mixture of cfDNA of a first and a second genome, comprises: (a) whole genome sequencing at least a portion of the mixture of cfDNA, thereby providing a plurality of sequence tags; (b) identifying multiple polymorphisms in the plurality of sequence tags, wherein the multiple polymorphisms are associated with the number of disorders; and (c) associating the multiple polymorphisms with the first and/or second genome in the mixture, wherein the mixture is unenriched for the multiple polymorphisms, and wherein the first genome is a genome of an unaffected cell and the second genome is a genome from an affected cell. The method further comprises comparing the sequence of the plurality of tags to the sequence of multiple reference polymorphisms, thereby identifying the multiple polymorphisms in the mixture of cfDNA. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for determining the presence or absence of multiple disorders in a blood sample comprising a mixture of cfDNA of a first and a second genome, comprises: (a) whole genome sequencing at least a portion of the mixture of cfDNA, thereby providing a plurality of sequence tags; (b) identifying multiple polymorphisms in the plurality of sequence tags, wherein the multiple polymorphisms are associated with the number of disorders; and (c) associating the multiple polymorphisms with the first and/or second genome in the mixture, wherein the mixture is unenriched for the multiple polymorphisms, and wherein the first genome is a genome of an unaffected cell and the second genome is a genome from an affected cell. In some embodiments, step (b) comprises counting sequence tags mapped to the multiple polymorphisms. Alternatively, step (b) comprises genotyping the second genome in a sample that is substantially free of the first genome. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for determining the presence or absence of multiple disorders in a blood sample comprising a mixture of cfDNA of a first and a second genome, comprises: (a) whole genome sequencing at least a portion of the mixture of cfDNA, thereby providing a plurality of sequence tags; (b) identifying multiple polymorphisms in the plurality of sequence tags, wherein the multiple polymorphisms are associated with the number of disorders; and (c) associating the multiple polymorphisms with the first and/or second genome in the mixture, wherein the mixture is unenriched for the multiple polymorphisms. In some embodiments the disorder is a monogenic disorder. Alternatively, the disorder is a polygenic disorder. In other embodiments, the disorder is cancer. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for determining the presence or absence of multiple disorders in a blood sample comprising a mixture of cfDNA of a first and a second genome, comprises: (a) whole genome sequencing at least a portion of the mixture of cfDNA, thereby providing a plurality of sequence tags; (b) identifying multiple polymorphisms in the plurality of sequence tags, wherein the multiple polymorphisms are associated with the number of disorders; and (c) associating the multiple polymorphisms with the first and/or second genome in the mixture, wherein the mixture is unenriched for the multiple polymorphisms. The method further comprises comparing the sequence of the plurality of tags to the sequence of multiple reference polymorphisms, thereby identifying the multiple polymorphisms in the mixture of cfDNA. In some embodiments the disorder is a monogenic disorder. Alternatively, the disorder is a polygenic disorder. In other embodiments, the disorder is cancer. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for determining the presence or absence of multiple disorders in a blood sample comprising a mixture of cfDNA of a first and a second genome, comprises: (a) whole genome sequencing at least a portion of the mixture of cfDNA, thereby providing a plurality of sequence tags; (b) identifying multiple polymorphisms in the plurality of sequence tags, wherein the multiple polymorphisms are associated with the number of disorders; and (c) associating the multiple polymorphisms with the first and/or second genome in the mixture, wherein the mixture is unenriched for the multiple polymorphisms. In some embodiments, step (b) comprises counting sequence tags mapped to the multiple polymorphisms. Alternatively, step (b) comprises genotyping the second genome in a sample that is substantially free of the first genome. In some embodiments the disorder is a monogenic disorder. Alternatively, the disorder is a polygenic disorder. In other embodiments, the disorder is cancer. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for determining the presence or absence of multiple disorders in a blood sample comprising a mixture of cfDNA of a first and a second genome, comprises: (a) whole genome sequencing at least a portion of the mixture of cfDNA, thereby providing a plurality of sequence tags; (b) identifying multiple polymorphisms in the plurality of sequence tags, wherein the multiple polymorphisms are associated with the number of disorders; and (c) associating the multiple polymorphisms with the first and/or second genome in the mixture, wherein the mixture is unenriched for the multiple polymorphisms. The first genome is a fetal genome and the second genome is a maternal genome. Optionally, the method further comprises determining the presence or absence of the multiple polymorphisms in a cellular paternal genome. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for determining the presence or absence of multiple disorders in a blood sample comprising a mixture of cfDNA of a first and a second genome, comprises: (a) whole genome sequencing at least a portion of the mixture of cfDNA, thereby providing a plurality of sequence tags; (b) identifying multiple polymorphisms in the plurality of sequence tags, wherein the multiple polymorphisms are associated with the number of disorders; and (c) associating the multiple polymorphisms with the first and/or second genome in the mixture, wherein the mixture is unenriched for the multiple polymorphisms. The method further comprises comparing the sequence of the plurality of tags to the sequence of multiple reference polymorphisms, thereby identifying the multiple polymorphisms in the mixture of cfDNA. The first genome is a fetal genome and the second genome is a maternal genome. Optionally, the method further comprises determining the presence or absence of the multiple polymorphisms in a cellular paternal genome. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for determining the presence or absence of multiple disorders in a blood sample comprising a mixture of cfDNA of a first and a second genome, comprises: (a) genome sequencing at least a portion of the mixture of cfDNA, thereby providing a plurality of sequence tags; (b) identifying multiple polymorphisms in the plurality of sequence tags, wherein the multiple polymorphisms are associated with the number of disorders; and (c) associating the multiple polymorphisms with the first and/or second genome in the mixture, wherein the mixture is unenriched for the multiple polymorphisms. In some embodiments, step (b) comprises counting sequence tags mapped to the multiple polymorphisms. Alternatively, step (b) comprises genotyping the second genome in a sample that is substantially free of the first genome. The first genome is a fetal genome and the second genome is a maternal genome. Optionally, the method further comprises determining the presence or absence of the multiple polymorphisms in a cellular paternal genome. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the invention provides a method for determining the presence or absence of multiple fetal disorders in a maternal blood sample comprising a mixture of fetal and maternal cfDNA, the method comprising: (a) whole genome sequencing at least a portion of the mixture of fetal and maternal cfDNA, thereby obtaining a plurality of sequence tags; (b) identifying multiple fetal polymorphisms in the plurality of sequence tags, thereby determining multiple fetal haplotypes associated with the multiple fetal disorders; and (c) determining the presence or absence of the at least one fetal disorder. Optionally, the method further comprises sequencing paternal cellular DNA. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for determining the presence or absence of multiple fetal disorders in a maternal blood sample comprising a mixture of fetal and maternal cfDNA, comprises: (a) whole genome sequencing at least a portion of the mixture of fetal and maternal cfDNA, thereby obtaining a plurality of sequence tags; (b) identifying multiple fetal polymorphisms in the plurality of sequence tags, thereby determining multiple fetal haplotypes associated with the multiple fetal disorders; and (c) determining the presence or absence of the at least one fetal disorder. Optionally, the method further comprises sequencing paternal cellular DNA. In some embodiments, step (b) comprises genotyping maternal cellular DNA thereby identifying multiple polymorphisms in the maternal cellular DNA. Alternatively, step (b) comprises counting tags mapped to the fetal and maternal polymorphisms in the mixture. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for determining the presence or absence of multiple fetal disorders in a maternal blood sample comprising a mixture of fetal and maternal cfDNA, comprises: (a) whole genome sequencing at least a portion of the mixture of fetal and maternal cfDNA, thereby obtaining a plurality of sequence tags; (b) identifying multiple fetal polymorphisms in the plurality of sequence tags, thereby determining multiple fetal haplotypes associated with the multiple fetal disorders; and (c) determining the presence or absence of the at least one fetal disorder. Optionally, the method further comprises sequencing paternal cellular DNA. Each of the multiple fetal polymorphisms comprises at least one SNP, a tandem SNP or an STR. In some embodiments, the at least one SNP is a tag SNP. In other embodiments, the at least one STR is a tag STR. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for determining the presence or absence of multiple fetal disorders in a maternal blood sample comprising a mixture of fetal and maternal cfDNA, comprises: (a) whole genome sequencing at least a portion of the mixture of fetal and maternal cfDNA, thereby obtaining a plurality of sequence tags; (b) identifying multiple fetal polymorphisms in the plurality of sequence tags, thereby determining multiple fetal haplotypes associated with the multiple fetal disorders; and (c) determining the presence or absence of the at least one fetal disorder, wherein step (b) comprises genotyping maternal cellular DNA thereby identifying multiple polymorphisms in the maternal cellular DNA. Each of the multiple fetal polymorphisms comprises at least one SNP, a tandem SNP or an STR. In some embodiments, the at least one SNP is a tag SNP. In other embodiments, the at least one STR is a tag STR. Optionally, the method further comprises sequencing paternal cellular DNA. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

In another embodiment, the method for determining the presence or absence of multiple fetal disorders in a maternal blood sample comprising a mixture of fetal and maternal cfDNA, comprises: (a) whole genome sequencing at least a portion of the mixture of fetal and maternal cfDNA, thereby obtaining a plurality of sequence tags; (b) identifying multiple fetal polymorphisms in the plurality of sequence tags, thereby determining multiple fetal haplotypes associated with the multiple fetal disorders; and (c) determining the presence or absence of the at least one fetal disorder, wherein step (b) comprises counting tags mapped to the fetal and maternal polymorphisms in the mixture. Each of the multiple fetal polymorphisms comprises at least one SNP, a tandem SNP or an STR. In some embodiments, the at least one SNP is a tag SNP. In other embodiments, the at least one STR is a tag STR. Optionally, the method further comprises sequencing paternal cellular DNA. Sequencing is massively parallel sequencing of clonally amplified cfDNA molecules or of single cfDNA molecules. In some embodiments, sequencing is performed using massively parallel sequencing-by-synthesis with reversible dye terminators. In other embodiments, sequencing is performed using massively parallel sequencing-by-ligation. In some embodiments, the sample is a plasma sample.

Although the examples herein concern humans and the language is primarily directed to human concerns, the concept of this invention is applicable to genomes from any plant or animal.

INCORPORATION BY REFERENCE

All patents, patent applications, and other publications, including all sequences disclosed within these references, referred to herein are expressly incorporated by reference, to the same extent as if each individual publication, patent or patent application was specifically and individually indicated to be incorporated by reference. All documents cited are, in relevant part, incorporated herein by reference. However, the citation of any document is not to be construed as an admission that it is prior art with respect to the present invention.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
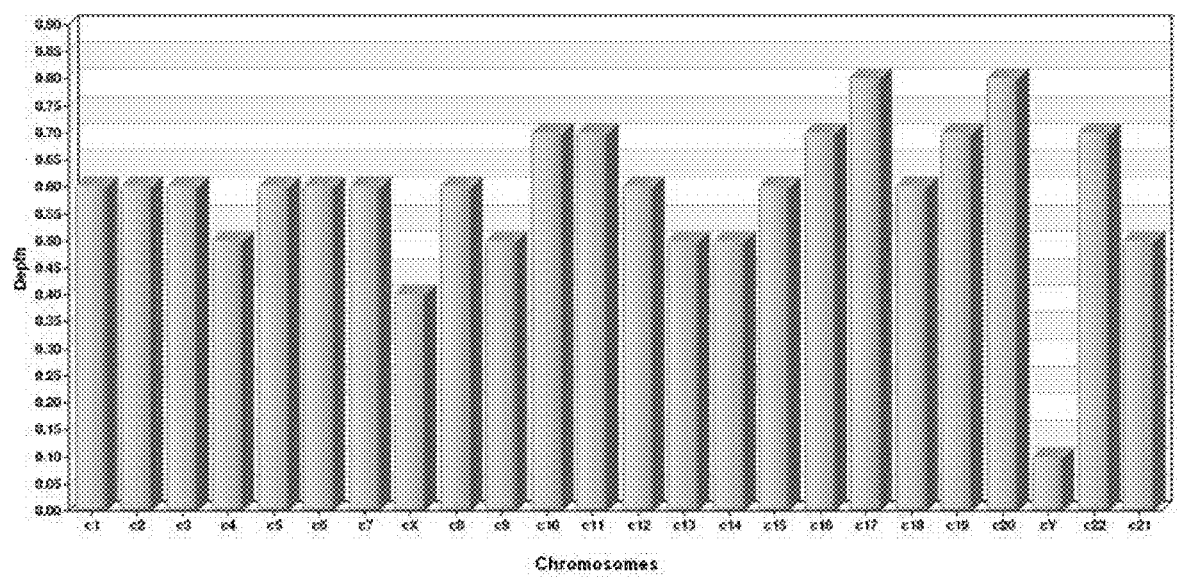
FIG. 1 shows the percent coverage of individual chromosomes determined by whole genome sequencing of a combination of maternal samples comprising a mixture of fetal and maternal cfDNA as a function of depth. A maximum depth of 1 represents 100% coverage of each chromosome.

The present invention relates to methods comprising whole genome sequencing for identifying polymorphisms in samples comprising mixtures of genomes, and for determining and/or monitoring the presence or absence of disorders associated with the identified polymorphisms.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous standard texts and reference works. All patents, patent applications, articles and publications mentioned herein are hereby expressly incorporated herein by reference in their entirety.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not limitations of the various aspects or embodiments of the invention which can be had by reference to the Specification as a whole. Accordingly, as indicated above, the terms defined immediately below are more fully defined by reference to the specification as a whole.

Unless defined otherwise herein, all technical and scientific terms used herein have the same meaning as commonly understood by one of ordinary skill in the art to which this invention belongs. Various scientific dictionaries that include the terms included herein are well known and available to those in the art. Although any methods and materials similar or equivalent to those described herein find use in the practice or testing of the present invention, some preferred methods and materials are described. Accordingly, the terms defined immediately below are more fully described by reference to the Specification as a whole. It is to be understood that this invention is not limited to the particular methodology, protocols, and reagents described, as these may vary, depending upon the context they are used by those of skill in the art.

Definitions

As used herein, the singular terms "a", "an," and "the" include the plural reference unless the context clearly indicates otherwise. Unless otherwise indicated, nucleic acids are written left to right in 5' to 3' orientation and amino acid sequences are written left to right in amino to carboxy orientation, respectively. The term "assessing" herein refers to characterizing the status of a chromosomal aneuploidy by one of three types of calls: "normal", "affected", and "no-call". For example, in the presence of trisomy the "normal" call is determined by the value of a parameter e.g. a test chromosome dose that is below a user-defined threshold of reliability, the "affected" call is determined by a parameter e.g. a test chromosome dose, that is above a user-defined threshold of reliability, and the "no-call" result is determined by a parameter e.g. a test chromosome dose, that lies between the a user-defined thresholds of reliability for making a "normal" or an "affected" call.

The terms "polymorphism" and "polymorphic sequences" are herein used interchangeably to refer to the occurrence of two or more genetically determined alternative sequences or alleles in a population. Each divergent sequence is termed an allele, and can be part of a gene or located within an intergenic or non-genic sequence. A diallelic polymorphism has two alleles, and a triallelic polymorphism has three alleles. Diploid organisms can contain two alleles and may be homozygous or heterozygous for allelic forms. The first identified allelic form is arbitrarily designated the reference form or allele; other allelic forms are designated as alternative or variant alleles. The most frequently occurring allelic form in a selected population is typically referred to as the wild-type form. Polymorphisms encompass sequence differences that include single nucleotide polymorphisms (SNPs), tandem SNPs, small-scale multi-base deletions or insertions, called IN-DELS (also called deletion insertion polymorphisms or DIPs), Multi-Nucleotide Polymorphisms (MNPs), Short Tandem Repeats (STRs), restriction fragment length polymorphism (RFLP), deletions, including microdeletions, insertions, including microinsertions, duplications, inversions, translocations, multiplications, complex multi-site variants, copy number variations (CNV), and polymorphisms comprising any other change of sequence in a chromosome. Differences in genomic sequences include combinations of polymorphisms. For example, polymorphisms can encompass the combination of one or more SNPs and one or more STR. Polymorphisms can be indicative, informative, or both. For example, indicative polymorphisms indicate the presence of fetal cell-free DNA in a maternal sample. Informative polymorphisms yield information about the fetus—for example, the presence or absence of a disorder, abnormality, or any other biological information such as the stage of gestation or gender.

The term "copy number variation" herein refers to variation in the number of copies of a nucleic acid sequence that is 1 kb or larger present in a test sample in comparison with the copy number of the nucleic acid sequence present in a qualified sample. A "copy number variant" refers to the 1 kb or larger sequence of nucleic acid in which copy-number differences are found by comparison of a sequence of interest in test sample with that present in a qualified sample. Copy number variants/variations include deletions, including microdeletions, insertions, including microinsertions, duplications, multiplications, inversions, translocations and complex multi-site variants. CNV encompass chromosomal aneuploidies and partial aneuplodies.

The term "single nucleotide polymorphism (SNP)" refers to a single base (nucleotide) polymorphism in a DNA sequence among individuals in a population. A SNP may be present within coding sequences of genes, non-coding regions of genes, or in the intergenic regions between genes. SNPs within a coding sequence will not necessarily change the amino acid sequence of the protein that is produced, due to degeneracy of the genetic code. A SNP in which both forms lead to the same polypeptide sequence is termed "synonymous" (sometimes called a silent mutation)—if a different polypeptide sequence is produced they are "non-synonymous". A nonsynonymous change may either be missense or "nonsense", where a missense change results in a different amino acid, while a nonsense change results in a premature stop codon. SNPs can also arise from a deletion of a nucleotide or an insertion of a nucleotide relative to a reference allele. Single nucleotide polymorphisms (SNPs) are positions at which two alternative bases occur at appreciable frequency (>1%) in the human population, and are the most common type of human genetic variation.

The term "tandem SNPs" herein refers to two or more SNPs that are present within a polymorphic target nucleic acid sequence.

The term "short tandem repeat" or "STR" herein refers to a class of polymorphisms that occurs when a pattern of two or more nucleotides are repeated and the repeated sequences are directly adjacent to each other. The pattern can range in length from 2 to 10 base pairs (bp) (for example (CATG)n in a genomic region) and is typically in the non-coding intron region. By examining several STR loci and counting how many repeats of a specific STR sequence there are at a given locus, it is possible to create a unique genetic profile of an individual.

The term "sample" herein refers to a biological specimen comprising a mixture of two or more genomes. Biological specimens include tissue samples, biological fluid samples, or cell samples.

The term "maternal sample" unless otherwise specified, herein refers to a biological sample obtained from a pregnant subject that comprises a mixture of fetal and maternal nucleic acids e.g. cfDNA.

As used herein, the terms "aligned", "alignment", or "aligning" refer to one or more sequences that are identified as a match in terms of the order of their nucleic acid molecules to a known sequence from a reference genome. Such alignment can be done manually or by a computer algorithm, examples including the Efficient Local Alignment of Nucleotide Data (ELAND) computer program distributed as part of the Illumina Genomics Analysis pipeline. The matching of a sequence read in aligning can be a 100% sequence match or less than 100% (non-perfect match).

The term "sequence tag" is herein used interchangeably with the term "mapped sequence tag" to refer to a sequence read that has been specifically assigned i.e. mapped, to a larger sequence e.g. a reference genome, by alignment. Mapped sequence tags are uniquely mapped to a reference genome i.e. they are assigned to a single location to the reference genome. Tags that can be mapped to more than one location on a reference genome i.e. tags that do not map uniquely, are not included in the analysis.

The term "read" refers to a DNA sequence of sufficient length (e.g., at least about 30 bp) that can be used to identify a larger sequence or region, e.g. that can be aligned and specifically assigned to a chromosome or genomic region or gene.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

The term "transrenal-DNA (Tr-DNA)" herein refers to DNA that has crosses the kidney barrier and is found in urine.

The term "mixture" is used herein to refer to a mixture of nucleic acids e.g. DNA, that are present in a sample and are derived from two or more genomes. A non-limiting example of a mixture of nucleic acids is a maternal blood sample that comprises a mixture of fetal and maternal genomic cell-free DNA.

The term "Whole Genome Sequencing (WGS)" herein refers to a process whereby the sequence of the entire genome of an organism, for example, humans, dogs, mice, viruses or bacteria can be determined. It is not necessary that the entire genome actually be sequenced. The WGS methods of the invention are those sequencing methods that when applied to a sample of genomic DNA are capable of obtaining the sequence of the entire genome. Whole genome sequencing can be performed using any NGS technology as described herein.

The term "sequencing" herein refers to a method for determining the nucleotide sequence of a polynucleotide e.g. genomic DNA. Preferably, sequencing methods include as non-limiting examples next generation sequencing (NGS) methods, (NGS) in which clonally amplified DNA templates or single DNA molecules are sequenced in a massively parallel fashion (e.g. as described in Volkerding et al. Clin Chem 55:641-658 [2009]; Metzker M Nature Rev 11:31-46 [2010]).

The term "at least as portion" herein refers to a fraction of the total genomic DNA present in a sample comprising a mixture of DNA from two different genomes that represents at least one genome equivalent. For example, "at least a portion" of cfDNA in a blood sample comprising a mixture of cfDNA derived from two different genomes refers the fraction of the total cfDNA in the mixture that represents at least one copy of one of the two genomes.

The term "genome equivalent" herein refers to the amount of DNA necessary to be present in a sample to guarantee that all genes will be present. This number increases with the total genome size of an organism and can be calculated by converting the size of a genome in base pairs to micrograms of DNA.

The term "cellular" when used in reference to a genome or genomic DNA refers to the genomic content of a cell that can be artificially extracted by methods known in the art.

The term "cell-free" when used in reference to a genome or genomic DNA refers to the genomic content of a cell that is naturally released from cells by biological process such as necrosis and apoptosis.

The term "sequence tag" is herein used interchangeably with the term "mapped sequence tag" to refer to a sequence read that has been specifically assigned i.e. mapped, to a larger sequence e.g. a reference genome, by alignment. Mapped sequence tags are uniquely mapped to a reference genome i.e. they are assigned to a single location to the reference genome. Tags that can be mapped to more than one location on a reference genome i.e. tags that do not map uniquely, are not included in the analysis.

The term "plurality" is used herein in reference to a number of sequence tags that is sufficient to identify sequence differences that exist between two genomes. Sequence differences include polymorphisms found in genomes among subjects of the same species e.g. fetal and maternal genomes. The number of sequence tags that constitutes the plurality of sequence tags depends on the size of the genomes and the sequencing technology used to identify the differences. The plurality of sequence tags sufficient to identify sequence differences between two genomes will be greater when using sequencing technology that results in shorter tags e.g. 36 base pair tags, than when using sequencing technology that provides 500 base pair long tags. For example, X 36 base pair sequence tags and Y 500 base pair sequence tags are needed respectively, to encompass all of the approximately $3 \times 10^9$ base pairs of the human genome.

The term "enriched" is used herein in reference to one or more sequences present in a sample comprising a mixture of genomic DNA that have been amplified to augment the number of copies of the one or more sequences in the sample. For example, a sample comprising a mixture of genomic DNA can be enriched for specific polymorphic target sequences. Alternatively, a sample comprising a mixture of genomic DNA can be enriched non-specifically for sequences contained in the mixture e.g. all the genomic DNA sequences can be amplified to enrich the sample.

The terms "polymorphic target nucleic acid", "polymorphic sequence", "polymorphic target nucleic acid sequence" and "polymorphic nucleic acid" are used interchangeably herein to refer to a nucleic acid sequence e.g. a DNA sequence, that comprises one or more polymorphic sites i.e. polymorphisms.

The term "sequence tag density" herein refers to the number of sequence reads that are mapped to a reference genome sequence.

The term "sequence dose" herein refers to a parameter that relates the sequence tag density of a sequence of interest to the tag density of a normalizing sequence. A "test sequence dose" is a parameter that relates the sequence tag density of a sequence of interest determined in a test sample. Similarly, a "qualified sequence dose" is a parameter that relates the sequence tag density of a sequence of interest to that of a normalizing sequence determined in a qualified sample.

The term "normalizing sequence" herein refers to a sequence that displays a variability in the number of sequence tags that are mapped to it among samples and sequencing runs that best approximates that of the sequence of interest for which it is used as a normalizing parameter, and that can best differentiate an affected sample from one or more unaffected samples. A "normalizing chromosome" is an example of a "normalizing sequence".

The term "sequence of interest" herein refers to a nucleic acid sequence that is associated with a difference in sequence representation in healthy versus diseased individuals. A "qualified sequence of interest" is a sequence of interest in a qualified sample. A "test sequence of interest" is a sequence of interest in a test sample.

The term "qualified sample" herein refers to a sample comprising a mixture of nucleic acids that are present in a sample that is normal e.g. not aneuploid, for the sequence of interest.

The term "test sample" herein refers to a sample comprising a mixture of nucleic acids comprising at least one nucleic acid sequence that is suspected of having undergone variation. Nucleic acids present in a test sample are referred to as "test nucleic acids".

The term "unenriched" is used herein in reference to a mixture of genomic DNA that has not been specifically or non-specifically enriched for sequence(s) comprised in the mixture.

As used herein, the term "enriched library" herein refers to a sequencing library comprising amplified polymorphic target nucleic acid sequences. An example of an enriched library is a sequencing library comprising naturally-occurring cfDNA sequences and amplified target nucleic acid sequences. An "unenriched library" herein refers to a sequencing library that does not comprise i.e. a library generated from naturally-occurring cfDNA sequences. A "polymorphic target nucleic acid library" is a library generated from amplified target nucleic acids".

As used herein, the term "purified" refers to material (e.g., an isolated polynucleotide) that is in a relatively pure state, e.g., at least about 80% pure, at least about 85% pure, at least about 90% pure, at least about 95% pure, at least about 98% pure, or even at least about 99% pure.

As used herein, the term "substantially cell free" encompasses preparations of the desired sample from which components that are normally associated with it are removed. For example, a plasma sample is rendered essentially cell free by removing blood cells e.g. red cells, which are normally associated with it.

The term "selective" when used in reference to whole genome amplification refers to the amplification of one of the two genomes present in the sample. For example, selective non-specific enrichment of genomic DNA in a sample comprising DNA molecules derived from two genomes refers to the whole genome enrichment of a selected i.e. one of two, genomes.

The term "whole genome amplification" herein refers to a process whereby DNA sequences present in a sample are amplified to provide multiple copies of the genome that the sequences represent.

The term "polymorphic reference sequences" herein refers to known variant sequences that predominate in a natural population. Polymorphic reference sequences can also refer to variant sequences present in a genome present in a sample comprising a mixture of two or more genomes, to which polymorphisms of other genomes are compared.

The term "associated" is used herein in reference to sequence differences e.g. polymorphisms, that are known to be linked to a disorder. The association of one or more polymorphisms with a disorder can result in the disorder or can represent the genetic predisposition i.e. risk, of developing the disorder.

The terms "disorder" and "genetic disorders'" are used herein interchangeably to refer to conditions or diseases that are caused in whole or in part by alterations in genes or chromosomes. The alterations in genes or chromosomes can be inherited, or can be the result of external factors such as infectious diseases. Disorders encompass single gene disorders including autosomal dominant, autosomal recessive, X-linked dominant, X-linked recessive, Y-linked, and polygenic disorders.

The term "unaffected" when used in reference to a cell refers to a cell having a genome devoid of variations known or suspected to be associated with a genetic disorder. Conversely, an "affected" cell is a cell having a genome comprising one or more variations e.g. polymorphisms, that are known or suspected to be associated with a genetic disorder.

The term "allele" herein refers to a sequence variant of a genetic sequence. For purposes of this application, alleles can but need not be located within a gene sequence. Alleles can be identified with respect to one or more polymorphic positions such as SNPs, while the rest of the gene sequence can remain unspecified. For example, an allele may be defined by the nucleotide present at a single SNP, or by the nucleotides present at a plurality of SNPs.

The term "monogenic disorder" herein refers to diseases that result from modifications in a single gene occurring in all cells of the body, and can be classified as dominant, recessive, X-linked, Y-linked and mitochondrial diseases. Monogenic disorders include pure genetic diseases that are caused by a single error in a single gene in the human DNA.

The term "polygenic disorder" herein refers to a genetic disorder resulting from the combined action of alleles of more than one gene (e.g., heart disease, diabetes, and some cancers). Although such disorders are inherited, they depend on the simultaneous presence of several alleles; thus the hereditary patterns usually are more complex than those of single-gene disorders.

The term "haplotype" refers to a DNA sequence comprising one or more polymorphisms of interest contained on a subregion of a single chromosome of an individual. The polymorphisms of a haplotype can be of the same type e.g. all SNPs, or can be a combination of two or more types of polymorphisms e.g. a combinations of SNPs and STRs. A haplotype can refer to a set of polymorphisms in a single gene, an intergenic sequence, or in larger sequences including both gene and intergenic sequences, e.g., a collection of genes, or of genes and intergenic sequences. For example, a haplotype can refer to a set of polymorphisms in the regulation of complement activation (RCA) locus, which includes gene sequences for complement factor H(CFH), FHR3, FHR1, FHR4, FHR2, FHR5, and F13B and intergenic sequences (i.e., intervening intergenic sequences, upstream sequences, and downstream sequences that are in linkage disequilibrium with polymorphisms in the genic region). A haplotype, for instance, can be a set of maternally inherited alleles, or a set of paternally inherited alleles, at any locus.

The term "haplotyping" herein refers to a process for determining one or more haplotypes in an individual and includes use of family pedigrees, molecular techniques and/or statistical inference. Preferably, haplotypes are determined by sequencing using next generation sequencing technologies.

The term "haplotype block" herein refers to sites of closely located SNPs which are inherited in blocks. A haplotype block includes a group of SNP locations that do not appear to recombine independently and that can be grouped together. Regions corresponding to blocks have a few common haplotypes which account for a large proportion of chromosomes. Identification of haplotype blocks is a way of examining the extent of linkage disequilibrium (LD) in the genome. The "Hap-Map" project (see the internet at the Hap-Map website) describes the mapping of haplotype blocks in the human genome.

The term "tag polymorphism" herein refers to a polymorphism that by itself or in combination with additional polymorphisms indicates the presence of a specific haplotype, or of one member of a group of haplotypes. Examples of tag polymorphisms include without limitation tag SNPs and tag STRs. The haplotype or haplotypes can indicate a genetic factor is associated with risk for disease, thus for example, a tag SNP or combination of tag SNPs indicates the presence or absence of risk factors for disease. A "tag SNP" and a "tag STR" are a representative single nucleotide polymorphism (SNP) and a representative STR, respectively, in a region of the genome with high linkage disequilibrium (the non-random association of alleles at two or more loci) that is associated with a disease. Detecting the presence of at least one tag SNP and/or STR means detecting the presence of a risk allele of a tag SNP and/or STR.

The term "linkage" herein refers to an association of two or more loci at positions on the same chromosome, such that recombination between the two loci is reduced to a proportion significantly less than 50%. The term linkage can also be used in reference to the association between one or more loci and a trait if an allele (or alleles) and the trait, or absence thereof, are observed together in significantly greater than 50% of occurrences. A linkage group is a set of loci, in which all members are linked either directly or indirectly to all other members of the set.

The term "Linkage Disequilibrium" herein refers to the co-occurrence of two genetic loci (e.g., markers) at a frequency greater than expected for independent loci based on the allele frequencies. Linkage disequilibrium (LD) typically occurs when two loci are located close together on the same chromosome. When alleles of two genetic loci (such as a marker locus and a causal locus) are in strong LD, the allele observed at one locus (such as a marker locus) is predictive of the allele found at the other locus (for example, a causal locus contributing to a phenotypic trait). The linkage disequilibrium (LD) measure r.sup.2 (the squared correlation coefficient) can be used to evaluate how for example SNPs are related on a haplotype block.

The term "depth" when used in reference to sequencing of a chromosome, herein refers to the relative coverage of a chromosome by sequencing tags. A maximum depth of 1 indicates that 100% of the sequenced chromosome was covered by sequencing tags.

The term "coverage" when used in reference to the sequencing of a chromosome, herein refers to the amount of a chromosome sequence that is included in the sequencing tags that map to the chromosome. For example, a 1× coverage of a chromosome means that a sufficient number of sequence tags have been obtained to span the entire chromosome once.

The "subject" as used in the specification refers to any organism with at least diploid genome including, but not limited to worms, fish, insects, plants, murine and other mammals including domestic animals such as cows, horse, dogs, cats, and, most preferably humans.

The term "polymorphic target sequence" herein refers to a polymorphic sequence i.e. a sequence that comprises a polymorphism, that is selected for amplification in a sample comprising a mixture of two genomes. A "polymorphic target sequence of interest" herein refers to a selected polymorphic sequence that is known to be associated with a disorder.

The term "whole genome amplification" or "WGA" as used herein generally refers to a method for amplification of a limited DNA sample in a non-specific manner in order to generate a new sample that is indistinguishable from the original but with a higher DNA concentration. The ideal whole genome amplification technique would amplify a sample up to a microgram level while maintaining the original sequence representation. Degenerate oligonucleotide-primed PCR (DOP), primer extension PCR technique (PEP) and multiple displacement amplification (MDA) are examples of whole genome amplification methods.

Non-limiting examples of information that can be gained from identifying polymorphisms in samples comprising mixtures of two genomes according to the methods of the invention include (i) determining the presence of two genomes that are derived from two subjects of the same species, e.g. fetal and maternal genomes, (ii) determining the presence of two genomes each derived from the same subject, and contributed by unaffected cells and cells that have undergone malignant transformations e.g. cancer, respectively, and (iii) determining the presence of two genomes derived from the same subject, and contributed to the sample by the subject and donor cells e.g. transplant patient.

Accordingly, the present invention can be used for applications, including, but not limited to, identifying polymorphisms in maternal samples for determining the presence or absence of a genetic disease in a fetus, identifying polymorphisms in a sample from an individual to determine the presence or absence of a disease e.g. cancer, and/or the status of the disease, and identifying polymorphisms in a sample from an individual to determine the presence or absence of graft versus host disease (GVHD). Additional uses of the method include identifying polymorphisms in mixed samples to determine the contribution of individuals in forensic analyses.

Differences in genomic sequences encompass polymorphisms including-without limitation single nucleotide polymorphisms (SNPs), tandem SNPs, small-scale multi-base deletions or insertions, called IN-DELS (also called deletion insertion polymorphisms or DIPs), Multi-Nucleotide Polymorphisms (MNPs) Short Tandem Repeats (STRs), restriction fragment length polymorphism (RFLP), deletions, including microdeletions, insertions, including microinsertions, duplications, inversions, translocations, multiplications, complex multi-site variants, copy number variations (CNV), and polymorphisms comprising any other change of sequence in a chromosome. In some embodiments, polymorphisms that are identified according to the method of the invention are SNPs and/or STRs. SNP polymorphisms can be single SNP, tandem SNPs. Single SNPs include individual SNPs, and tag SNPs i.e. SNPs present in a haplotype, and/or a haplotype block. Differences in genomic sequences include combinations of polymorphisms. For example, differences in genomic sequences can be detected by comparison of a combination of polymorphic sequences comprising one or more SNPs and one or more STRs. Any polymorphic site that can be encompassed by the reads generated by the sequencing methods described herein can be used to identify polymorphic sequences in samples comprising DNA of different genomes. Polymorphic sequences useful for practicing the methods of the invention are available from a variety of publicly accessible databases, which are continuously expanding. For example, useful databases include without limitation Human SNP Database at world wide web address wi.mit.edu, NCBI dbSNP Home Page at world wide web address ncbi.nlm.nih.gov, world wide web address lifesciences.perkinelmer.com, Celera Human SNP database at world wide web address celera.com, the SNP Database of the Genome Analysis Group (GAN) at world wide web address gan.iarc.fr, ATCC short tandem repeat (STR) database at world wide web address atcc.org, and the HapMap database at world wide web address hapmap.org.

Samples

Samples that are used for identifying polymorphisms in mixtures of two genomes comprise genomic DNA that is cellular or cell-free. Cellular DNA is derived from whole cells by manually or mechanically extracting the genomic DNA from whole cells of the same or of differing genetic compositions. Cellular DNA can be derived for example, from whole cells of the same genetic composition derived from one subject, from a mixture of whole cells of different subjects, or from a mixture of whole cells that differ in genetic composition that are derived from one subject. Methods for extracting genomic DNA from whole cells are known in the art, and differ depending upon the nature of the source. In some instances, it can be advantageous to fragment the cellular genomic DNA. Fragmentation can be random, or it can be specific, as achieved, for example, using restriction endonuclease digestion. Methods for random fragmentation are well known in the art, and include, for example, limited DNAse digestion, alkali treatment and physical shearing. In other embodiments, the sample nucleic acids are obtained as cellular genomic DNA, which is subjected to fragmentation into fragments of approximately 500 or more base pairs, and to which next generation sequencing (NGS) methods can be readily applied. In some embodiments, cellular genomic DNA is obtained to identify polymorphisms of a single genome. For example, cellular genomic DNA is obtained from a sample that contains only cells of the mother i.e. the sample is free of fetal genomic sequences. Identification of polymorphisms from a single genome e.g. maternal only genome, can be used in a comparison with polymorphisms identified in a mixture of fetal and maternal genomes to identify the fetal polymorphisms.

Cell-free DNA is genomic DNA that naturally occurs as a mixture of genomic fragments typically found in biological fluids e.g. blood, of a subject. The genomic mixture can be derived from cells that naturally rupture to release their genomic content by biological processes e.g. apoptosis. A sample of cfDNA can comprise cfDNA derived from a mixture of cells of different subjects of the same species, from a mixture of cells from one subject that differ in genetic composition, or from a mixture of cells from different species e.g. a subject. According to the method of the invention, DNA sequences of the genomes comprised in the mixture of cellular and/or cell-free DNA can be determined to identify the origin of the nucleic acids.

In some embodiments of the invention it is advantageous to obtain cell-free nucleic acids e.g. cell-free DNA (cfDNA). Cell-free nucleic acids, including cell-free DNA, can be obtained by various methods known in the art from biological samples including but not limited to plasma, serum and urine (Fan et al., Proc Natl Acad Sci 105:16266-16271 [2008]; Koide et al., Prenatal Diagnosis 25:604-607 [2005]; Chen et al., Nature Med. 2: 1033-1035 [1996]; Lo et al., Lancet 350: 485-487 [1997]; Botezatu et al., Clin Chem. 46: 1078-1084, 2000; and Su et al., J Mol. Diagn. 6: 101-107 [2004]). To separate cfDNA from cells, fractionation, centrifugation (e.g., density gradient centrifugation), DNA-specific precipitation, or high-throughput cell sorting and/or separation methods can be used. Commercially available kits for manual and automated separation of cfDNA are available (Roche Diagnostics, Indianapolis, Ind., Qiagen, Valencia, Calif., Macherey-Nagel, Duren, Del.).

The cfDNA present in the sample can be enriched specifically or non-specifically. Non-specific enrichment of sample DNA refers to the whole genome amplification of the genomic DNA fragments of the sample that can be used to increase the level of the sample DNA prior to identifying polymorphisms by NGS sequencing. Non-specific enrichment can be the selective enrichment of one of the two genomes present in the sample. For example, non-specific enrichment can be selective of the fetal genome in a maternal sample, which can be obtained by known methods to increase the relative proportion of fetal to maternal DNA in a sample. Alternatively, non-specific enrichment can be the non-selective amplification of both genomes present in the sample. For example, non-specific amplification can be of fetal and maternal DNA in a sample comprising a mixture of DNA from the fetal and maternal genomes. Methods for whole genome amplification are known in the art. Degenerate oligonucleotide-primed PCR (DOP), primer extension PCR technique (PEP) and multiple displacement amplification (MDA), are examples of whole genome amplification methods. In some embodiments, the sample comprising the mixture of cfDNA from different genomes is unenriched for cfDNA of the genomes present in the mixture. In other embodiments, the sample comprising the mixture of cfDNA from different genomes is non-specifically enriched for any one of the genomes present in the sample.

Specific enrichment refers to the enrichment of a genomic sample for specific sequences e.g. polymorphic target sequences, which are selected for amplification prior to sequencing the DNA sample. Polymorphic target nucleic acid sequences comprising e.g. STRs, can be selected, amplified and combined with the cellular or cell free DNA present in a mixture of genomes to simultaneously determine fetal fraction, and aneuploidy as provided in the examples. Whole genome sequencing for identifying polymorphisms associated with disorders as provided by the present method can be performed in conjunction with other prenatal diagnostic methods e.g. methods for determining aneuploidy. In some embodiments, the identification of polymorphisms according to the present method does not include specifically enriching polymorphic target sequences.

The sample comprising the mixture of nucleic acids to which the methods described herein are applied is a biological sample such as a tissue sample, a biological fluid sample, or a cell sample. In some embodiments, the mixture of nucleic acids is purified or isolated from the biological sample by any one of the known methods. A biological fluid sample includes, as non-limiting examples, blood, plasma, serum, sweat, tears, sputum, urine, sputum, ear flow, lymph, interstitial fluid, saliva, cerebrospinal fluid, ravages, bone marrow suspension, vaginal flow, transcervical lavage, brain fluid, ascites, milk, secretions of the respiratory, intestinal and genitourinary tracts, amniotic fluid and leukophoresis samples. In some embodiments, the sample is a sample that is easily obtainable by non-invasive procedures e.g. blood, plasma, serum, sweat, tears, sputum, urine, sputum, ear flow, and saliva. Preferably, the biological sample is a peripheral blood sample, or the plasma and serum fractions. In other embodiments, the biological sample is a swab or smear, a biopsy specimen, or a cell culture. In another embodiment, the sample is a mixture of two or more biological samples e.g. a biological sample can comprise two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In some embodiments, samples can be obtained from sources, including, but not limited to, samples from different individuals, different developmental stages of the same or different individuals, different diseased individuals (e.g., individuals with cancer or suspected of having a genetic disorder), normal individuals, samples obtained at different stages of a disease in an individual, samples obtained from an individual subjected to different treatments for a disease, samples from individuals subjected to different environmental factors, or individuals with predisposition to a pathology, individuals with exposure to a pathogen such as an infectious disease agent (e.g., HIV), and individuals who are recipients of donor cells, tissues and/or organs. In one embodiment, the sample is a maternal sample that is obtained from a pregnant female, for example a pregnant woman. In this instance, the sample can be analyzed using the methods described herein to provide a prenatal diagnosis of potential fetal disorders. Unless otherwise specified, a maternal sample comprises a mixture of fetal and maternal DNA e.g. cfDNA. In some embodiments, the maternal sample is a biological fluid sample e.g. blood sample. In other embodiments, the maternal sample is a purified cfDNA sample.

Samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue or cells.

Sequencing Methods

Differences in polymorphic sequences present in samples comprising a mixture of DNA e.g. cfDNA from two different genomes are identified by whole genome sequencing that employs next generation sequencing technologies (NGS) in which clonally amplified DNA templates or single DNA molecules are sequenced in a massively parallel fashion (e.g. as described in Volkerding et al. Clin Chem 55:641-658 [2009]; Metzker M Nature Rev 11:31-46 [2010]). In addition to high-throughput sequence information, NGS provides digital quantitative information, in that each sequence read is a countable "sequence tag" representing an individual clonal DNA template or a single DNA molecule. The sequencing technologies of NGS include pyrosequencing, sequencing-by-synthesis with reversible dye terminators, sequencing by oligonucleotide probe ligation and real time sequencing.

Some of the sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies are encompassed by the method of the invention and include the SMRT™ technology of Pacific Biosciences, the Ion Torrent™ technology, and nanopore sequencing being developed for example, by Oxford Nanopore Technologies.

While the automated Sanger method is considered as a 'first generation' technology, Sanger sequencing including the automated Sanger sequencing, can also be employed by the method of the invention. Additional sequencing methods that comprise the use of developing nucleic acid imaging technologies e.g. atomic force microscopy (AFM) or transmission electron microscopy (TEM), are also encompassed by the method of the invention. Exemplary sequencing technologies are described below.

In one embodiment, the DNA sequencing technology that is used in the method of the invention is the Helicos True Single Molecule Sequencing (tSMS) (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes PCR-based amplification in the preparation of the sequencing libraries, and the directness of sample preparation allows for direct measurement of the sample, rather than measurement of copies of that sample.

In one embodiment, the DNA sequencing technology that is used in the method of the invention is the 454 sequencing (Roche) (e.g. as described in Margulies, M. et al. Nature 437:376-380 [2005]). 454 sequencing involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is discerned and analyzed.

In one embodiment, the DNA sequencing technology that is used in the method of the invention is the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In one embodiment, the DNA sequencing technology that is used in the method of the invention is the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength identifiers (ZMW identifiers) that obtain sequence information while phospholinked nucleotides are being incorporated into the growing primer strand. A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Identification of the corresponding fluorescence of the dye indicates which base was incorporated. The process is repeated.

In one embodiment, the DNA sequencing technology that is used in the method of the invention is nanopore sequencing (e.g. as described in Soni G V and Meller A. Clin Chem 53: 1996-2001 [2007]). Nanopore sequencing DNA analysis techniques are being industrially developed by a number of companies, including Oxford Nanopore Technologies (Oxford, United Kingdom). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence.

In one embodiment, the DNA sequencing technology that is used in the method of the invention is the chemical-sensitive field effect transistor (chemFET) array (e.g., as described in U.S. Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In one embodiment, the DNA sequencing technology that is used in the method of the invention is the Halcyon Molecular's method that uses transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In one embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be identified by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct identification allows recordation of nucleotide incorporation in seconds.

In one embodiment, the method employs massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA e.g. cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments of <300 bp, and maternal cfDNA has been estimated to circulate as fragments of between about 0.5 and 1 Kb (Li et al., Clin Chem, 50: 1002-1011 [2004]). Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing ~1,000 copies of the same template. In one embodiment, the randomly fragmented genomic DNA e.g. cfDNA, is amplified using PCR before it is subjected to cluster amplification. Alternatively, an amplification-free genomic library preparation is used, and the randomly fragmented genomic DNA e.g. cfDNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence identification is achieved using laser excitation and total internal reflection optics. Short sequence reads of about 20-40 bp e.g. 36 bp, are aligned against a repeat-masked reference genome and genetic differences are called using specially developed data analysis pipeline software. After completion of the first read, the templates can be regenerated in situ to enable a second read from the opposite end of the fragments. Thus, either single-end or paired end sequencing of the DNA fragments is used according to the method. Partial sequencing of DNA fragments present in the sample is performed, and sequence tags comprising reads of predetermined length e.g. 36 bp, are mapped to a known reference genome. In some embodiments, the mapped tags are counted.

The length of the sequence read is associated with the particular sequencing technology. NGS methods provide sequence reads that vary in size from tens to hundreds of base pairs. In some embodiments of the method described herein, the sequence reads are about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the sequence reads are 36 bp. Other sequencing methods that can be employed by the method of the invention include the single molecule sequencing methods that can sequence nucleic acids molecules >5000 bp. The massive quantity of sequence output is transferred by an analysis pipeline that transforms primary imaging output from the sequencer into strings of bases. A package of integrated algorithms performs the core primary data transformation steps: image analysis, intensity scoring, base calling, and alignment.

In one embodiment, partial sequencing of DNA fragments present in the sample is performed, and sequence tags comprising reads of predetermined length e.g. 36 bp, are mapped to a known reference genome. In another embodiment, the mapped tags are counted. Only sequence reads that uniquely align to the reference genome are counted as sequence tags. In one embodiment, the reference genome is the human reference genome NCBI36/hg18 sequence, which is available on the world wide web at genome.ucsc.edu/cgi-bin/hgGateway?org=Human&db=hg18&hgsid=166260105). Other sources of public sequence information include GenBank, dbEST, dbSTS, EMBL (the European Molecular Biology Laboratory), and the DDBJ (the DNA Databank of Japan). In another embodiment, the reference genome comprises the human reference genome NCBI36/hg18 sequence and/or an artificial target sequences genome, which consists of polymorphic target sequences e.g. a SNP genome consisting of polymorphic sequences known to be associated with a disorder. In yet another embodiment, the reference genome is an artificial target sequence genome comprising polymorphic target sequences e.g. SNP sequences consisting of polymorphic sequences known to be associated with a disorder.

Mapping of the sequence tags is achieved by comparing the sequence of the tag with the sequence of the reference genome to determine the chromosomal origin of the sequenced nucleic acid (e.g. cfDNA) molecule, and specific genetic sequence information is not needed. A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, Calif., USA). In one embodiment, one end of the clonally expanded copies of the plasma cfDNA molecules is sequenced and processed by bioinformatic alignment analysis for the Illumina Genome Analyzer, which uses the Efficient Large-Scale Alignment of Nucleotide Databases (ELAND) software. Analysis of sequencing information for the identification of polymorphic sequences may allow for a small degree of mismatch (0-2 mismatches per sequence tag) to account for minor polymorphisms that may exist between the reference genome and the genomes in the mixed sample. Analysis of sequencing information for the determination of fetal fraction may allow for a small degree of mismatch depending on the polymorphic sequence. For example, a small degree of mismatch may be allowed if the polymorphic sequence is an STR. In cases when the polymorphic sequence is a SNP, all sequence that match exactly to either of the two alleles at the SNP site are counted first and filtered from the remaining reads, for which a small degree of mismatch may be allowed.

Only sequence reads that uniquely align to a reference genome are counted as sequence tags. In one embodiment, the reference genome is an artificial target sequences genome that comprises the sequences of the polymorphic target nucleic acids e.g. SNPs. In one embodiment, the reference genome is an artificial SNP reference genome. In another r embodiment, the reference genome is an artificial STR reference genome. In yet another embodiment, the reference genome is an artificial tandem-STR reference genome. Artificial reference genomes can be compiled using the sequences of the target polymorphic nucleic acids. Artificial reference genomes can comprise polymorphic target sequence each comprising one or more different types of polymorphic sequences. For example, an artificial reference genome can comprise polymorphic sequences comprising SNP alleles and/or STRs.

Sequencing Library Preparation

Next-generation DNA sequencers, such as the 454-FLX (Roche; at web address 454.com), the SOLiD™3 (Applied Biosystems; at web address solid.appliedbiosystems.com), and the Genome Analyzer (Illumina; http://www.illumina.com/pages.ilmn?ID=204) have transformed the landscape of genetics through their ability to produce hundreds of megabases of sequence information in a single run.

Sequencing methods require the preparation of sequencing libraries. Sequencing library preparation involves the production of a random collection of adapter-modified DNA fragments, which are ready to be sequenced. Sequencing libraries of polynucleotides can be prepared from DNA or RNA, including equivalents, analogs of either DNA or cDNA, that is complementary or copy DNA produced from an RNA template, for example by the action of reverse transcriptase. The polynucleotides may originate in double-stranded DNA (dsDNA) form (e.g. genomic DNA fragments, PCR and amplification products) or polynucleotides that may have originated in single-stranded form, as DNA or RNA, and been converted to dsDNA form. By way of example, mRNA molecules may be copied into double-stranded cDNAs suitable for use in preparing a sequencing library. The precise sequence of the primary polynucleotide molecules is generally not material to the method of library preparation, and may be known or unknown. In one embodiment, the polynucleotide molecules are DNA molecules. More particularly, the polynucleotide molecules represent the entire genetic complement of an organism, and are genomic DNA molecules e.g. cfDNA molecules, which include both intron and exon sequence (coding sequence), as well as non-coding regulatory sequences such as promoter and enhancer sequences. Still yet more particularly, the primary polynucleotide molecules are human genomic DNA molecules e.g. cfDNA molecules present in peripheral blood of a pregnant subject. Preparation of sequencing libraries for some NGS sequencing platforms require that the polynucleotides be of a specific range of fragment sizes e.g. 0-1200 bp. Therefore, fragmentation of polynucleotides e.g. genomic DNA may be required. cfDNA exists as fragments of <300 base pairs. Therefore, fragmentation of cfDNA is not necessary for generating a sequencing library using cfDNA samples. Fragmentation of polynucleotide molecules by mechanical means e.g. nebulization, sonication and hydro-shear, results in fragments with a heterogeneous mix of blunt and 3'- and 5'-overhanging ends. Whether polynucleotides are forcibly fragmented or naturally exists as fragments, they are converted to blunt-ended DNA having 5-phosphates and 3'-hydroxyl.

Typically, the fragment ends are end-repaired i.e. blunt-ended using methods or kits known in the art. The blunt-ended fragments can be phosphorylated by enzymatic treatment, for example using polynucleotide kinase. In some embodiments, a single deoxynucleotide e.g. deoxyadenosine (A) is added to the 3'-ends of the polynucleotides, for example, by the activity of certain types of DNA polymerase such as Taq polymerase or Klenow exo minus polymerase. dA-tailed products are compatible with 'T' overhang present on the 3' terminus of each duplex region of adaptors to which they are ligated in a subsequent step. dA-tailing prevents self-ligation of both of the blunt-ended polynucleotide such that there is a bias towards formation of the adaptor-ligated sequences. The dA-tailed polynucleotides are ligated to double-stranded adaptor polynucleotides sequences. The same adaptor can be used for both ends of the polynucleotide, or two sets of adaptors can be utilized. Ligation methods are known in the art and utilize ligase enzymes such as DNA ligase to covalently link the adaptor to the d-A-tailed polynucleotide. The adaptor may contain a 5'-phosphate moiety to facilitate ligation to the target 3'-OH. The dA-tailed polynucleotide contains a 5'-phosphate moiety, either residual from the shearing process, or added using an enzymatic treatment step, and has been end repaired, and optionally extended by an overhanging base or bases, to give a 3'-OH suitable for ligation. The products of the ligation reaction are purified to remove unligated adaptors, adaptors that may have ligated to one another, and to select a size range of templates for cluster generation, which can be preceded by an amplification e.g. a PCR amplification. Purification of the ligation products can be obtained by methods including gel electrophoresis and solid-phase reversible immobilization (SPRI).

Standard protocols e.g. protocols for sequencing using, for example, the Illumina platform, instruct users to purify the end-repaired products prior to dA-tailing, and to purify the dA-tailing products prior to the adaptor-ligating steps of the library preparation. Purification of the end-repaired products and dA-tailed products remove enzymes, buffers, salts and the like to provide favorable reaction conditions for the subsequent enzymatic step. In one embodiment, the steps of end-repairing, dA-tailing and adaptor ligating exclude the purification steps. Thus, in one embodiment, the method of the invention encompasses preparing a sequencing library that comprises the consecutive steps of end-repairing, dA-tailing and adaptor-ligating (see pending U.S. patent application Ser. No. 12/958,353). In embodiments for preparing sequencing libraries that do not require the dA-tailing step, e.g. protocols for sequencing using Roche 454 and SOLID™3platforms, the steps of end-repairing and adaptor-ligating exclude the purification step of the end-repaired products prior to the adaptor-ligating.

In a next step of one embodiment of the method, an amplification reaction is prepared. The amplification step introduces to the adaptor ligated template molecules the oligonucleotide sequences required for hybridization to the flow cell. The contents of an amplification reaction are known by one skilled in the art and include appropriate substrates (such as dNTPs), enzymes (e.g. a DNA polymerase) and buffer components required for an amplification reaction. Optionally, amplification of adaptor-ligated polynucleotides can be omitted. Generally amplification reactions require at least two amplification primers i.e. primer oligonucleotides, which may be identical, and include an 'adaptor-specific portion', capable of annealing to a primer-binding sequence in the polynucleotide molecule to be amplified (or the complement thereof if the template is viewed as a single strand) during the annealing step. Once formed, the library of templates prepared according to the methods described above can be used for solid-phase nucleic acid amplification. The term 'solid-phase amplification' as used herein refers to any nucleic acid amplification reaction carried out on or in association with a solid support such that all or a portion of the amplified products are immobilized on the solid support as they are formed. In particular, the term encompasses solid-phase polymerase chain reaction (solid-phase PCR) and solid phase isothermal amplification which are reactions analogous to standard solution phase amplification, except that one or both of the forward and reverse amplification primers is/are immobilized on the solid support. Solid phase PCR covers systems such as emulsions, wherein one primer is anchored to a bead and the other is in free solution, and colony formation in solid phase gel matrices wherein one primer is anchored to the surface, and one is in free solution. Following amplification, and sequencing libraries can be analyzed by microfluidic capillary electrophoresis to ensure that the library is free of adaptor dimers or single stranded DNA. The library of template polynucleotide molecules is particularly suitable for use in solid phase sequencing methods. In addition to providing templates for solid-phase sequencing and solid-phase PCR, library templates provide templates for whole genome amplification.

In one embodiment, the library of adaptor-ligated polynucleotides is subjected to massively parallel sequencing, which includes techniques for sequencing millions of fragments of nucleic acids, e.g., using attachment of randomly fragmented genomic DNA to a planar, optically transparent surface and solid phase amplification to create a high density sequencing flow cell with millions of clusters. Clustered arrays can be prepared using either a process of thermocycling, as described in patent WO9844151, or a process whereby the temperature is maintained as a constant, and the cycles of extension and denaturing are performed using changes of reagents. The Solexa/Illumina method referred to herein relies on the attachment of randomly fragmented genomic DNA to a planar, optically transparent surface. Attached DNA fragments are extended and bridge amplified to create an ultra-high density sequencing flow cell with millions of clusters each containing thousands of copies of the same template (WO 00/18957 and WO 98/44151). The cluster templates are sequenced using a robust four-color DNA sequencing-by-synthesis technology that employs reversible terminators with removable fluorescent dyes. Alternatively, the library may be amplified on beads wherein each bead contains a forward and reverse amplification primer.

Sequencing of the amplified libraries can be carried out using any suitable sequencing technique as described herein. In one embodiment, sequencing is massively parallel sequencing using sequencing-by-synthesis with reversible dye terminators. In other embodiments, sequencing is massively parallel sequencing using sequencing-by-ligation. In other embodiments, sequencing is single molecule sequencing.

Identification of Polymorphisms by WGS

Polymorphisms present in the sample comprising a mixture of DNA from two genomes can be identified by WGS of at least a portion of the DNA molecules contained in the sample.

Prior to sequencing, the mixture of DNA e.g. purified mixture of fetal and maternal cfDNA, is modified to prepare a sequencing library to generate single-end sequence reads of between 20 and 40 bp e.g. 36 bp, which are aligned to a reference genome, e.g. hg18. In some embodiments, the sequence reads comprise about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130 bp, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the sequence reads comprise 36 bp. In another embodiment, paired-end sequencing is used. Paired-end sequencing is a simple modification of the single end read DNA library preparation that facilitates reading both the forward and reverse template strands of each cluster during one paired-end read. In addition to sequence information, both reads contain long range positional information. Sequence reads are aligned to a human reference genome, and the reads that are uniquely mapped to the human reference genome are identified as sequence tags. In one embodiment, at least about $3\times10^6$ qualified sequence tags, at least about $5\times10^6$ qualified sequence tags, at least about $8\times10^6$ qualified sequence tags, at least about $10\times10^6$ qualified sequence tags, at least about $15\times10^6$ qualified sequence tags, at least about $20\times10^6$ qualified sequence tags, at least about $30\times10^6$ qualified sequence tags, at least about $40\times10^6$ qualified sequence tags, at least about $50\times10^6$ qualified sequence tags, at least about $50\times10^6$ qualified sequence tags, at least about $60\times10^6$ qualified sequence tags, at least about $70\times10^6$ qualified sequence tags, at least about $80\times10^6$ qualified sequence tags, at least about $90\times10^6$ qualified sequence tags, at least about $100\times10^6$ qualified sequence tags, at least about $150\times10^6$ qualified sequence tags, at least about $200\times10^6$ qualified sequence tags, at least about $250\times10^6$ qualified sequence tags, at least about $300\times10^6$ qualified sequence tags, or more qualified sequence tags comprising between 20 and 40 bp reads are obtained from reads that map uniquely to a reference genome. The number of tags required to encompass an entire genome depends on the length of the reads. It is estimated that the human genome comprises at least 10 million SNPs. Therefore, a sufficient number of tags that encompass at least 10 million polymorphisms will need to be generated to identify polymorphisms using whole genome sequencing according to the present method.

Polymorphic sequences located at multiple polymorphic sites are identified by the sequences of the tags, and sequence differences at each of the multiple polymorphic sites (loci) can be analyzed to allocate the variant sequences to one of the two genomes from which the sequenced DNA is derived. Identification of the multiple polymorphic sequences is performed by aligning the sequence tags to multiple reference polymorphic sequences, which are known sequences that are available from various databases as described herein. For example, identification of polymorphic sequences comprising SNPs can be performed by comparing the sequences of the tags to the sequences of known SNPs provided in databases including, but not limited to Human SNP Database at world wide web wi.mit.edu, NCBI dbSNP Home Page at world wide web address ncbi.nlm.nih.gov, world wide web address life-sciences.perkinelmer.com, Celera Human SNP database at world wide web address celera.com, the SNP Database of the Genome Analysis Group (GAN) at world wide web address gan.iarc.fr. To identify tandem SNP sequences, the International HapMap Consortium database can be searched (The International HapMap Project, Nature 426:789-796 [2003]). The database is available on the world wide web at hapmap.org. Identification of polymorphic sequences comprising STRs can be performed by comparing the sequences of the tags to the sequences of known STRs provided for example in the ATCC short tandem repeat (STR) database at world wide web address atcc.org.

In one embodiment, the sample comprising the mixture of DNA molecules derived from two genomes is unenriched for polymorphic target sequences. In another embodiment, the sample comprising the mixture of DNA molecules derived from two different genomes is non-specifically enriched for the whole genome sequences prior to whole genome sequencing i.e. whole genome amplification is performed prior to sequencing.

In one embodiment, the method can be used for identifying multiple polymorphisms in a first genome present in a blood sample that comprises a mixture of cfDNA molecules contributed to the sample by two different genomes. For example, the blood sample is a maternal blood sample that comprises cfDNA molecules derived from the fetal and the maternal genomes. Preferably, the plasma fraction is obtained from the whole blood sample, and the cfDNA contained in the plasma fraction is purified using known methods prior to whole genome sequencing. In some embodiments, the purified cfDNA sample comprising the mixture of fetal and maternal cfDNA is unenriched for either the fetal or the maternal genome.

Enrichment of specific polymorphic sequences i.e. polymorphic target sequences can be performed for example, using sequence-specific primers to amplify polymorphic sequences of interest. In one embodiment, polymorphic sequences of interest include sequences known to be associated with a disorder. Polymorphic target sequences of interest include any one or a combination of the polymorphisms described herein. In one embodiment, the polymorphic target sequences of interest are associated with monogenic and/or polygenic disorders. In one embodiment, polymorphic sequences are specifically amplified in a maternal sample comprising a mixture of fetal and maternal cfDNA for identifying targeted polymorphic sequences that are associated with a disorder. In some embodiments, the polymorphic sequences are associated with a disorder in the fetus.

In one embodiment, identification of polymorphic sequences contributed by a first genome present in a sample comprising a mixture of two genomes is performed by determining the sequence at multiple polymorphic sites in a first sample containing DNA molecules derived essentially from only a second genome, determining the sequence at the corresponding multiple polymorphic sites in a second sample containing a mixture of DNA molecules derived from a first and a second genome, and comparing the polymorphic sequences determined in both samples thereby identifying multiple polymorphisms in a first genome of a sample comprising a mixture of two genomes. For example, identification of polymorphic sequences contributed by a fetal genome i.e. first genome, is performed by determining the sequence at multiple polymorphic sites in a maternal buffy coat sample i.e. a sample containing DNA molecules derived essentially from only a second genome, determining the sequence at the corresponding multiple polymorphic sites in a purified plasma sample i.e. a second sample containing a mixture of cfDNA molecules derived from the fetal and the maternal genomes, and comparing the polymorphic sequences determined in both samples to identify multiple fetal polymorphisms.

Figure 4:
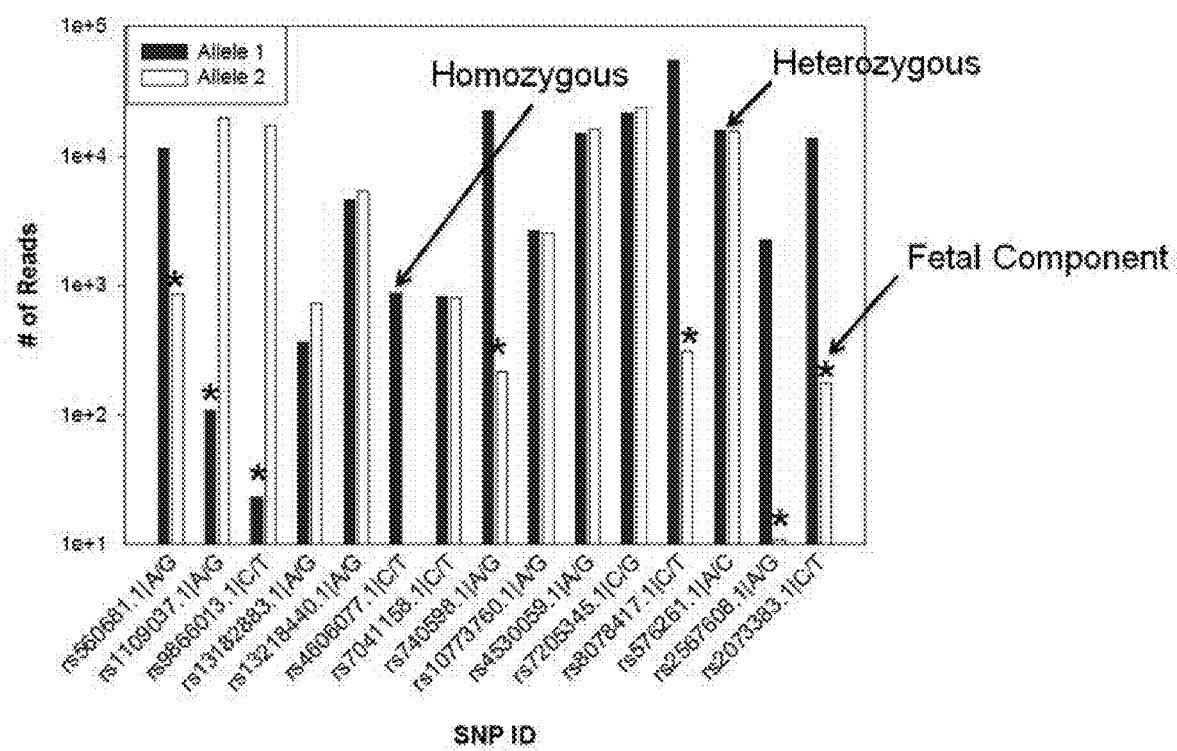
FIG. 4 is a bar diagram showing the identification of fetal and maternal polymorphic sequences (SNPs) used to determine fetal fraction in a test sample. The total number of sequence reads (Y-axis) mapped to the SNP sequences identified by rs numbers (X-axis), and the relative level of fetal nucleic acids (*) are shown.

In another embodiment, identification of polymorphic sequences contributed by the fetal genome to the mixture of fetal and maternal nucleic acids in a maternal sample can be performed without genotyping the maternal alleles in a maternal sample that is substantially free of fetal nucleic acids. Identification of the fetal polymorphic sequences can be made based on the identification and quantification of different sequences i.e. alleles, at multiple polymorphic sites. As is shown in Example 1, whole genome sequencing of a maternal plasma cfDNA sample comprising a mixture of fetal and maternal cfDNA molecules reveals that fetal polymorphic sequences e.g. SNPs, that are present in the maternal sample are present at a level that is proportional to the level of fetal cfDNA relative to that of the maternal cfDNA. In some embodiments, the method identifies multiple polymorphisms in a sample comprising a mixture of cfDNA of two genomes without specifically amplifying target polymorphic sequences of interest. In some embodiments, identification of polymorphic sequences can be performed in samples that are specifically enriched for target polymorphic sequences. Examples 6, 7, 8, and 9 show that the sequence tags that map to specific polymorphic sequences can be quantified, that the polymorphic sequences pertaining to the fetal and the maternal genomes can be identified, and that the relative level of fetal and maternal tags can be used to determine the fetal fraction. In particular, the relative contribution of a polymorphic allele derived from the fetal genome to the contribution of the corresponding polymorphic allele derived from the maternal genome is indicative of the origin of the sequence i.e. whether the polymorphic sequence is fetal or maternal in origin. Informative polymorphic sites e.g. SNP, are identified by the difference in the allelic sequences and the amount of each of the possible alleles. Fetal cfDNA is present at a concentration that can be up to about 30% of the maternal cfDNA (Liao et al., Clin Chem 57:1 [2011]). Thus, the presence of a minor contribution of an allele to the mixture of fetal and maternal nucleic acids relative to the major contribution of the maternal allele can be assigned to the fetus. Alleles that are derived from the maternal genome are herein referred to as major alleles, and alleles that are derived from the fetal genome are herein referred to as minor alleles. Alleles that are represented by similar levels of mapped sequence tags represent maternal alleles. FIG. 4 provides exemplary data showing that informative SNPs are discerned from the single nucleotide change at a polymorphic site, and fetal alleles are discerned by their relative minor contribution to the mixture of fetal and maternal nucleic acids in the sample when compared to the major contribution to the mixture by the maternal nucleic acids. The relative abundance of fetal cfDNA in the maternal sample can be determined as a parameter of the total number of unique sequence tags mapped to the target nucleic acid sequence on a reference genome for each of the two alleles of the predetermined polymorphic site. Quantification of informative polymorphisms e.g. SNPs, can be used to determine the fraction of fetal DNA in a mixture of fetal and maternal DNA. Similarly, quantification of informative polymorphic alleles can be used to determine the level of a first genome and a second genome in a sample comprising a mixture of the two genomes.

In one embodiment, the multiple polymorphic sites are located on chromosomes other than 21, 18, 13, or Y. In another embodiment, the multiple polymorphic sites are located on a plurality of different chromosomes.

In one embodiment, a paternal sample can be used to determine the presence or absence of a paternally-inherited fetal nucleic acid in a sample. The paternal sample can be, for example, a whole blood sample, a plasma sample, a serum sample, or a buffy coat sample. In another embodiment, a paternal sample is not used to determine the presence or absence of a paternally-inherited fetal nucleic acid in a sample. The sample can be enriched for specific sequences prior to genotyping.

In one embodiment, identification of polymorphic sequences in the mixture of fetal and maternal cfDNA molecules does not involve investigating the methylation status of nucleic acids in the sample. In another embodiment, identification of polymorphic sequences in the mixture of fetal and maternal cfDNA molecules does not involve use of Y-chromosome sequence.

The number of polymorphisms that can be genotyped in a sample can be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 200, 300, 400, 500, 600, 700, 800, 900, 1000 or more. For example, it is estimated that the human genome comprises at least about 10 million SNPs. Therefore, the number of polymorphisms that can be genotypes in a sample from a human subject can be at least about 10 million SNPs, as well as many other types of polymorphisms that are present in any one human genome. In some embodiments, identification of multiple polymorphisms in a first genome of a sample comprising a mixture of DNA e.g. cfDNA, of a first and a second genome is performed by whole genome sequencing using a NGS method as described herein. In some embodiments, the whole genome sequencing method is an NGS method that identifies the polymorphic sequences by massively parallel sequencing clonally amplified nucleic acid molecules or by massively parallel sequencing of single nucleic acid molecules i.e. single molecule sequencing.

Applications to Disorders

In one embodiment, the invention provides a method for determining the presence or absence of a number of disorders in a blood sample comprising a mixture of cfDNA of a first and a second genome. Determination of the presence or absence of multiple disorders comprises (a) whole genome sequencing at least a portion of the mixture of cfDNA to obtain a plurality of sequence tags; (b) determining in the plurality of sequence tags the presence or absence of multiple polymorphisms that are associated with the number of disorders, and (c) associating the multiple polymorphisms with the first and/or second genome in the mixture, wherein the mixture is unenriched for the multiple polymorphisms. Identification of the multiple polymorphisms in the mixture of cfDNA is performed by comparing the sequence of the mapped tags obtained by the whole genome sequencing method to multiple reference polymorphisms, as described herein. In one embodiment, the first genome is a fetal genome, and a second genome is a maternal genome. In another embodiment, the first genome is a genome of an unaffected cell and the second genome is a genome from an affected cell e.g. a cancer cell. In some embodiments, the affected and unaffected cells are derived from the same subject. For example, the affected cell can be a cell whose genome has been altered by a disorder. In some embodiments the disorder is a monogenic disorder. In other embodiments, the disorder is a polygenic disorder. Disorders can be identified by a single polymorphism e.g. a tag SNP, or by multiple polymorphisms present in a haplotype. In some embodiments, the multiple polymorphisms identified according to the present method are present in a haplotype block.

The disorders that can be identified by the present method are genetic disorders, which are illnesses caused at least in part by abnormalities in genes or chromosomes. Disorders identified by the present method include monogenic i.e. single gene, disorders and polygenic i.e. complex disorders. Single gene disorders include autosomal dominant, autosomal recessive, X-linked dominant, X-linked recessive, and Y-linked.

In autosomal dominant disorders, only one mutated copy of the gene will be necessary for a person to be affected by the disorder. Typically, an affected subject has one affected parent, and there is a 50% chance that the offspring will inherit the mutated gene. Conditions that are autosomal dominant sometimes have reduced penetrance, which means that although only one mutated copy is needed, not all individuals who inherit that mutation go on to develop the disease. Examples of autosomal dominant disorders that can be identified by the present method include without limitation familial hypercholesterolemia, hereditary spherocytosis, Marfan syndrome, neurofibromatosis type 1, hereditary nonpolyposis colorectal cancer, and hereditary multiple exostoses, and Huntington disease.

Autosomal recessive disorders detected by the present method include Sickle cell anemia, Cystic fibrosis, Tay-Sachs disease, Tay-Sachs disease, Mucopolysaccharidoses, Glycogen storage diseases, and Galactosemia. X-linked disorders detected by the present method include Duchenne muscular dystrophy and hemophilia. In autosomal recessive disorders, two copies of the gene must be mutated for a subject to be affected by an autosomal recessive disorder. An affected subject usually has unaffected parents who each carry a single copy of the mutated gene (and are referred to as carriers). Two unaffected people who each carry one copy of the mutated gene have a 25% chance with each pregnancy of having a child affected by the disorder. Examples of this type of disorder that can be identified by the present method include are cystic fibrosis, sickle-cell disease, Tay-Sachs disease, Niemann-Pick disease, spinal muscular atrophy, and Roberts syndrome. Certain other phenotypes, such as wet versus dry earwax, are also determined in an autosomal recessive fashion. X-linked dominant disorders are caused by mutations in genes on the X chromosome. Only a few disorders have this inheritance pattern, with a prime example being X-linked hypophosphatemic rickets. Males and females are both affected in these disorders, with males typically being more severely affected than females. Some X-linked dominant conditions such as Rett syndrome, incontinentia pigmenti type 2 and Aicardi syndrome are usually fatal in males, and are therefore predominantly seen in females. Exceptions to this finding are extremely rare cases in which boys with Klinefelter syndrome (47,XXY) also inherit an X-linked dominant condition and exhibit symptoms more similar to those of a female in terms of disease severity. The chance of passing on an X-linked dominant disorder differs between men and women. The sons of a man with an X-linked dominant disorder will all be unaffected (since they receive their father's Y chromosome), and his daughters will all inherit the condition. A woman with an X-linked dominant disorder has a 50% chance of having an affected fetus with each pregnancy, although it should be noted that in cases such as incontinentia pigmenti only female offspring are generally viable. In addition, although these conditions do not alter fertility per se, individuals with Rett syndrome or Aicardi syndrome rarely reproduce.

The present method can also be used to identify polymorphisms associated with X-linked disorders. X-linked recessive conditions are also caused by mutations in genes on the X chromosome. Males are more frequently affected than females, and the chance of passing on the disorder differs between men and women. The sons of a man with an X-linked recessive disorder will not be affected, and his daughters will carry one copy of the mutated gene. A woman who is a carrier of an X-linked recessive disorder ($X^R X^r$) has a 50% chance of having sons who are affected and a 50% chance of having daughters who carry one copy of the mutated gene and are therefore carriers. X-linked recessive conditions include without limitation the serious diseases Hemophilia A, Duchenne muscular dystrophy, and Lesch-Nyhan syndrome as well as common and less serious conditions such as male pattern baldness and red-green color blindness. X-linked recessive conditions can sometimes manifest in females due to skewed X-inactivation or monosomy X (Turner syndrome).

Y-linked disorders are caused by mutations on the Y chromosome. Because males inherit a Y chromosome from their fathers, every son of an affected father will be affected. Because females inherit an X chromosome from their fathers, female offspring of affected fathers are never affected. Since the Y chromosome is relatively small and contains very few genes, there are relatively few Y-linked disorders. Often the symptoms include infertility, which may be circumvented with the help of some fertility treatments. Examples are male infertility and hypertrichosis pinnae.

The present method can also be used to identify polymorphisms associated with genetic disorders that are complex, multifactorial, or polygenic, meaning that they are likely associated with the effects of multiple genes in combination with lifestyle and environmental factors. Multifactorial disorders include for example, heart disease and diabetes. Although complex disorders often cluster in families, they do not have a clear-cut pattern of inheritance. On a pedigree, polygenic diseases do tend to "run in families", but the inheritance does is not simple as is with Mendelian diseases. Strong environmental components are associated with many complex disorders e.g., blood pressure. The present method can be used to identify polymorphisms that are associated with polygenic disorders including but not limited to asthma, autoimmune diseases such as multiple sclerosis, cancers, ciliopathies, cleft palate, diabetes, heart disease, hypertension, inflammatory bowel disease, mental retardation, mood disorder, obesity, refractive error, and infertility. In some embodiments, the polymorphisms are SNPs. In other embodiments, the polymorphisms are STRs. In yet other embodiments, the polymorphisms are a combination of SNPs and STRs.

In one embodiment, identification of the polymorphic sequences associated with disorders comprises sequencing at least a portion of the cellular genome corresponding to the second genome in the mixture of cfDNA. Identification of polymorphic sequences contributed by a first genome is performed by determining the sequence at multiple polymorphic sites in a first sample containing DNA molecules derived essentially from only a second genome, determining the sequence at the corresponding multiple polymorphic sites in a second sample containing a mixture of DNA molecules derived from a first and a second genome, and comparing the polymorphic sequences determined in both samples thereby identifying multiple polymorphisms in a first genome of a sample comprising a mixture of two genomes. For example, identification of polymorphic sequences contributed by a fetal genome i.e. first genome, is performed by determining the sequence at multiple polymorphic sites in a maternal buffy coat sample i.e. a sample containing DNA molecules derived essentially from only a second genome, determining the sequence at the corresponding multiple polymorphic sites in a purified plasma sample i.e. a second sample containing a mixture of cfDNA molecules derived from the fetal and the maternal genomes, and comparing the polymorphic sequences determined in both samples to identify multiple fetal polymorphisms. In one embodiment, the first genome is a fetal genome, and a second genome is a maternal genome. In another embodiment, the first genome is a genome of an unaffected cell and the second genome is a genome from an affected cell. In some embodiments, the affected and unaffected cells are derived from the same subject. For example, the affected cell can be a cell whose genome has been altered by a disorder. In some embodiments the disorder is a monogenic disorder. In other embodiments, the disorder is a polygenic disorder. Disorders can be identified by a single polymorphism, or by multiple polymorphisms present in a haplotype. In some embodiments, the multiple polymorphisms identified according to the present method are present in a haplotype block.

In one embodiment, the present invention provides methods for detecting cancer in a patient, comprising: providing a sample from a patient comprising a mixture of genomes derived from normal i.e. unaffected, and cancerous i.e. affected, cells; and identifying multiple polymorphisms associated with cancer. In some embodiments, the sample is selected from blood, plasma, serum and urine. In some embodiments, the sample is a plasma sample. In other embodiments, the sample is a urine sample.

In one embodiment, identifying multiple polymorphisms associated with cancer comprises enriching the DNA in the sample for polymorphic target sequences. In other embodiments, enrichment of the sample for polymorphic target sequences is not performed. In some embodiments, identifying multiple polymorphisms associated with cancer comprises quantifying the number of copies of the polymorphic sequence.

Cancers that can be identified and/or monitored according to the method of the invention include solid tumors, as well as, hematologic tumors and/or malignancies. Various cancers to be treated include sarcomas, carcinomas, and adenocarcinomas not limited to breast cancer, lung cancer, colorectal cancer, pancreatic cancer, ovarian cancer, prostate cancer, renal carcinoma, hepatoma, brain cancer, melanoma, multiple myeloma, lymphoma, Hodgkin's lymphoma, non-Hodgkin's lymphoma, childhood lymphomas, and lymphomas of lymphocytic and cutaneous origin, leukemia, childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia, myeloid neoplasms, mast cell neoplasms, hematologic tumor, and lymphoid tumor, including metastatic lesions in other tissues or organs distant from the primary tumor site.

The methods of the present invention are useful, for example, in diagnosing or determining a prognosis in a disease condition known to be associated with a specific haplotype(s), to determine novel haplotypes, and to detect haplotype associations with responsiveness to pharmaceuticals. The association of multiple polymorphic sequences with multiple disorders can be determined from the identity of a single polymorphic sequence for each of the multiple disorders. Alternatively, association of multiple polymorphic sequences with multiple disorders can be determined from the identity of multiple polymorphic sequences for each of the multiple disorders.

Conventional genotyping techniques have been limited to identifying polymorphisms in short genomic regions of a few kilobases, and identification of haplotypes has relied on family data and statistical estimation using computational algorithms. Whole genome sequencing enables the identification of haplotypes by directly identifying the polymorphisms on a genome. The identification of the haplotypes according to the method is not limited by the intervening distance between polymorphisms. In some embodiments, the method further comprises whole genome sequencing maternal cellular DNA. Maternal cellular DNA can be obtained from a biological sample devoid of fetal genomic DNA. For example, maternal DNA can be obtained from the buffy coat layer of a maternal blood. Haplotypes comprising a plurality of polymorphic sequences that span entire chromosomes can be determined according the present method. In one embodiment, the fetal haplotypes are compared to known disorder-associated haplotypes, and based on a match of the fetal haplotype with any one of the known disorder-associated haplotypes indicates that the fetus has the disorder or that the fetus is susceptible for the disorder. Fetal haplotypes can also be compared to haplotypes associated with treatment responsiveness or unresponsiveness of the specific polymorphism. Comparison of the identified fetal haplotypes to known haplotype databases allow for the diagnosis and/or prognosis of a disorder. Any biological sample comprising a mixture of fetal and maternal cfDNA can be used to determine the presence or absence of the fetal disorder. Preferably, the biological sample is selected from blood, or fractions thereof including plasma, or urine. In one embodiment, the biological sample is a blood sample. In another embodiment, the biological sample is a plasma sample. In yet another embodiment, the biological sample is a urine sample.

In one embodiment, the invention provides a method for determining the presence or absence of multiple fetal disorders, comprising (a) obtaining a maternal blood sample comprising a cell-free mixture of fetal and maternal DNA, (b) whole genome sequencing at least a portion of the cell-free mixture of fetal and maternal DNA, thereby obtaining a plurality of sequence tags; (c) determining multiple fetal polymorphisms in the sequence tags, and (d) determining the presence or absence of multiple fetal disorders. Examples of multiple fetal disorders that can be identified according to the present method include monogenic and polygenic disorders described herein.

In one embodiment, the invention provides a method for determining the presence or absence of multiple fetal disorders that comprises identifying multiple fetal polymorphisms associated with multiple disorders related haplotypes. In some embodiments, each of the haplotypes comprises at least at least two, at least three, at least four, at least five, at least ten or at least fifteen different tag polymorphisms. The tag polymorphisms present in the haplotype can be of the same type of polymorphism e.g. all tag SNP polymorphisms, or can be a combination of polymorphisms e.g. tag SNPs and tag deletions. In one embodiment, the polymorphisms are tag SNPs. In another embodiment, the polymorphisms are tag STRs. In yet another embodiment, the polymorphisms are a combination of tag SNPs and tag STRs. The tag polymorphisms can be in coding and/or non-coding regions of the genome. Identification of the polymorphisms is performed by whole genome sequencing using NGS technologies as described herein.

The invention provides a method for identifying copy number variations (CNV) as polymorphisms of a sequence of interest in a test sample that comprises a mixture of nucleic acids derived from two different genomes, and which are known or are suspected to differ in the amount of one or more sequence of interest. Copy number variations determined by the method of the invention include gains or losses of entire chromosomes, alterations involving very large chromosomal segments that are microscopically visible, and an abundance of sub-microscopic copy number variation of DNA segments ranging from kilobases (kb) to megabases (Mb) in size.

CNV in the human genome significantly influence human diversity and predisposition to disease (Redon et al., Nature 23:444-454 [2006], Shaikh et al. Genome Res 19:1682-1690 [2009]). CNVs have been known to contribute to genetic disease through different mechanisms, resulting in either imbalance of gene dosage or gene disruption in most cases. In addition to their direct correlation with genetic disorders, CNVs are known to mediate phenotypic changes that can be deleterious. Recently, several studies have reported an increased burden of rare or de novo CNVs in complex disorders such as Autism, ADHD, and schizophrenia as compared to normal controls, highlighting the potential pathogenicity of rare or unique CNVs (Sebat et al., 316: 445-449 [2007]; Walsh et al., Science 320:539-543 [2008]). CNV arise from genomic rearrangements, primarily owing to deletion, duplication, insertion, and unbalanced translocation events.

Embodiments of the invention provide for a method to assess copy number variation of a sequence of interest e.g. a clinically-relevant sequence, in a test sample that comprises a mixture of nucleic acids derived from two different genomes, and which are known or are suspected to differ in the amount of one or more sequence of interest. The mixture of nucleic acids is derived from two or more types of cells. In one embodiment, the mixture of nucleic acids is derived from normal and cancerous cells derived from a subject suffering from a medical condition e.g. cancer.

It is believed that many solid tumors, such as breast cancer, progress from initiation to metastasis through the accumulation of several genetic aberrations. [Sato et al., Cancer Res., 50: 7184-7189 [1990]; Jongsma et al., J Clin Pathol: Mol Path 55:305-309 [2002])]. Such genetic aberrations, as they accumulate, may confer proliferative advantages, genetic instability and the attendant ability to evolve drug resistance rapidly, and enhanced angiogenesis, proteolysis and metastasis. The genetic aberrations may affect either recessive "tumor suppressor genes" or dominantly acting oncogenes. Deletions and recombination leading to loss of heterozygosity (LOH) are believed to play a major role in tumor progression by uncovering mutated tumor suppressor alleles.

cfDNA has been found in the circulation of patients diagnosed with malignancies including but not limited to lung cancer (Pathak et al. Clin Chem 52:1833-1842 [2006]), prostate cancer (Schwartzenbach et al. Clin Cancer Res 15:1032-8 [2009]), and breast cancer (Schwartzenbach et al. available online at breast-cancer-research.com/content/11/5/R71 [2009]). Identification of genomic instabilities associated with cancers that can be determined in the circulating cfDNA in cancer patients is a potential diagnostic and prognostic tool. In one embodiment, the method of the invention assesses CNV of a sequence of interest in a sample comprising a mixture of nucleic acids derived from a subject that is suspected or is known to have cancer e.g. carcinoma, sarcoma, lymphoma, leukemia, germ cell tumors and blastoma. In one embodiment, the sample is a plasma sample derived (processes) from peripheral blood and that comprises a mixture of cfDNA derived from normal and cancerous cells. In another embodiment, the biological sample that is needed to determine whether a CNV is present is derived from a mixture of cancerous and non-cancerous cells from other biological fluids including but not limited to serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples, or in tissue biopsies, swabs or smears.

The sequence of interest is a nucleic acid sequence that is known or is suspected to play a role in the development and/or progression of the cancer. Examples of a sequence of interest include nucleic acids sequences that are amplified or deleted in cancerous cells as described in the following.

Dominantly acting genes associated with human solid tumors typically exert their effect by overexpression or altered expression. Gene amplification is a common mechanism leading to upregulation of gene expression. Evidence from cytogenetic studies indicates that significant amplification occurs in over 50% of human breast cancers. Most notably, the amplification of the proto-oncogene human epidermal growth factor receptor 2 (HER2) located on chromosome 17 (17(17q21-q22)), results in overexpression of HER2 receptors on the cell surface leading to excessive and dysregulated signaling in breast cancer and other malignancies (Park et al., Clinical Breast Cancer 8:392-401 [2008]). A variety of oncogenes have been found to be amplified in other human malignancies. Examples of the amplification of cellular oncogenes in human tumors include amplifications of: c-myc in promyelocytic leukemia cell line HL60, and in small-cell lung carcinoma cell lines, N-myc in primary neuroblastomas (stages III and IV), neuroblastoma cell lines, retinoblastoma cell line and primary tumors, and small-cell lung carcinoma lines and tumors, L-myc in small-cell lung carcinoma cell lines and tumors, c-myb in acute myeloid leukemia and in colon carcinoma cell lines, c-erbb in epidermoid carcinoma cell, and primary gliomas, c-K-ras-2 in primary carcinomas of lung, colon, bladder, and rectum, N-ras in mammary carcinoma cell line (Varmus H., Ann Rev Genetics 18: 553-612 (1984) [cited in Watson et al., Molecular Biology of the Gene (4th ed.; Benjamin/Cummings Publishing Co. 1987)].

Chromosomal deletions involving tumor suppressor genes may play an important role in the development and progression of solid tumors. The retinoblastoma tumor suppressor gene (Rb-1), located in chromosome 13q14, is the most extensively characterized tumor suppressor gene. The Rb-1 gene product, a 105 kDa nuclear phosphoprotein, apparently plays an important role in cell cycle regulation (Howe et al., Proc Natl Acad Sci (USA) 87:5883-5887 [1990]). Altered or lost expression of the Rb protein is caused by inactivation of both gene alleles either through a point mutation or a chromosomal deletion. Rb-i gene alterations have been found to be present not only in retinoblastomas but also in other malignancies such as osteosarcomas, small cell lung cancer (Rygaard et al., Cancer Res 50: 5312-5317 [1990)]) and breast cancer. Restriction fragment length polymorphism (RFLP) studies have indicated that such tumor types have frequently lost heterozygosity at 13q suggesting that one of the Rb-1 gene alleles has been lost due to a gross chromosomal deletion (Bowcock et al., Am J Hum Genet, 46: 12 [1990]). Chromosome 1 abnormalities including duplications, deletions and unbalanced translocations involving chromosome 6 and other partner chromosomes indicate that regions of chromosome 1, in particular 1q21-1q32 and 1p11-13, might harbor oncogenes or tumor suppressor genes that are pathogenetically relevant to both chronic and advanced phases of myeloproliferative neoplasms (Caramazza et al., Eur J Hematol 84:191-200 [2010]). Myeloproliferative neoplasms are also associated with deletions of chromosome 5. Complete loss or interstitial deletions of chromosome 5 are the most common karyotypic abnormality in myelodysplastic syndromes (MDSs). Isolated del(5q)/5q-MDS patients have a more favorable prognosis than those with additional karyotypic defects, who tend to develop myeloproliferative neoplasms (MPNs) and acute myeloid leukemia. The frequency of unbalanced chromosome 5 deletions has led to the idea that 5q harbors one or more tumor-suppressor genes that have fundamental roles in the growth control of hematopoietic stem/progenitor cells (HSCs/HPCs). Cytogenetic mapping of commonly deleted regions (CDRs) centered on 5q31 and 5q32 identified candidate tumor-suppressor genes, including the ribosomal subunit RPS14, the transcription factor Egrl/Krox20 and the cytoskeletal remodeling protein, alpha-catenin (Eisenmann et al., Oncogene 28:3429-3441 [2009]). Cytogenetic and allelotyping studies of fresh tumours and tumour cell lines have shown that allelic loss from several distinct regions on chromosome 3p, including 3p25, 3p21-22, 3p21.3, 3p12-13 and 3p14, are the earliest and most frequent genomic abnormalities involved in a wide spectrum of major epithelial cancers of lung, breast, kidney, head and neck, ovary, cervix, colon, pancreas, esophagous, bladder and other organs. Several tumor suppressor genes have been mapped to the chromosome 3p region, and are thought that interstitial deletions or promoter hypermethylation precede the loss of the 3p or the entire chromosome 3 in the development of carcinomas (Angeloni D., Briefings Functional Genomics 6:19-39 [2007]).

Newborns and children with Down syndrome (DS) often present with congenital transient leukemia and have an increased risk of acute myeloid leukemia and acute lymphoblastic leukemia. Chromosome 21, harboring about 300 genes, may be involved in numerous structural aberrations, e.g., translocations, deletions, and amplifications, in leukemias, lymphomas, and solid tumors. Moreover, genes located on chromosome 21 have been identified that play an important role in tumorigenesis. Somatic numerical as well as structural chromosome 21 aberrations are associated with leukemias, and specific genes including RUNX1, TMPRSS2, and TFF, which are located in 21q, play a role in tumorigenesis (Fonatsch C Gene Chromosomes Cancer 49:497-508 [2010]).

In one embodiment, the method provides a means to assess the association between gene amplification and the extent of tumor evolution. Correlation between amplification and/or deletion and stage or grade of a cancer may be prognostically important because such information may contribute to the definition of a genetically based tumor grade that would better predict the future course of disease with more advanced tumors having the worst prognosis. In addition, information about early amplification and/or deletion events may be useful in associating those events as predictors of subsequent disease progression. Gene amplification and deletions as identified by the method can be associated with other known parameters such as tumor grade, histology, Brd/Urd labeling index, hormonal status, nodal involvement, tumor size, survival duration and other tumor properties available from epidemiological and biostatistical studies. For example, tumor DNA to be tested by the method could include atypical hyperplasia, ductal carcinoma in situ, stage I-III cancer and metastatic lymph nodes in order to permit the identification of associations between amplifications and deletions and stage. The associations made may make possible effective therapeutic intervention. For example, consistently amplified regions may contain an overexpressed gene, the product of which may be able to be attacked therapeutically (for example, the growth factor receptor tyrosine kinase, $p185^{HER2}$).

The method can be used to identify amplification and/or deletion events that are associated with drug resistance by determining the copy number variation of nucleic acids from primary cancers to those of cells that have metastasized to other sites. If gene amplification and/or deletion is a manifestation of karyotypic instability that allows rapid development of drug resistance, more amplification and/or deletion in primary tumors from chemoresistant patients than in tumors in chemosensitive patients would be expected. For example, if amplification of specific genes is responsible for the development of drug resistance, regions surrounding those genes would be expected to be amplified consistently in tumor cells from pleural effusions of chemoresistant patients but not in the primary tumors. Discovery of associations between gene amplification and/or deletion and the development of drug resistance may allow the identification of patients that will or will not benefit from adjuvant therapy.

In other embodiments, the present method can be used to identify polymorphisms associated with trinucleotide repeat disorders, which are a set of genetic disorders caused by trinucleotide repeat expansion. Trinucleotide expansions are a subset of unstable microsatellite repeats that occur throughout all genomic sequences. If the repeat is present in a healthy gene, a dynamic mutation may increase the repeat count and result in a defective gene. In one embodiment, the method can be used to identify trinucleotide repeats associated with fragile X syndrome. The long arm of the X chromosome of patients suffering from fragile X syndrome can contain from 230 to 4000 CGG, as compared with 60 to 230 repeats in carriers and 5 to 54 repeats in unaffected individuals. The chromosomal instability resulting from this trinucleotide expansion presents clinically as mental retardation, distinctive facial features, and macroorchidism in males. The second, related DNA-triplet repeat disease, fragile X-E syndrome, was also identified on the X chromosome, but was found to be the result of an expanded CCG repeat. The present method can identify trinucleotide repeats associated with other repeat expansion disorders including Categories I, II and III. Category I disorders include Huntington's disease (HD) and the spinocerebellar ataxias that are caused by a CAG repeat expansion in protein-coding portions of specific genes. Category II expansions tend to be more phenotypically diverse with heterogeneous expansions that are generally small in magnitude, but also found in the exons of genes. Category III includes fragile X syndrome, myotonic dystrophy, two of the spinocerebellar ataxias, juvenile myoclonic epilepsy and friereich's ataxia. These diseases are characterized by typically much larger repeat expansions than the first two groups, and the repeats are located outside of the protein-coding regions of the genes.

In other embodiments, the present method can identify CAG trinucleotide repeats associated with at least ten neurologic disorders known to be caused by an increased number of CAG repeats, typically in coding regions of otherwise unrelated proteins. During protein synthesis, the expanded CAG repeats are translated into a series of uninterrupted glutamine residues forming what is known as a polyglutamine tract ("polyQ"). Such polyglutamine tracts may be subject to increased aggregation. These disorders are characterized by autosomal dominant mode of inheritance (with the exception of spino-bulbar muscular atrophy which shows X-linked inheritance), midlife onset, a progressive course, and a correlation of the number of CAG repeats with the severity of disease and the age at onset. Causative genes are widely expressed in all of the known polyglutamine diseases. A common symptom of PolyQ diseases is characterized by a progressive degeneration of nerve cells usually affecting people later in life. Although these diseases share the same repeated codon (CAG) and some symptoms, the repeats for the different polyglutamine diseases occur on different chromosomes. Examples of polyQ disorders that can be identified by the present method include without limitation DRPLA (Dentatorubropallidoluysian atrophy), HD (Huntington's disease), SBMA (Spinobulbar muscular atrophy or Kennedy disease), SCA1 (Spinocerebellar ataxia Type 1), SCA2 (Spinocerebellar ataxia Type 2), SCA3 (Spinocerebellar ataxia Type 3 or Machado-Joseph disease), SCA6 (Spinocerebellar ataxia Type 6), SCAT (Spinocerebellar ataxia Type 7), SCA17 (Spinocerebellar ataxia Type 17). Examples of non-polyQ disorders that can be identified by the present method include FRAXA (Fragile X syndrome), FXTAS (Fragile X-associated tremor/ataxia syndrome), FRAXE (Fragile XE mental retardation), FRDA (Friedreich's ataxia), DM (Myotonic dystrophy), SCA8 (Spinocerebellar ataxia Type 8), SCA12 (Spinocerebellar ataxia Type 12).

The present method used for identifying polymorphisms associated with multiple can be determined can be used in conjunction with methods for the determination of aneuploidy such as the methods described in U.S. Patent Application Publication Nos. US 2007/0202525A1; US2010/0112575A1, US 2009/0087847A1; US2009/0029377A1; US 2008/0220422A1; US2008/0138809A1, US2008/0153090A1, US2010/0138165, US 2010/0112590, U.S. Pat. No. 7,645,576, Fan et al., PNAS105:16266-16271 [2008]; Chiu et al. PNAS105:20458-20463 [2008]; Chiu et al., BMJ 2011; 342:c7401 [2011]; and pending U.S. patent application Ser. Nos. 12/958,352 "Method for Determining Copy Number Variations", and 12/958,353 "Sequencing Method sand Compositions for Prenatal Diagnoses", which are herein incorporated by reference in their entirety. The method can also be combined with assays for determining other prenatal conditions associated with the mother and/or the fetus. For example, the method can be used in conjunction with prenatal analyses, for example, as described in U.S. Patent Application Publication Nos. US2010/0112590A1, US2009/0162842A1, US2007/0207466A1, and US2001/0051341A1, all of which are incorporated by reference in their entirety.

The present invention is described in further detail in the following Examples which are not in any way intended to limit the scope of the invention as claimed. The attached Figures are meant to be considered as integral parts of the specification and description of the invention. The following examples are offered to illustrate, but not to limit the claimed invention.

EXAMPLES

Example 1

Plasma Cell-free DNA Comprises an Entire Genome

To demonstrate that plasma cfDNA comprises sequences that cover the entire human genome, experimental information obtained from sequencing cfDNA from maternal plasma samples was compared to the expected percent genome covered by a given number of sequence tags of a given tag length.

Experimental data: experimental determination of genome coverage by sequencing cfDNA from maternal plasma. The percent genome coverage was determined experimentally by sequencing cfDNA that was purified from the plasma fraction of a peripheral blood sample from 24 women each pregnant with an unaffected fetus identified as karyotypically normal (either 46, XX or 46, XY). DNA was extracted from plasma of peripheral blood samples using the QIAamp DNA Mini kit (Qiagen) with modifications to the manufacturer's instruction. 4.5 ml-5 ml of cell-free plasma was transferred into a 50 mL conical tube. PBS was added to bring the sample to 5 mL total volume, and the sample was treated with 500 µL Qiagen Protease solution. The sample was mixed and 5 mL Buffer AL was added to the sample solution. The sample was vortexed at 2500 RPM for 10 seconds, and incubated at 56° C. for 12 minutes. 5 mL 100% ethanol was added to the sample solution, and the solution was vortexed at 2500 RPM for 5 seconds. 590 µL aliquots of sample solution were transferred to each of 6 mini columns. The columns were centrifuged at 8,000 RPM for 30 seconds. The process was repeated three more times. On 4th and final spin, even out all column volumes were evened out, and the columns were spun for 1 minute. 500 µL wash AW1 was pipetted onto columns, and the columns were spun at 8,000 RPM for 1 minute. The columns were transferred toQiagen collection tubes, and washed with 500 µL of wash buffer by centrifugation at 14,000 RPM for 3 minutes. The columns were transferred to new clean Qiagen collection tubes, and centrifuged for an additional one minute. 55 µL of H2O or Elution Buffer (EB) was added to each of the columns, which were incubated at room temperature for 5 minutes. Purified cfDNA samples were eluted by centrifugation at 8,000 RPM for 2 minutes and stored at −80° C.

cfDNA was purified from plasma using reagents contained in the QIAamp DNA Mini kit (Qiagen) essentially according to the method used for extracting genomic DNA. 500 µL Qiagen Protease were added to 4.5 ml-5 ml of cell-free plasma, and mixed for 5 seconds. 5 mL Buffer AL were added to the sample solution, mixed for 10 seconds, and the mixture was incubated in sealed tubes 56° C. for 12 minutes. 5 mL 100% ethanol were added to the sample solution, the sample was mixed for 5 seconds, and 590 µL of sample solution was applied to each of 6 mini columns. The columns were centrifuged at 8,000 RPM for 30 seconds. Aliquots of the remaining sample solution were applied to the six mini columns as described. The columns were washed with 500 µL AW1, centrifuged at 8,000 RPM for 1 minute, transferred to a new Qiagen collection tube, washed with 500 µL of wash AW2, centrifuged at 14,000 RPM for 3 minutes, and again at 14,000 RPM for 1 minute. The columns were transferred to a sample collection tube. 55 µL of H2O or Elution Buffer (EB) was applied to the columns, and the columns were incubated at room temperature for 5 minutes before being centrifuged at 8,000 RPM for 2 minutes. The eluted samples were eluted and stored at −80° C. The purified cfDNA was sent to a service provider (Prognosis Biosciences, La Jolla, Calif.) for preparation of the sequencing libraries and for sequencing using the Illumina GAII (Illumina).

Image analysis of the sequencing information comprised in 36 bp reads was carried out at Prognosys Biosciences, utilizing the Integrated Primary Analysis and Reporting software (IPAR v1.3), and results were provided as the Data Folder portion of the Run Folder output (See Genome Analyzer Pipeline v1.3 and Consensus Assessment of Sequence and Variation (CASAVA) v1.0 Software User Guide from Illumina) The standard bustard.py script was used to generate base calls with the GERALD module to do sequence alignments to the reference human genome hg18. The 24 export.txt (aligned sequence tag) files each comprising about $5\times10^6$ tags were utilized as input into the (CASAVA) software package, treated as if they came from a single individual, and analyzed as a genome build while including examination of sequence differences between the combined sample and the reference genome sequence (in this case hg18). CASAVA provided coverage/depth statistics as well as SNP statistics for individual chromosomes.

Figure 2:
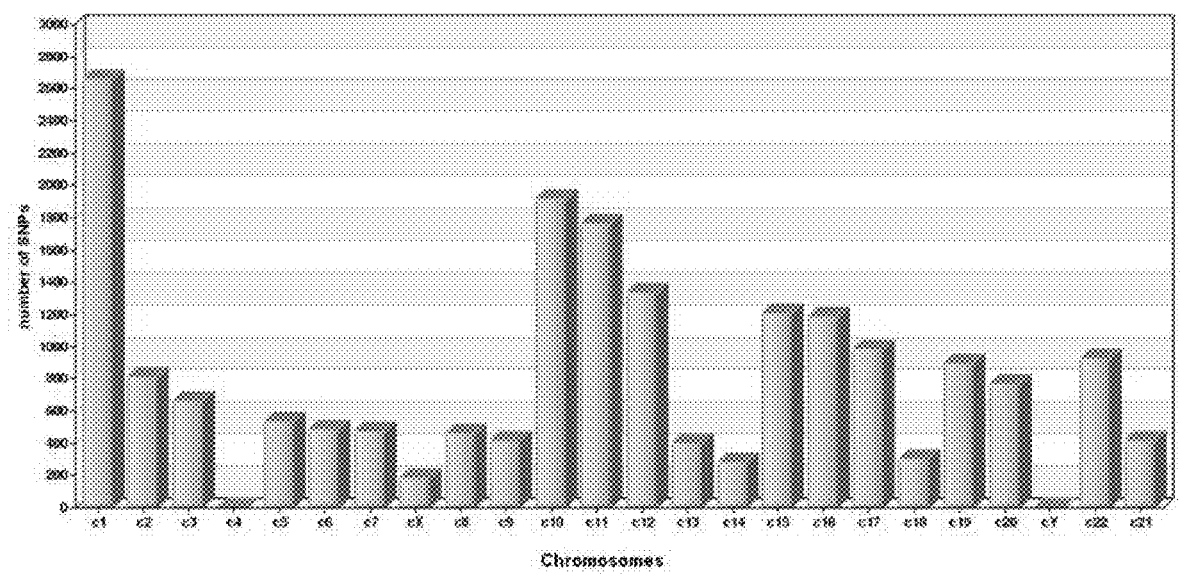
FIG. 2 shows the number of SNPs identified from the sequencing data shown in FIG. 1 that were mapped to each of the chromosomes. The SNPs that were counted were not differentiated between the maternal and fetal genome i.e. all counted SNPs had the same polymorphic sequence.

The relative coverage of individual chromosomes by the sequence tags is shown in FIG. 1 as a function of depth, wherein a maximum depth of 1 represents 100% coverage of each chromosome. FIG. 2 shows the number of SNPs that were identified and mapped to each of the chromosomes from the genome build (FIG. 1) compared to the reference sequences. The SNPs that were counted were not differentiated between the maternal and fetal genome i.e. all counted SNPs had the same polymorphic sequence.

Predicted Data: Predicted Genome Coverage of cfDNA in Maternal Plasma.

Given the limited genome coverage obtained from sequencing information of the 24 samples, we examined the experimental results in light of the theoretical expectation. Given a specified genome length, number of sequence tags (mapped chromosome reads), and tag length, the expected proportion (or percentage) of genome coverage was calculated by considering the probability density function for the binomial distribution $$f(k|n,p)=Pr(K=k)=\binom{n}{k}p^k(1-p)^{n-k}$$

where k is the number of tags at a given position, n is the number of tags mapped to the genome, and p is the probability of a tag mapping to a given position. Herein, we estimated that p=tag length/genome length.

Figure 3:
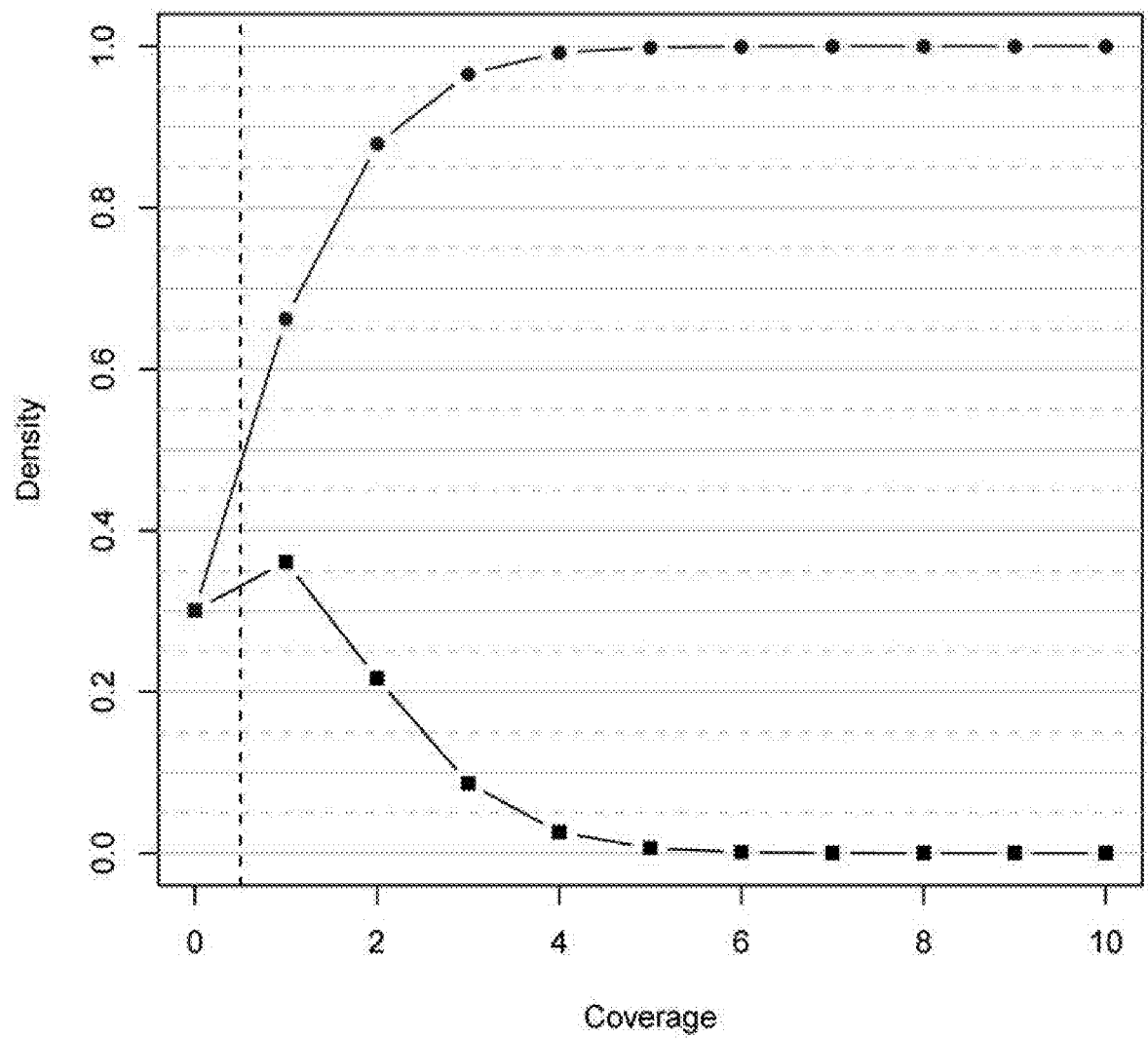
FIG. 3 shows the predicted genome coverage assuming the presence of at least one genome in the sample and using the whole genome sequencing data shown in FIG. 1. Cumulative (●) and incremental (■) genome coverage are shown.

Assuming the experimental conditions used in sequencing cfDNA in maternal plasma i.e. that each sequence tag is 30 bases; that $5\times10^6$ tags are obtained in a single sequencing event; that the total number of tags are determined from 24 sequencing events; and assuming that the entire genome of approximately $3\times10^9$ bases is present in the, the distribution of $(5\times10^6)(24)=1.2\times10^8$ tags across a single genome was analyzed and shown in FIG. 3.

FIG. 3 shows that approximately 30% of the genome is predicted not to be covered by at least one of the $1.2\times10^8$ tags, indicating that approximately 70% of the genome is expected to be mapped at least once. Approximately 95% of the mapped genome sites had a tag depth not greater than 3, indicating that most sites were covered by one, two, or three tags.

The percent genome coverage related to the tag depth i.e. the number of tags that mapped to the same site on the genome was tabulated as follows (Table 1), where the percent expected proportion of the genome that is covered per tag depth is (1—Expected Proportion of Genome Not Covered)×100.

TABLE 1

| Genome Tag Coverage | | |
|---|---|---|
| Coverage (tag depth) | Expected Proportion of Genome Not Covered | Expected Proportion of Genome Covered (%) |
| 0 | 0.301 | 69.9 |
| 1 | 0.361 | 63.9 |
| 2 | 0.217 | 78.3 |
| 3 | 0.087 | 91.3 |
| 4 | 0.026 | 97.4 |
| 5 | 0.006 | 99.4 |
| 6 | 0.001 | 99.9 |
| 7 | 0.000 | 100 |
| 8 | 0.000 | 100 |
| 9 | 0.000 | 100 |
| 10 | 0.000 | 100 |

The results show that genome coverage determined from the experimental results corresponds with that of the expected coverage, if the entire genome is available in the cfDNA sample. The result implies that even in experiments with limited coverage the cfDNA sample comprises sequences that span an entire human genome. In addition, the experimental data shows that polymorphisms e.g. SNPs can be identified by whole genome sequencing.

Having determined that polymorphisms can be identified in a sample comprising a mixture of fetal and maternal cfDNA, polymorphisms including SNPs and STRs were identified in maternal samples comprising fetal and maternal cfDNA for determining fetal fraction. Methods that use the identified polymorphisms for the simultaneous determination of fetal fraction and aneuploidy are provided below and in pending U.S. Patent Applications Pending U.S. patent application Ser. Nos. 12/958,347 entitled "Methods for Determining Fraction of Fetal Nucleic Acids in Maternal Samples"; 12/958,352 entitled "Method for Determining Copy Number Variations"; 12/958,356 entitled "Simultaneous Determination of Aneuploidy and Fetal Fraction", and 12/958,353 entitled "Methods and Compositions for Prenatal Diagnoses", all filed on Dec. 1, 2010, which are herein incorporated by reference in their entirety.

Example 2

Identification of SNPs by TaqMan Real-Time PCR in Maternal Samples Comprising a Mixture of Fetal and Maternal cfDNA: Use for Determining Fetal Fraction Having determined that polymorphisms can be identified in a sample comprising a mixture of fetal and maternal cfDNA, initial experiments were performed to identify informative SNPs by TaqMan Real-Time PCR in plasma samples of pregnant women, and for determining the fraction of fetal cfDNA.

Sample Processing and DNA Extraction

Peripheral blood drawn from each subject was collected in ACD tubes. One tube of blood sample (approximately 6-9 mL/tube) was transferred into one 15-mL low speed centrifuge tube. Blood was centrifuged at 2640 rpm, 4° C. for 10 min using Beckman Allegra 6 R centrifuge and rotor model GA 3.8. The buffy coat was collected and used as a source of genomic DNA. The upper plasma layer was collected and used for preparing cfDNA.

Genomic DNA was extracted from 1 ml of whole blood or buffy coat sample using QIAamp DNA Blood Mini kit (Qiagen) with modifications to the manufacturer's instructions as follows. One hundred μl of Qiagen Protease was added to 1 ml sample, and mixed for 10 seconds. One milliliter of Buffer AL was added to the sample, mixed for 20 seconds, and the mixture was incubated in sealed tubes at 56° C. for 10 minutes. One milliter of 100% ethanol was added to the sample solution, the sample was mixed for 15 seconds, and 620 µL of sample solution was applied to each of 2 mini columns. The columns were centrifuged at 8,000 RPM for 1 minute, washed with 500 µL AW1 solution, centrifuged at 8,000 RPM for 1 minute, transferred to a new Qiagen collection tube, washed with 500 µL of AW2, centrifuged once at 14,000 RPM for 3 minutes, and again at 14,000 RPM for 1 minute. The columns were transferred to sample collection tube. 200 µL of $H_2O$ was applied to the columns, and the columns were incubated at room temperature for 5 minutes before being centrifuged at 8,000 RPM for 2 minutes. The eluted samples were stored in one cryostorage tube at −80° C.

Cell-free DNA was extracted from cell-free plasma as described in Example 1.

Identification of Maternal and Fetal Genotype Using SNP Alleles by Taqman Real-Time PCR Analysis A SNP panel (Table 2, Pakstis et al., Hum Genet. 121: 305-317 [2007]) was used to determine the maternal and fetal SNP genotypes. TaqMan amplification reactions were set up in a reaction volume of 25 µl. Each reaction contained 1× TaqMan Universal PCR master mix, 0.9 µM forward and reverse primers and 0.2 µM probe, 1 ng of genomic DNA to determine the maternal genotypes or 0.3-1.5 ng of cell-free DNA to determine the fetal genotypes. Thermal cycling was 10 min at 95° C. and then 40 cycles of 95° C. for 15 seconds and 60° C. for 1 min. Amplification data was collected using 7500 Sequence Detector and then analyzed using the Sequence Detection System Software (Applied Biosystems).

SNPs present in maternal DNA were genotyped for the first 10 SNPs in the panel listed in Table 2. The maternal origin was verified by confirming the absence of an SRY (Sex-determination region on Y chromosome) allele. Subsequently, a sample of genotype matched cell-free DNA containing cell-free fetal DNA, was interrogated for the same 10 SNPs. Informative SNP alleles were detected, and used to determine the percentage of fetal fraction in the total cell-free DNA.

TABLE 2

SNP panel used for TaqMan real-time PCR genotyping

| SNP # | Assay ID | NCBI SNP Reference | Cytogenetic Band |
|---|---|---|---|
| 1 | C\_\_\_\_3032822\_1\_ | rs315791 | 5q35.1c |
| 2 | C\_\_\_\_2822618\_10 | rs3780962 | 10p13a |

TABLE 2-continued

SNP panel used for TaqMan real-time PCR genotyping

| SNP # | Assay ID | NCBI SNP Reference | Cytogenetic Band |
|---|---|---|---|
| 3 | C\_\_\_\_7538108\_10 | rs1410059 | 10q23.33d |
| 4 | C\_\_\_\_8263011\_10 | rs279844 | 4p12b |
| 5 | C\_\_\_\_3153696\_10 | rs338882 | 5q35.3d |
| 6 | C\_\_\_\_1371205\_10 | rs9951171 | 18p11.22b |
| 7 | C\_\_\_\_2515223\_10 | rs214955 | 6q25.2a |
| 8 | C\_\_\_25749280\_10 | rs6444724 | 3q29b |
| 9 | C\_\_\_\_\_411273\_10 | rs2503107 | 6q22.33a |
| 10 | C\_\_\_\_2572254\_10 | rs1019029 | 7p21.2a |
| 11 | C\_\_\_\_1732269\_10 | rs1413212 | 1q43f |
| 12 | C\_\_\_\_8953333\_10 | rs1031825 | 20p13a |
| 13 | C\_\_\_\_7539584\_10 | rs891700 | 1q43c |
| 14 | C\_\_\_\_2203431\_10 | rs1005533 | 20q12b |
| 15 | C\_\_\_\_2528441\_20 | rs2831700 | 21q21.3b |
| 16 | C\_\_\_\_3084646\_10 | rs354439 | 13q33.2b |
| 17 | C\_\_\_12098080\_10 | rs1979255 | 4q35.2d |
| 18 | C\_\_\_\_2120263\_10 | rs1454361 | 14q12a |
| 19 | C\_\_\_29375514\_10 | rs8037429 | 15q21.3a |
| 20 | C\_\_\_\_9630073\_10 | rs1490413 | 1p36.32b |

In Table 2 above, Assay ID number refers to SNPs that are commercially available through Applied Biosystems Assay ID. Context sequences are sequences that flank the 2 SNP alleles, which are written in bold and underlined. A dual-labeled fluorescent TaqMan probe for each SNP alleles was used. The 1st of the two alleles was labeled with VIC and the 2nd allele was labeled with FAM. Cytogenetic band refers to the chromosome locations of the SNPs. Forward and reverse primers, and labeled probes were synthesized by Applied Biosystems for each of the SNP sequences provided in Table 1 above.

SNP Genotyping of Maternal DNA

Maternal genotypes were determined for the 10 SNPs in the panel given in Table 2 above using TaqMan real-time PCR. All 10 SNPs were genotyped in genomic DNA extracted from buffy coat samples and whole blood samples, and the SRY allele was not detected in any of the samples (SRY %=0%), confirming that the origin of the alleles is maternal. These results demonstrate that maternal genotype can be determined from the genomic DNA extracted from whole blood or buffy coat.

SNP Genotyping of Fetal DNA

Fetal genotypes were determined for SNPs 1-10 in the panel of Table 2 above. All 10 SNPs were genotyped in cfDNA extracted from plasma samples as described above. Informative alleles were identified by comparing the genotypes determined in the cfDNA samples with the corresponding genotypes determined in the genomic DNA samples obtained from the pregnant subjects. The genotypes of 5 exemplary maternal and fetal alleles are given in Table 3 below. The informative fetal SNP alleles are highlighted and underlined.

TABLE 3

SNP genotypes identified in genomic and cfDNA samples

| Sample ID | | SNP1 | SNP2 | SNP3 | SNP4 | SNP5 | SNP6 | SNP7 | SNP8 | SNP9 | SNP10 |
|---|---|---|---|---|---|---|---|---|---|---|---|
| 24181 | Maternal (buffy coat) | A/A | G/G | C/T | A/T | A/G | A/G | C/T | C/T | A/C | G/G |
| | Fetal (cfDNA) | A/A | G/G | | | | | | | | A/G |
| 31205 | Maternal (buffy coat) | C/C | G/G | C/C | A/T | A/G | A/G | T/T | C/T | A/C | G/G |
| | Fetal (cfDNA) | C/C | | C/T | | | | | | | G/G |

TABLE 3-continued

SNP genotypes identified in genomic and cfDNA samples

| Sample ID | | SNP1 | SNP2 | SNP3 | SNP4 | SNP5 | SNP6 | SNP7 | SNP8 | SNP9 | SNP10 |
|---|---|---|---|---|---|---|---|---|---|---|---|
| 51212 | Maternal (buffy coat) | C/C | A/G | T/T | A/A | A/G | A/G | C/T | T/T | A/C | G/G |
| | Fetal (cfDNA) | C/C | | C/T | A/A | | | | C/T | | G/G |
| ABRSSJA5516 | Maternal (buffy coat) | C/C | A/G | C/T | T/T | A/G | A/G | C/T | C/C | A/C | A/G |
| | Fetal (cfDNA) | C/C | | | T/T | | | | C/T | | |
| ABRSJA5517 | Maternal (buffy coat) | A/C | G/G | C/T | A/T | A/A | A/G | C/T | C/C | A/C | A/G |
| | Fetal (cfDNA) | | | | A/G | | | | C/C | | |

Determination of Fetal Fraction

Male and female fetal fractions were determined by quantifying the identified informative SNP alleles using the Fluidigm™ dPCR platform. Simplex digital PCR was performed on the BioMark System using the 12.765 Digital Arrays (Fluidigm, South San Francisco). The real-time PCR amplification was performed using Data Collection Software. The digital array thermocycling conditions consisted of 2 min at 50° C., 10 min at 95° C., and followed by 45 cycles of a two-step thermal profile including denaturation at 95° C. for 15 seconds and combined annealing and extension at 57° C. for 60 seconds. Following amplification, digital raw data were processed by the BioMark Digital PCR Analysis software using a manually selected threshold to remove background signals and target a Ct range of 20 to 35. For SNP fetal fraction analysis, the final reaction mix for each digital panel comprised 1× TaqMan Genotyping Master Mix (Applied Biosystems), 1× sample loading reagent (Fluidigm), relevant SNP forward and reverse primers and probes, and cell-free DNA (100-300 pg). Microfluidic digital PCR (Fluidigm) was used to quantify the amount of total (fetal and maternal) and fetal DNA using TaqMan assays targeting at the EIF2C1 locus on chromosome 1 and the SRY locus on chromosome Y (Fan H C et al. PNAS 105:16266-16271 [2008]), respectively. Probes and primers used for the EIF2C1 locus and SRY locus are given in Table 4 below.

TABLE 4

Probes and Primers for the EIF2C1 and SRY Loci

| Locus | Forward Primer | Reverse Primer | Probe |
|---|---|---|---|
| EIF2C1 | GTTCGGCTTTCACCAGTCT (SEQ ID NO: 312) | CTCCATAGCTCTCCCCACT (SEQ ID NO: 313) | VIC-CGCCCTGCCATGTGGAA-MGB (SEQ ID NO: 314) |
| SRY | CGCTTAACATAGCAGAAGCAAGTTTCGAACTCTGGCACCT (SEQ ID NO: 315) | (SEQ ID NO: 316) | FAM-TGTCGCACTCTCCTTGTTTTTGACA-MGB (SEQ ID NO: 317) |

Fetal DNA fractions were determined using following formula:

fetal DNA Fraction=(fetal informative allele counts)/ ((maternal allele counts+fetal informative counts)/2)

The results shown in Table 5 below, demonstrate that fetal fraction can be determined in maternal samples of subjects carrying male or female fetuses by identifying and quantifying SNP alleles using PCR-based methods.

TABLE 5

Fetal Fraction of male and female fetuses determined by identification and quantification of SNPs

| | | | Fetal Fraction | |
|---|---|---|---|---|
| Sample ID | Fetal sex | Gestation (weeks) | SNP % | SRY % |
| 24181 | Female | 11 | 6.48 | |
| 51212 | Male | 18 | 12.92 | 7.43 |
| ABRSSJA5516 | Male | 12 | 6.61 | 5.87 |

Example 3

Specific Enrichment of Nucleic Acids and Sensitivity of SNP Detection by Real-Time PCR To increase the sensitivity of detection of SNPs in a maternal sample, cfDNA was pre-amplified prior to performing real-time PCR and/or dPCR as described above.

Template cell free DNA (250-850 pg) was amplified by PCR for 14 cycles as follows. 250-850 pg template cfDNA contained in 12.5 μl was combined with 12.5 μl of a 0.2× Pool SNP 1-20 assay mix containing the forward and reverse primers, and the corresponding probes for identifying the SNPs in Table 2, and 25 μl of 2× TaqMan PreAmp Master Mix. The cfDNA was denatured at 95° C. for 10 minutes, and amplified for 14 cycles of denaturation at 95° C. for 15 seconds and combined annealing and extension at 60° C. for 4 minutes.

The effect of preamplifying cfDNA prior to detecting informative SNPs was first tested in artificial samples of cfDNA obtained from non-pregnant subjects were spiked to contain 3%, 5% and 10% amplified products, and analyzed using ABI Real-Time TaqMan PCR. The amplified nucleic acids were diluted, and the identity of alleles at polymorphic loci was determined using ABI Real-Time TaqMan PCR. The results shown in Table 6 below indicate that preamplification of nucleic acid sequences comprising the SNPs increases the number of SNPs that can be identified in the cfDNA sample.

TABLE 6

Identification of SNPs in Artificial cfDNA Samples

| Sample ID | Without Preamplification | | With Preamplification | |
|---|---|---|---|---|
| | SNP6 | SNP10 | SNP6 | SNP10 |
| SJA01 | G/G | A/A | | |
| ART5 | A/G | A/G | | |
| ART5 3% | A/G | A/G | A/G | A/G |
| ART5 5% | A/G | A/G | A/G | A/G |
| ART5 10% | A/G | A/G | A/G | A/G |
| | SNP8 | SNP10 | SNP8 | SNP10 |
| ART7 | C/C | G/G | | |
| ART5 | C/T | A/G | | |
| ART5 3% | C/C | G/G | C/T | A/G |
| ART5 5% | C/T | G/G | C/T | A/G |
| ART5 10% | C/C | G/G | C/T | A/G |

TABLE 6-continued

Identification of SNPs in Artificial cfDNA Samples

| Sample ID | Without Preamplification | | | With Preamplification | | |
|---|---|---|---|---|---|---|
| | SNP1 | SNP5 | SNP9 | SNP1 | SNP5 | SNP9 |
| ART5 | A/A | A/A | C/C | | | |
| ART6 | A/C | A/G | A/C | | | |
| ART6 3% | A/A | A/A | A/C | A/C | A/G | A/C |
| ART6 5% | A/A | A/G | A/C | A/C | A/G | A/C |
| ART6 10% | A/C | A/G | A/C | A/C | A/G | A/C |

The effect of preamplifying cfDNA prior to detecting informative SNPs chosen from SNPs 1-10 (Table 2 above) was tested in 9 cfDNA samples obtained from pregnant subjects. Four of the 9 samples were further tested for SNPs 11-20 (Table 8).

The results shown in Table 7 below show that preamplification i.e. enrichment, of cfDNA for polymorphic target sequences enhances the sensitivity of detection of SNPs in maternal cfDNA samples. Fetal informative SNPs were detected in 9 (100%) of the preamplified samples from pregnant subjects, while fetal informative SNPs were detected in only 3 (30%) of the 9 sample in the absence of preamplification.

TABLE 7

Identification of SNPs in Maternal cfDNA samples:
Effect of Preamplification of SNP Sequences

| | Without Preamplification | | | | With Preamplification | | | |
|---|---|---|---|---|---|---|---|---|
| Sample ID | SNP 1 | SNP 5 | SNP 7 | SNP 10 | SNP 1 | SNP 5 | SNP 7 | SNP 10 |
| ABRSAC2394 gDNA | A/A | A/A | T/T | G/G | A/A | A/A | T/T | G/G |
| ABRSAC2394 cfDNA | A/A | A/A | T/T | G/G | A/A | A/G | T/T | A/G |
| | SNP 3 | SNP 4 | | | SNP 3 | SNP 4 | | |
| ABRCMD3437 gDNA | C/C | A/A | | | C/C | A/A | | |
| ABRCMD3437 cfDNA | C/C | A/A | | | C/C | A/T | | |
| | SNP 2 | SNP 4 | SNP 5 | SNP 9 | SNP 2 | SNP 4 | SNP 5 | SNP 9 |
| ABRFRA4675 gDNA | G/G | T/T | A/A | A/A | G/G | T/T | A/A | A/A |
| ABRFRA4675 cfDNA | G/G | T/T | A/A | A/A | G/G | T/T | A/G | A/C |
| | SNP 2 | SNP 4 | SNP 7 | | SNP 2 | SNP 4 | SNP 7 | |
| ABRSAC9818 gDNA | G/G | T/T | T/T | | G/G | T/T | T/T | |
| ABRSAC9818 cfDNA | G/G | T/T | T/T | | G/G | A/T | T/T | |
| | SNP 2 | SNP 4 | SNP 5 | | SNP 2 | SNP 4 | SNP 5 | |
| ABRSAC9830 gDNA | G/G | A/A | A/A | | G/G | A/A | A/A | |
| ABRSAC9830 gDNA | G/G | A/A | A/A | | G/G | A/T | A/G | |
| | SNP 2 | SNP 3 | SNP 7 | SNP 8 | SNP 2 | SNP 3 | SNP 7 | SNP 8 |
| ABRCMD3362 gDNA | G/G | T/T | C/C | T/T | G/G | T/T | C/C | T/T |
| ABRCMD3362 cfDNA | G/G | T/T | C/C | C/T | A/G | T/T | C/C | C/T |
| | SNP 1 | SNP 2 | SNP 3 | SNP 4 | SNP 1 | SNP 2 | SNP 3 | SNP 4 |
| ABRSJA5500 gDNA | C/C | G/G | C/C | A/A | C/C | G/G | C/C | A/A |
| ABRSJA5500 cfDNA | A/C | G/G | C/C | A/A | A/C | A/G | C/C | A/T |
| | SNP 1 | SNP 4 | SNP 8 | | SNP 1 | SNP 4 | SNP 8 | |
| ABRSJA5516 gDNA | C/C | T/T | C/C | | C/C | T/T | C/C | |
| ABRSJA5516 cfDNA | C/C | T/T | C/T | | A/C | A/T | C/T | |

TABLE 7-continued

Identification of SNPs in Maternal cfDNA samples:
Effect of Preamplification of SNP Sequences

|  | Without Preamplification | | | With Preamplification | | |
| --- | --- | --- | --- | --- | --- | --- |
|  | SNP 2 | SNP 5 | SNP 8 | SNP 2 | SNP 5 | SNP 8 |
| ABRSJA5517 gDNA | G/G | A/A | C/C | G/G | A/A | C/C |
| ABRSJA5517 cfDNA | G/G | A/G | C/C | A/G | A/G | C/T |

TABLE 8

Detection of Additional SNPs Following Preamplification

| Sample ID | SNP13 | SNP14 | SNP16 | SNP19 | |
| --- | --- | --- | --- | --- | --- |
| ABRSAC2394 gDNA | G/G | A/A | A/A | T/T | |
| ABRSAC2394 cfDNA | G/G | A/G | A/T | C/T | |

| | SNP13 | SNP14 | SNP15 | SNP18 | SNP19 |
| --- | --- | --- | --- | --- | --- |
| ABRCM3400 gDNA | A/A | A/A | G/G | T/T | T/T |
| ABRCM3400 cfDNA | A/G | A/G | A/G | T/T | C/T |

| | SNP18 | SNP19 | | | |
| --- | --- | --- | --- | --- | --- |
| ABRCMD3437 gDNA | T/T | C/C | | | |
| ABRCMD3437 cfDNA | A/T | C/T | | | |

| | SNP15 | SNP19 | SNP20 | | |
| --- | --- | --- | --- | --- | --- |
| ABRFRA4675 gDNA | G/G | C/C | G/G | | |
| ABRFRA4675 cfDNA | A/G | C/T | A/G | | |

| | SNP14 | SNP15 | SNP17 | SNP19 | |
| --- | --- | --- | --- | --- | --- |
| ABRSAC9818 gDNA | A/A | G/G | G/G | C/C | |
| ABRSAC9818 cfDNA | A/G | A/G | G/G | C/T | |

| | SNP14 | SNP15 | | | |
| --- | --- | --- | --- | --- | --- |
| ABRSAC9825 gDNA | A/A | A/A | | | |
| ABRSAC9825 gDNA | A/T | A/A | | | |

| | SNP12 | SNP17 | SNP18 | SNP19 | |
| --- | --- | --- | --- | --- | --- |
| ABRSAC9829 gDNA | A/A | C/C | A/A | C/C | |
| ABRSAC9829 cfDNA | A/C | C/C | A/A | C/T | |

| | SNP13 | SNP15 | SNP17 | SNP18 | SNP19 |
| --- | --- | --- | --- | --- | --- |
| ABRSAC9830 gDNA | G/G | A/A | G/G | A/A | T/T |
| ABRSAC9830 cfDNA | A/G | A/G | G/G | A/A | C/T |

Example 4

Identification of Polymorphisms by Massively Parallel Sequencing of Samples Comprising a Mixture of Fetal and Maternal cfDNA: Sample Processing, Preparation of Sequencing Libraries, Sequencing, and Analysis of Sequencing Data (a) Sample Processing and cfDNA Extraction Peripheral blood samples were collected from pregnant women in their first or second trimester of pregnancy and who were deemed at risk for fetal aneuploidy. Informed consent was obtained from each participant prior to the blood draw. Blood was collected before amniocentesis or chorionic villus sampling. Karyotype analysis was performed using the chorionic villus or amniocentesis samples to confirm fetal karyotype.

Peripheral blood drawn from each subject was collected in ACD tubes. One tube of blood sample (approximately 6-9 mL/tube) was transferred into one 15-mL low speed centrifuge tube. Blood was centrifuged at 2640 rpm, 4° C. for 10 min using Beckman Allegra 6 R centrifuge and rotor model GA 3.8.

For cell-free plasma extraction, the upper plasma layer was transferred to a 15-ml high speed centrifuge tube and centrifuged at 16000×g, 4° C. for 10 min using Beckman Coulter Avanti J-E centrifuge, and JA-14 rotor. The two centrifugation steps were performed within 72 h after blood collection. Cell-free plasma comprising cfDNA was stored at −80° C. and thawed only once before amplification of plasma cfDNA or for purification of cfDNA.

Purified cell-free DNA (cfDNA) was extracted from cell-free plasma using the QIAamp Blood DNA Mini kit (Qiagen) essentially according to the manufacturer's instruction. One milliliter of buffer AL and 100 µl of Protease solution were added to 1 ml of plasma. The mixture was incubated for 15 minutes at 56° C. One milliliter of 100% ethanol was added to the plasma digest. The resulting mixture was transferred to QIAamp mini columns that were assembled with VacValves and VacConnectors provided in the QIAvac 24 Plus column assembly (Qiagen). Vacuum was applied to the samples, and the cfDNA retained on the column filters was washed under vacuum with 750 µl of buffer AW1, followed by a second wash with 750 µl of buffer AW24. The column was centrifuged at 14,000 RPM for 5 minutes to remove any residual buffer from the filter. The cfDNA was eluted with buffer AE by centrifugation at 14,000 RPM, and the concentration determined using Qubit™ Quantitation Platform (Invitrogen).

(b) Preparation of Sequencing Libraries

All sequencing libraries i.e. target, primary and enriched libraries, were prepared from approximately 2 ng of purified cfDNA that was extracted from maternal plasma. Library preparation was performed using reagents of the NEBNext™ DNA Sample Prep DNA Reagent Set 1 (Part No. E6000L; New England Biolabs, Ipswich, Mass.) for Illumina® as follows. Because cell-free plasma DNA is fragmented in nature, no further fragmentation by nebulization or sonication was done on the plasma DNA samples. The overhangs of approximately 2 ng purified cfDNA fragments contained in 40 µl were converted into phosphorylated blunt ends according to the NEBNext® End Repair Module by incubating in a 1.5 ml microfuge tube the cfDNA with 5 µl 10× phosphorylation buffer, 2 µl deoxynucleotide solution mix (10 mM each dNTP), 1 µl of a 1:5 dilution of DNA Polymerase I, 1 µl T4 DNA Polymerase and 1 µl T4 Polynucleotide Kinase provided in the NEBNext™ DNA Sample Prep DNA Reagent Set 1 for 15 minutes at 20° C. The enzymes were then heat inactivated by incubating the reaction mixture at 75° C. for 5 minutes. The mixture was cooled to 4° C., and dA tailing of the blunt-ended DNA was accomplished using 10 µl of the dA-tailing master mix containing the Klenow fragment (3' to 5' exo minus) (NEBNext™ DNA Sample Prep DNA Reagent Set 1), and incubating for 15 minutes at 37° C. Subsequently, the Klenow fragment was heat inactivated by incubating the reaction mixture at 75° C. for 5 minutes. Following the inactivation of the Klenow fragment, 1 µl of a 1:5 dilution of Illumina Genomic Adaptor Oligo Mix (Part No. 1000521; Illumina Inc., Hayward, Calif.) was used to ligate the Illumina adaptors (Non-Index Y-Adaptors) to the dA-tailed DNA using 4 µl of the T4 DNA ligase provided in the NEBNext™ DNA Sample Prep DNA Reagent Set 1, by incubating the reaction mixture for 15 minutes at 25° C. The mixture was cooled to 4° C., and the adaptor-ligated cfDNA was purified from unligated adaptors, adaptor dimers, and other reagents using magnetic beads provided in the Agencourt AMPure XP PCR purification system (Part No. A63881; Beckman Coulter Genomics, Danvers, Mass.). Eighteen cycles of PCR were performed to selectively enrich adaptor-ligated cfDNA using Phusion® High-Fidelity Master Mix (Finnzymes, Woburn, Mass.) and Illumina's PCR primers complementary to the adaptors (Part No. 1000537 and 1000537). The adaptor-ligated DNA was subjected to PCR (98° C. for 30 seconds; 18 cycles of 98° C. for 10 seconds, 65° C. for 30 seconds, and 72° C. for 30 seconds; final extension at 72° C. for 5 minutes, and hold at 4° C.) using Illumina Genomic PCR Primers (Part Nos. 100537 and 1000538) and the Phusion HF PCR Master Mix provided in the NEBNext™ DNA Sample Prep DNA Reagent Set 1, according to the manufacturer's instructions. The amplified product was purified using the Agencourt AMPure XP PCR purification system (Agencourt Bioscience Corporation, Beverly, Mass.) according to the manufacturer's instructions available at www.beckmangenomics.com/products/AMPureXPProtocol_000387v001.pdf. The purified amplified product was eluted in 40 µl of Qiagen EB Buffer, and the concentration and size distribution of the amplified libraries was analyzed using the Agilent DNA 1000 Kit for the 2100 Bioanalyzer (Agilent technologies Inc., Santa Clara, Calif.).

(c) Sequencing

Sequencing of library DNA was performed using the Genome Analyzer II (Illumina Inc., San Diego, Calif., USA) according to standard manufacturer protocols. Copies of the protocol for whole genome sequencing using Illumina/Solexa technology may be found at BioTechniques.RTM. Protocol Guide 2007 Published December 2006: p 29, and on the world wide web at biotechniques.com/default.asp?page=protocol&subsection=article_display&id=112378. The DNA library was diluted to 1 nM and denatured. Library DNA (5 pM) was subjected to cluster amplification according to the procedure described in Illumina's Cluster Station User Guide and Cluster Station Operations Guide, available on the world wide web at illumina.com/systems/genome analyzer/cluster_station-.ilmn. The amplified DNA was sequenced using Illumina's Genome Analyzer II to obtain single-end reads of 36 bp. Only about 30 bp of random sequence information are needed to identify a sequence as belonging to a specific human chromosome. Longer sequences can uniquely identify more particular targets. In the present case, a large number of 36 bp reads were obtained, covering approximately 10% of the genome.

(d) Analysis of Sequencing Data for the Determination of Fetal Fraction

Upon completion of sequencing of the sample, the Illumina "Sequencer Control Software" transferred image and base call files to a Unix server running the Illumina "Genome Analyzer Pipeline" software version 1.51. The 36 bp reads were aligned to an artificial reference genome e.g. a SNP genome, using the BOWTIE program. The artificial reference genome was identified as the grouping of the polymorphic DNA sequences that encompass the alleles comprised in the polymorphic target sequences. For example, the artificial reference genome is a SNP genome comprising SEQ ID NOs: 1-56. Only reads that mapped uniquely to the artificial genome were used for the analysis of fetal fraction. Reads that matched perfectly to the SNP genome were counted as tags and filtered. Of the remaining reads, only reads having one or two mismatches were counted as tags and included in the analysis. Tags mapped to each of the polymorphic alleles were counted, and the fetal fraction was determined as a percent of the ratio of the number of tags mapped to the major allele i.e. maternal allele, and the number of tags mapped to the minor allele i.e. fetal allele.

Example 5

Selection of Autosomal SNPs for Identification by Massively Parallel Sequencing

A set of 28 autosomal SNPs were selected from a list of 92 SNPs (Pakstis et al., Hum Genet 127:315-324 [2010]) and from Applied Biosystems by Life Technologies™ (Carlsbad, Calif.) at world wide web address appliedbiosystems.com, and validated for use in multiplexed PCR amplification. Primers were designed to hybridize to a sequence close to the SNPs site on the cfDNA to ensure that it be included in the 36 bp read generated from the massively parallel sequencing on the Illumina Analyzer GII, and to generate amplicons of sufficient length to undergo bridge-amplification during cluster formation. Thus, primers were designed to generate amplicons that were at least 110 bp, which when combined with the universal adaptors (Illumina Inc., San Diego, Calif.) used for cluster amplification, resulted in DNA molecules of at least 200 bp. Primer sequences were identified, and primer sets i.e. forward and reverse primers, were synthesized by Integrated DNA Technologies (San Diego, Calif.), and stored as a 1 µM solution to be used for amplifying polymorphic target sequences as described in Examples 6-9. Table 8 provides the RefSNP (rs) accession ID numbers, the primers used for amplifying the target cfDNA sequence, and the sequences of the amplicons comprising the possible SNP alleles that would be generated using the primers. The SNPs given in Table 1 were used for the simultaneous amplification of 13 target sequences in a multiplexed assay. The panel provided in Table 9 is an exemplary SNP panel. Fewer or more SNPs can be employed to enrich the fetal and maternal DNA for polymorphic target nucleic acids. Additional SNPs that can be used include the SNPs given in Table 10. The SNP alleles are shown in bold and are underlined. Other additional SNPs that can be used to determine fetal fraction according to the present method include rs315791, rs3780962, rs1410059, rs279844, rs38882, rs9951171, rs214955, rs6444724, rs2503107, rs1019029, rs1413212, rs1031825, rs891700, rs1005533, rs2831700, rs354439, rs1979255, rs1454361, rs8037429, and rs1490413, which have been analyzed for determining fetal fraction by TaqMan PCR, and are disclosed in U.S. Provisional applications 61/296,358 and 61/360,837.

TABLE 9

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs560681 | 1 | CACATGCACAGCCAGCACATGCACAGCCAGCACATGCACAGCCAGCAAC CAACCCTGTCAGCAGCAACCCTGTCAGCAGCC GAGTTCCCACCAGTTGAGTTCCCACCAGTT TCTTTCTGAGAACATTCTTTCTGAGAACAT CTGTTCAGGTTTCTCCTGTTCAGGTTTCTC TCCATCTCATTTACTCCATCTCTTTTAC TCAGGTCACAGGAC CTTGGGG (SEQ ID NO: 1) | TCAGGTCACAGGACC TTGGGG (SEQ ID NO: 2) | CCCCAAGGTCCTGTGACCT (rs560681_C1_1_F; SEQ ID NO: 57) | CCCCAAGGTCCTGTGACCT GAGT (rs560681_C1_1_R; SEQ ID NO: 58) |
| rs1109037 | 2 | TGAGGAAGTGAGGCTTGAGGAAGTGAGGCTTGAGGAAGTGAGGCTCAGA CAGAGGGTAAGAAACCAGAGGGTAAGAAACGGGT TTTGTCACAGAGCTGTTTGTCACAGAGCTG GTGGTGAGGGTGGAGGTGGTGAGGGTGGAG ATTTTACACTCCCTGATTTTACACTCCCTG CCTCCCACACCAGTTCCTCCCACACCAGTT TCTCCAGAGTGGAAATCTCCGGAGTGGAAA GACTTTCATCTCGCAGACTTTCATCTCGCA CTGGCA (SEQ ID NO: 3) | CTGGCA (SEQ ID NO: 4) | TGCCAGTGCGAGATGAAAG (rs110937_C2_1_F; SEQ ID NO: 59) | TGCCAGTGCGAGATGAAAG TCTTT (rs110937_C2_1_R; SEQ ID NO: 60) |
| rs9866013 | 3 | GTGCCTTCAGAACCTGTGCCTTCAGAACCTGTGCCTTCAGAACCTTTGA TTGAGATCTGATTCTTTGAGATCTGATTCTGATCTGAT ATTTTTAAAGCTTCTATTTTTAAAGCTTCT TAGAAGAGAGATTGCTAGAAGAGAGATTGC AAAGTGGGTTGTTTCAAAGTGGGTTGTTTC TCTAGCCAGACAGGGTCTAGCCAGACAGGG CAGGCAAATAGGGGTCAGGTAAATAGGGGT GGCTGGTGGGATGGGGGCTGGTGGGATGGG A (SEQ ID NO: 5) | A (SEQ ID NO: 6) | TCCCATCCCACCAGCCACC (rs9866013_C3_1_F; SEQ ID NO: 61) | TCCCATCCCACCAGCCACC C (rs9866013_C3_1_R; SEQ ID NO: 62) |
| rs13182883 | 5 | AGGTGTGTCTCTCTTAGGTGTGTCTCTCTTAGGTGTGTCTCTCTTTTGT TTGTGAGGGGAGGGGTTGTGAGGGGAGGGGGAGGGG TCCCTTCTGGCCTAGTCCCTTCTGGCCTAG TAGAGGGCCTGGCCTTAGAGGGCCTGGCCT GCAGTGAGCATTCAAGCAGTGAGCATTCAA ATCCTCAAGGAACAGATCCTCGAGGAACAG GGTGGGGAGGTGGG ACAAAGG (SEQ ID NO: 7) | GGTGGGGAGGTGGGA CAAAGG (SEQ ID NO: 8) | CCTTTGTCCCACCTCCCCA (rs13182883_C5_1_F; SEQ ID NO: 63) | CCTTTGTCCCACCTCCCCA CC (rs13182883_C5_1_R; SEQ ID NO: 64) |
| rs13218440 | 6 | CCTCGCCTACTGTGCCCTCGCCTACTGTGCCCTCGCCTACTGTGCTGTT TGTTTCTAACCATCATGTTTCTAACCATCATCTAACC TGCTTTTCCCTGAATTGCTTTTCCCTGAAT CTCTTGAGTCTTTTTCTCTTGAGTCTTTTT CTGCTGTGGACTGAACTGCTGTGGACTGAA ACTTGATCCTGAGATACTTGATCCTGAGAT TCACCTCTAGTCCCTTCACCTCTAGTCCCT CTGAGCAGCCTCCTGCTGGGCAGCCTCCTG GAATACTCAGCTGGGGAATACTCAGCTGGG ATGG (SEQ ID NO: 9) | ATGG (SEQ ID NO: 10) | CCATCCCAGCTGAGTATTC CAGGAG (rs13218440_C6_1_F; SEQ ID NO: 65) | CCATCCCAGCTGAGTATTC CAGGAG (rs13218440_C6_1_R; SEQ ID NO: 66) |
| rs7041158 | 9 | AATTGCAATGGTGAGAATTGCAATGGTGAGAATTGCAATGGTGAGAGGT AGGTTGATGGTAAAAAGGTTGATGGTAAAATGATGGT TCAAACGGAACTTGTTCAAACGGAACTTGT TATTTTGTCATTCTGTATTTTGTCATTCTG ATGGACTGAACTGAATGGACTGGAACTGA GGATTTTCAATTTCCGGATTTTCAATTTCC TCTCCAACCCAAGACTTTCCAACCCAAGAC ACTTCTCACTGG ACTTCTCACTGG (SEQ ID NO: 11) | (SEQ ID NO: 12) | CCAGTGAGAAGTGTCTTGG GTTGG (SEQ ID NO: 67) | CCAGTGAGAAGTGTCTTGG GTTGG (SEQ ID NO: 68) |
| rs740598 | 10 | GAAATGCCTTCTCAGGAAATGCCTTCTCAGGAAATGCCTTCTCAGGTAA GTAATGGAAGGTTATGTAATGGAAGGTTATTGGAAGGT CCAAATATTTTCGTCCAAATATTTTTCGT AAGTATTTCAAATAGAAGTATTTCAAATAG CAATGGCTCGTCTATCAATGGCTCGTCTAT GGTTAGTCTCACAGCGGTTAGTCTCGCAGC CAATTCTCAGAACTGCACATTCTCAGAACT CTCAAACC (SEQ ID NO: 13) | GCTCAAACC (SEQ ID NO: 14) | GGTTTGAGCAGTTCTGAGA ATGTGGCT (SEQ ID NO: 69) | GGTTTGAGCAGTTCTGAGA ATGTGGCT (SEQ ID NO: 70) |

TABLE 9-continued

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs10773760 | 12 | ACCCAAAACACTGGAACCCAAAACACTGGAACCCAAAACACTGGAGGGGGGGGCCTCTTCTCATGGGGCCTCTTCTCATCCTTTTCGGTAGACTGCATTTCGGTAGACTGCAAGTGTTAGCCGTCGGAGTGTTAGCCGTCGGGACCAGCTTCTGTCTGACCAGCTTCTGTCTGGAAGTTCGTCAAATGGAAGTTCGTCAAATTGCAGTTAAGTCCAATGCAGTTAGGTCCAAGTATGCCACATAGCAGTATGCCACATAGCAGATAAGGG (SEQ ID NO: 15) | GATAAGGG (SEQ ID NO: 16) | CCCTTATCTGCTATGTGGCATACTTGG (SEQ ID NO: 71) | (SEQ ID NO: 72) |
| rs4530059 | 14 | GCACCAGAATTTAAAGCACCAGAATTTAAAGCACCAGAATTTAAACAACCAACGCTGACAATAACAACGCTGACAATAAGCTGACAAATATGCAGTCGATGAATATGCAGTCGATGATGACTTCCCAGAGCTTGACTTCCCAGAGCTCCAGAAGCAACTCCACCAGAAGCAACTCCAGCACACAGAGAGGCGGCACACGGAGAGGCGCTGATGTGCCTGTCACTGATGTGCCTGTCAGGTGC (SEQ ID NO: 17) | GGTGC (SEQ ID NO: 18) | GCACCTGACAGGCACATCAGCG (SEQ ID NO: 73) | (SEQ ID NO: 74) |
| rs7205345 | 16 | TGACTGTATACCCCATGACTGTATACCCCATGACTGTATACCCCAGGTGGGTGCACCCTTGGGTGGTGCACCCTTGGGTCACCCCATCTCTATCATAGACATCTCTATCATAGAACTTATCTCACAGAGACTTATCTCACAGAGTATAAGAGCTGATTTTATAAGAGCTGATTTCTGTGTCTGCCTCTCCTGTGTCTGCCTGTCACACTAGACTTCCACACACTAGACTTCCACATCCTTAGTGC (SEQ ID NO: 19) | ATCCTTAGTGC (SEQ ID NO: 20) | GCACTAAGGATGTGGAAGTCTAGTGTG (SEQ ID NO: 75) | (SEQ ID NO: 76) |
| rs8078417 | 17 | TGTACGTGGTCACCATGTACGTGGTCACCATGTACGTGGTCACCAGGGGGGGGACGCCTGGCGCGGGGACGCCTGGCGCACGTGCGAGGGAGGCCCCTGCGAGGGAGGCCCCGAGCCTCGTGCCCCCGAGCCTCGTGCCCCCGTGAAGCTTCAGCTCGTGAAGCTTCAGCTCCCCTCCCCGGCTGTCCCCTCCCTGGCTGTCCTTGAGGCTCTTCTCCTTGAGGCTCTTCTCACACT (SEQ ID NO: 21) | ACACT (SEQ ID NO: 22) | AGTGTGAGAAGAGCCTCAAGGACAGC (SEQ ID NO: 77) | (SEQ ID NO: 78) |
| rs576261 | 19 | CAGTGGACCCTGCTGCAGTGGACCCTGCTGCAGTGGACCCTGCTGCACCCACCTTTCCTCCCCTCACCTTTCCTCCCCTTTCCCATCAACCTCTTTCCCATCAACCTCTTTTGTGCCTCCCCCTCCTGTGCCTCCCCCTCCGTGTACCACCTTCTCGTGTACCACCTTCTCTGTCACCAACCCTGGTGTCACCACCCCTGGCCTCACAACTCTCTCCCTCACAACTCTCTCCTTTGCCAC (SEQ ID NO: 23) | CTTTGCCAC (SEQ ID NO: 24) | GTGGCAAAGGAGAGAGTTGTGAGG (SEQ ID NO: 79) | (SEQ ID NO: 80) |
| rs2567608 | 20 | CAGTGGCATAGTAGTCAGTGGCATAGTAGTCAGTGGCATAGTAGTCCAGCCAGGGGCTCCTCCTCCAGGGGCTCCTCCTGGGCTCAGCACCTCCAGCACCAGCACCTCCAGCACCTTCCAGGAGGCAGCCTTCCAGGAGGCAGCAGCGCAGGCAGAGAAAGCGCAGGCAGAGAACCCGCTGGAAGAATCCCCGCTGGAAGGATCGGCGGAAGTTGTCGGGGCGGAAGTTGTCGGAGAGG (SEQ ID NO: 25) | AGAGG (SEQ ID NO: 26) | CCTCTCCGACAACTTCCGCCG (SEQ ID NO: 81) | (SEQ ID NO: 82) |

TABLE 10

Additional SNPs for the Determination of Fetal Fraction

| SNP ID | Amplicon: Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs430046 | 16 | AGGTCTGGGGGCCGCAGGTCTGGGGGCCGCTTGAATGCCAAGCTGGTGAATGCCAAGCTGGGAATGAATCTTAAATGTTAGAATCTTAAATGTTAAGGAACAAGGTCATAAGGAACAAGGTCATACAATGAATGGTGTGACAATGAATGGTGTGATGTAAAAGCTTGGGATGTAAAAGCTTGGGAGGTGATTTCTGAGGGGGTGATTTTTGAGGGTAGGTGCTGGGTTTATAGGTGCTGGGTTTAATGGGAGGA (SEQ ID NO: 27) | AGGTCTGGGGGCCGCAGGTCTGGGGGCCGCTTGAATGCCAAGCTGGTGAATGCCAAGCTGGGAATGAATCTTAAATGTTAGAATCTTAAATGTTAAGGAACAAGGTCATAAGGAACAAGGTCATACAATGAATGGTGTGACAATGAATGGTGTGATGTAAAAGCTTGGGATGTAAAAGCTTGGGAGGTGATTTCTGAGGGGGTGATTTTTGAGGGTAGGTGCTGGGTTTATAGGTGCTGGGTTTAATGGGAGGA (SEQ ID NO: 28) | (rs430046_C1_1F; SEQ ID NO: 83) | TCCTCCCATTAAACCCAGCACCT (rs430046_C1_1_R; SEQ ID NO: 84) |
| rs9951171 | 18 | ACGGTTCTGTCCTGTACGGTTCTGTCCTGTACGGTTCTGTCCTGTAAGGGGAGAAAAGTCCAGGGGAGAAAAGTCCGGGGAGATCGTTGTTCCTCTGGTCGTTGTTCCTCTGG GATGCAACATGAGAGGATGCAACATGAGAGAGCAGCACACTGAGGAGCAGCACACTGAGGCTTTATGGATTGCCCCTTTATGGGTTGCCCTGCCACAAGTGAACATGCCACAAGTGAACAGG (SEQ ID NO: 29) | ACGGTTCTGTCCTGTACGGTTCTGTCCTGTACGGTTCTGTCCTGTAAGGGGAGAAAAGTCCAGGGGAGAAAAGTCCGGGGAGATCGTTGTTCCTCTGGTCGTTGTTCCTCTGG GATGCAACATGAGAGGATGCAACATGAGAGAGCAGCACACTGAGGAGCAGCACACTGAGGCTTTATGGATTGCCCCTTTATGGGTTGCCCTGCCACAAGTGAACATGCCACAAGTGAACAGG (SEQ ID NO: 30) | (rs9951171_C1_1_F; SEQ ID NO: 85) | CCTGTTCACTTGTGGCAGGGCA (rs9951171_C_1_R; SEQ ID NO: 86) |
| rs338882 | 5 | GCGCAGTCAGATGGGGCGCAGTCAGATGGGGCGCAGTCAGATGGGCGTCGTGCTGGCGTCTGTCGTGCTGGCGTCTGTCCTTCTCTCTCCTGCTTCTCTCTCTCCTGCTCTCTGGCTTCATTCTCTCTGGCTTCATTTTTCTCTCCTTCTGTTTTCTCTCCTTCTGTCTCACCTTCTTTCGTCTCACCTTCTTTCGTGTGCCTGTGCACACAGTGCCTGTGCATACACACGTTTGGGACAAGCACGTTTGGGACAAGGGCTGGA (SEQ ID NO: 31) | GCGCAGTCAGATGGGGCGCAGTCAGATGGGGCGCAGTCAGATGGGCGTCGTGCTGGCGTCTGTCGTGCTGGCGTCTGTCCTTCTCTCTCCTGCTTCTCTCTCTCCTGCTCTCTGGCTTCATTCTCTCTGGCTTCATTTTTCTCTCCTTCTGTTTTCTCTCCTTCTGTCTCACCTTCTTTCGTCTCACCTTCTTTCGTGTGCCTGTGCACACAGTGCCTGTGCATACACACGTTTGGGACAAGCACGTTTGGGACAAGGGCTGGA (SEQ ID NO: 32) | (rs338882_C1_1_F; SEQ ID NO: 87) | TCCAGCCCTTGTCCCAACGTGT (rs338882_C1_1_R; SEQ ID NO: 88) |
| rs10776839 | 9 | GCCGGACCTGCGAAAGCCGGACCTGCGAAAGCCGGACCTGCGAAATCCTCCCAAAATGCCAAATCCCAAAATGCCAAACAACATTCCCGCCTCACACATTCCCGCCTCACATGATCCCAGAGAGAGTGATCCCAGAGAGAGGGGACCCAGTGTTCCGGGACCCAGTGTTCCCAGCTTGCAGCTGAGCAGCTTGCAGCTGAGGAGCCCGAGGTTGCCGAGCCCGAGTTTGCCGTCAGATCAGAGCCCGTCAGATCAGAGCCCCAGTTGCCCG (SEQ ID NO: 33) | GCCGGACCTGCGAAAGCCGGACCTGCGAAAGCCGGACCTGCGAAATCCTCCCAAAATGCCAAATCCCAAAATGCCAAACAACATTCCCGCCTCACACATTCCCGCCTCACATGATCCCAGAGAGAGTGATCCCAGAGAGAGGGGACCCAGTGTTCCGGGACCCAGTGTTCCCAGCTTGCAGCTGAGCAGCTTGCAGCTGAGGAGCCCGAGGTTGCCGAGCCCGAGTTTGCCGTCAGATCAGAGCCCGTCAGATCAGAGCCCCAGTTGCCCG (SEQ ID NO: 34) | (rs10776839_C1_1_F; SEQ ID NO: 89) | CGGGCAACTGGGGCTCTGATC (rs10776839_C1_1_R; SEQ ID NO: 90) |
| rs9905977 | 17 | AGCAGCCTCCCTCGAAGCAGCCTCCCTCGAAGCAGCCTCCCTCGACTAGCTAGCTCACACTACGCTAGCTCACACTACGCTATAAGGAAAATTCATATAAGGAAAATTCATGAGCTGGTGTCCAAGGAGCTGGTGTCCAAGGAGGGCTGGGTGACTGAGGGCTGGGTGACTCGTGGCTCAGTCAGCCGTGGCTCAGTCAGCATCAAGATTCCTTTCGTCAAGATTCCTTTCGTCTTTCCCCTCTGCGTCTTTCCCCTCTGCC (SEQ ID NO: 35) | AGCAGCCTCCCTCGAAGCAGCCTCCCTCGAAGCAGCCTCCCTCGACTAGCTAGCTCACACTACGCTAGCTCACACTACGCTATAAGGAAAATTCATATAAGGAAAATTCATGAGCTGGTGTCCAAGGAGCTGGTGTCCAAGGAGGGCTGGGTGACTGAGGGCTGGGTGACTCGTGGCTCAGTCAGCCGTGGCTCAGTCAGCATCAAGATTCCTTTCGTCAAGATTCCTTTCGTCTTTCCCCTCTGCGTCTTTCCCCTCTGCC (SEQ ID NO: 36) | (rs9905977_C1_1_F; SEQ ID NO: 91) | GGCAGAGGGGAAAGACGAAAGGA (rs9905977_C1_1_R; SEQ ID NO: 92) |
| rs1277284 | 4 | TGGCATTGCCTGTAATGGCATTGCCTGTAATGGCATTGCCTGTAATATATATACATAGCCATGGTATACATAGCCATGGCATAGTTTTTTATAGGCAATTTTTTTTATAGGCAATTTAAGATGAATAGCTTTAAGATGAATAGCTTCTAAACTATAGATATCTAAACTATAGATAAGTTTCATTACCCCAAGTTTCATTACCCCAGGAAGCTGAACTATAGGAAGCTGAACTATAGCTACTTTACCCAAAGCTACTTTCCCCAAAATCATTAGAATGGTGATCATTAGAATGGTGCTT (SEQ ID NO: 37) | TGGCATTGCCTGTAATGGCATTGCCTGTAATGGCATTGCCTGTAATATATATACATAGCCATGGTATACATAGCCATGGCATAGTTTTTTATAGGCAATTTTTTTTATAGGCAATTTAAGATGAATAGCTTTAAGATGAATAGCTTCTAAACTATAGATATCTAAACTATAGATAAGTTTCATTACCCCAAGTTTCATTACCCCAGGAAGCTGAACTATAGGAAGCTGAACTATAGCTACTTTACCCAAAGCTACTTTCCCCAAAATCATTAGAATGGTGATCATTAGAATGGTGCTT (SEQ ID NO: 38) | (rs1277284_C4_1_F; SEQ ID NO: 93) | AAGCACCATTCTAATGATTTTGG (rs1277284_C4_1_R; SEQ ID NO: 94) |
| rs258684 | 7 | ATGAAGCCTTCCACCATGAAGCCTTCCACCATGAAGCCTTCCACCAACTAACTGCCTGTATGACAACTGCCTGTATGACGTCATCTGGGGACTTCTCATCTGGGGACTTCTGCTCTATACTCAAATGCTCTATACTCAAAGTGGCTTAGTCACTGGTGGCTTAGTCACTGCCAATGTATTTCCATCCAATGTATTTCCATATGAGGGACGATGATATGAGGGACGGTGATTACTAAGGAAATATATACTAAGGAAATATA | ATGAAGCCTTCCACCATGAAGCCTTCCACCATGAAGCCTTCCACCAACTAACTGCCTGTATGACAACTGCCTGTATGACGTCATCTGGGGACTTCTCATCTGGGGACTTCTGCTCTATACTCAAATGCTCTATACTCAAAGTGGCTTAGTCACTGGTGGCTTAGTCACTGCCAATGTATTTCCATCCAATGTATTTCCATATGAGGGACGATGATATGAGGGACGGTGATTACTAAGGAAATATATACTAAGGAAATATA | (rs258684_C7_1_F; SEQ ID NO: 95) | GATCAGTTGTTGTTTCTATATTTCCTT (rs258684_C7_1_R; SEQ ID NO: 96) |

TABLE 10-continued

Additional SNPs for the Determination of Fetal Fraction

| SNP ID | Amplicon: Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| | | GAAACAACAACTGAT C (SEQ ID NO: 39) | GAAACAACAACTGAT C (SEQ ID NO: 40) | | |
| rs1347696 | 8 | ACAACAGAATCAGGT GATTGGAGAAAAGAT CACAGGCCTAGGCAC CCAAGGCTTGAAGGA TGAAAGAATGAAAGA TGGACGGAACAAAAT TAGGACCTTAATTCT TTGTTCAGTTCAG (SEQ ID NO: 41) | ACAACAGAATCAGGT GATTGGAGAAAAGAT GGA CACAGGCCTAGGCAC CCAAGGCTTGAAGGA TGAAAGAATGAAAGA TGGACGGAAGAAAAT TAGGACCTTAATTCT TTGTTCAGTTCAG (SEQ ID NO: 42) | ACAACAGAATCAGGTGATT (rs1347696_C8_R_F; SEQ ID NO: 97) | CTGAACTGAACAAAGAATT AAGGTC (rs1347696_C8_4_F; SEQ ID NO: 98) |
| rs508485 | 11 | TTGGGGTAAATTTTCTT ATTGTCATATGTGGAATT ATTTAAATATACCATATT CATCTACAAAGAATTCAT CCACAGAGTTAAATA TCTTAAGTTAAACACT TTAAAATAAGTGTTTT GCGTGATATTTTGAT GACAGATAAACAGAGGA TCTAATTCCCACCCCT (SEQ ID NO: 43) | TTGGGGTAAATTTTCTT GGGTAAATTTTCATTG GTCATATGTGGATCA TAAATATACCAT CTACAAAGAATT CCACAGAGTTAAATA CTCTTAAGTTAAACAC TTAAAATAAGTGTTT GCGTGATATTTTGAT GATAGATAAACAGAG TCTAATTCCCACCCC (SEQ ID NO: 44) | GGGTAAATTTTCATTG (rs508485_C11_1_F; SEQ ID NO: 99) | GGGGTGGGAATTAGACTCT G (rs508485_C11_1_R; SEQ ID NO 100) |
| rs9788670 | 15 | TGCAATTCAAATCAGT GAAGTATGACCAAAAG GACAGAGATCTTTTT TGGATGATCCCTAGC CTAGCAATGCCTGGC AGCCATGCAGGTGCA ATGTCAACCTTAAAT AATGTATTGCAAACT CAGAGCTGACAAACC TCGATGTTGC (SEQ ID NO: 45) | TGCAATTCAAATCAGT GCAATTCAAATCAGGAAG AAGTATGACCAAAATATG GACAGAGATCTTTTT TGGATGATCCCTAGC CTAGCAATGCCTGGC AGCCATGCAGGTGCA ATGTCAACCTTAAAT AATGTATTGCAAATT CAGAGCTGACAAACC TCGATGTTGC (SEQ ID NO: 46) | (rs9788670_c15_2_F; SEQ ID NO: 101) | GCAACATCGAGGTTTGTCA G (rs9788670_c15_2_R; SEQ ID NO: 102) |
| rs8137254 | 22 | CTGTGCTCTGCGAAT CTGTGCTCTGCGAAT AGCTGCAGAAGTAACG TTGGGGACCCAAAATT AAAGCAGAATGCTAAAAAGCAGAATGCTAA TGTCAAGTCCTGAGA ACCAAGCCCTGGGAC TCTGGTGCCATTTCG GATTCTCCATGAGCA TGGT (SEQ ID NO: 47) | CTGTGCTCTGCGAATAGCT AGCTGCAGAAGTAACG TTGGGGACCCAAAAT SEQ ID NO: 103) TGTCAAGTCCTGAGA ACCAAGCCCTGGGAC TCTGGTGCCATTTTG GATTCTCCATGAGCA TGGT (SEQ ID NO: 48) | (rs8137254_c22_2_F; SEQ ID NO: 103) | ACCATGCTCATGGAGAATC C (rs8137254_c22_2_R; SEQ ID NO: 104) |
| rs3143 | 19 | TTTTTCCAGCCAACT CAAGGCCAAAAAAAC TTTCTTAATATAGTT ATTATGCGAGGGGAG GGGAAGCAAAGGAGC ACAGGTAGTCCACAG AATAAGACACAAGAAAAT ACCTCAAGCTGTG (SEQ ID NO: 49) | TTTTTCCAGCCAACTTTTTTCCAGCCAACTCAAG AAGGCCAAAAAAAAG TTTCTTAATATAGTT ATTATGCGAGGGGAGATTATGCGAGGGGAG GGGAAGCAAAGGAGCGGGAAGCAAAGGAGC ACAGGTAGTCCACAG AATAGGACACAAGAA ACCTCAAGCTGTG (SEQ ID NO: 50) | (rs3143_c19_2_F: SEQ ID NO: 105) | CACAGCTTGAGGTTTCTTG TG (rs3143_c19_2_R; SEQ ID NO: 106) |
| rs2182957 | 13 | TCTTCTCGTCCCCTATCTT AGCAAACAACATCCGAGCAAACAACATCG CTTGCTTCTGTCTGTCTTGCTTCTGTCTGT GTAACCACAGTGAATGTAACCACAGTGAAT GGGTGTGCACGCTTGGGGTGTGCACGCTTG ATGGGCCTCTGAGCC CCTGTTGCACAAACC AGAAA (SEQ ID NO: 51) | TCTTCTCGTCCCCTATCTTCTCGTCCCCTAAGCA CTTGCTTCTGTCTGT GGGTGTGCACGCTTG GTGGGCCTCTGAGCC CCTGTTGCACAAACC AGAAA (SEQ ID NO: 52) | (rs2182957_c13_1_F; SEQ ID NO: 107) | TTTCTGGTTTGTGCAACAG G (rs2182957_c13_1_R; SEQ ID NO: 108) |
| rs3739005 | 2 | CACATGGGGGCATTACACATGGGGGCATTACACATGGGGGCATTAAGAA AGAATCGCCCAGGGAAGAATCGCCCAGGGAT GGAGGAGGGAGAACGGGAGGAGGGGAGAACG CGTGCTTTTCACATTCGTGCTTTTCACATT TGCATTTGAATTTTCTGCATTTGAATTTTT | | ACATCGATGAGCACAAAAA CAC (rs3739005_c2_2_R; SEQ ID NO: 110) | |
| | | | | (rs3739005_c2_2_F; SEQ ID NO: 109) | |

TABLE 10-continued

Additional SNPs for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| | | GAGTTCCCAGGATGTGTTTTTGTGCTCATCGATGT (SEQ ID NO: 53) | GAGTTCCCAGGATGTGTTTTTGTGCTCATCGATGT (SEQ ID NO: 54) | | |
| rs530022 | 1 | GGGCTCTGAGGTGTGGGGCTCTGAGGTGTGTGAATGAAATAAAAACAAATGAAATAAAAACAAAATGTCCATGTCTGTCCTGTCCATGTCTGTCCTTTTATGGCATTTTGTTTTATGGCATTTTGGGACTTTACATTTCAGGACTTTACATTTCAAACATTTCAGACATGAACATTTCAGACATGTATCACAACACGAAGTATCACAACACGAGGGAATAACAGTTCCAGGAATAACAGTTCCAGGGATATCT (SEQ ID NO: 55) | GGGCTCTGAGGTGTGGGGCTCTGAGGTGTGTGAA (rs530022_c1_2_F; SEQ ID NO: 111) | AGATATCCCTGGAACTGTTATTCC (rs530022_c1_2_R; SEQ ID NO: 112) | |

Example 6

Identification of SNPs by Massively Parallel Sequencing of a Target Library: Determination of Fetal Fraction To determine the fraction of fetal cfDNA in a maternal sample, target polymorphic nucleic acid sequences each comprising a SNP were amplified and used for preparing a target library for sequencing in a massively parallel fashion.

cfDNA was extracted as described in Example 4. A target sequencing library was prepared as follows. cfDNA contained in 5 µl of purified cfDNA was amplified in a reaction volume of 50 µl containing 7.5 µl of a 1 µM primer mix (Table 1), 10 µl of NEB 5× Mastermix and 27 µl water. Thermal cycling was performed with the Gene Amp9700 (Applied Biosystems) using the following cycling conditions: incubating at 95° C. for 1 minute, followed by 20-30 cycles at 95° C. for 20 seconds, 68° C. for 1 minute, and 68° C. for 30s, which was followed by a final incubation at 68° C. for 5 minutes. A final hold at 4° C. was added until the samples were removed for combining with the unamplified portion of the purified cfDNA sample. The amplified product was purified using the Agencourt AMPure XP PCR purification system (Part No. A63881; Beckman Coulter Genomics, Danvers, Mass.). A final hold at 4° C. was added until the samples were removed for preparing the target library. The amplified product was analyzed with a 2100 Bioanalyzer (Agilent Technologies, Sunnyvale, Calif.), and the concentration of amplified product determined A sequencing library of amplified target nucleic acids was prepared as described in Example 2, and was sequenced in a massively parallel fashion using sequencing-by-synthesis with reversible dye terminators and according to the Illumina protocol (BioTechniques.RTM. Protocol Guide 2007 Published December 2006: p 29, and on the world wide web at biotechniques.com/default.asp?page=protocol&subsection=article_display&id=112378). Analysis and counting of tags mapped to a reference genome consisting of 26 sequences (13 pairs each representing two alleles) comprising a SNP i.e. SEQ ID NO:1-26 was performed as described.

Table 11 provides the tag counts obtained from sequencing the target library, and the calculated fetal fraction derived from sequencing data.

TABLE 11

Determination of Fetal Fraction by Massively Parallel Sequencing of a Library of Polymorphic Nucleic Acids

| SNP | SNP TAG COUNTS | Fetal Fraction (%) |
|---|---|---|
| rs10773760.1\|Chr.12\|length = 128\|allele = A | 236590 | 1.98 |
| rs10773760.2\|Chr.12\|length = 128\|allele = G | 4680 | |
| rs13182883.1\|Chr.5\|length = 111\|allele = A | 3607 | 4.99 |
| rs13182883.2\|Chr.5\|length = 111\|allele = G | 72347 | |
| rs4530059.1\|Chr.14\|length = 110\|allele = A | 3698 | 1.54 |
| rs4530059.2\|Chr.14\|length = 110\|allele = G | 239801 | |
| rs8078417.1\|Chr.17\|length = 110\|allele = C | 1E+06 | 3.66 |
| rs8078417.2\|Chr.17\|length = 110\|allele = T | 50565 | |

Fetal Fraction (Mean ± S.D.) = 12.4 ± 6.6

The results show that polymorphic nucleic acid sequences each comprising at least one SNP can be amplified from cfDNA derived from a maternal plasma sample to construct a library that can be sequenced in a massively parallel fashion to determine the fraction of fetal nucleic acids in the maternal sample.

Example 7

Identification of SNPs Following Enrichment of Fetal and Maternal Nucleic Acids in a cfDNA Sequencing Library Sample: Determination of Fetal Fraction To enrich the fetal and maternal cfDNA contained in a primary sequencing library constructed using purified fetal and maternal cfDNA, a portion of a purified cfDNA sample was used for amplifying polymorphic target nucleic acid sequences, and for preparing a sequencing library of amplified polymorphic target nucleic acids, which was used to enrich the fetal and maternal nucleic acid sequences comprised in the primary library.

Figure 5:
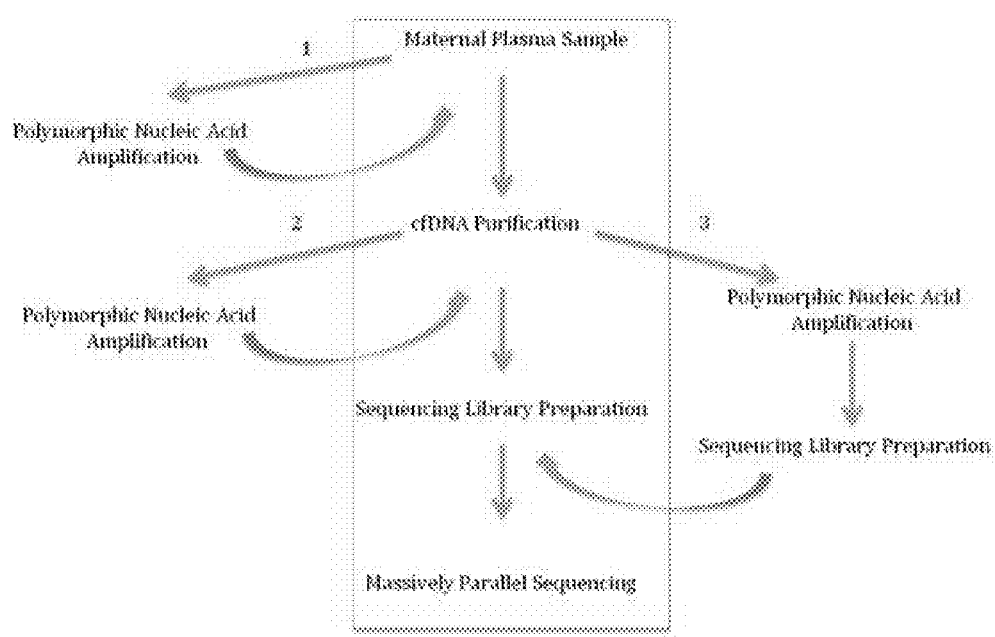
FIG. 5 is a flowchart outlining alternative methods used for determining fetal fraction by massively parallel sequencing as described in Examples 6-9.

The method corresponds to workflow 3 diagrammed in FIG. 5. A target sequencing library was prepared from a portion of the purified cfDNA as described in Example 2. A primary sequencing library was prepared using the remaining portion of the purified cfDNA as described in Example 4. Enrichment of the primary library for the amplified polymorphic nucleic acids comprised in the target library was obtained by diluting the primary and the target sequencing libraries to 10 nM, and combining the target library with the primary library at a ratio of 1:9 to provide an enriched sequencing library. Sequencing of the enriched library and analysis of the sequencing data was performed as described in Example 4.

sample that was utilized for determining the corresponding fetal fraction. Method for using sequence tags counts for determining aneuploidy are described in pending U.S. patent application Ser. Nos. 12/958,352, 12/958,356 and 12/958,353, which are herein incorporated by reference in their entirety.

TABLE 12

Determination of Fetal Fraction by Massively Parallel Sequencing of an Enriched Library of Polymorphic Nucleic Acids

| Sample ID (karyotype) | SNP | SNP TAG COUNTS | FETAL FRACTION (%) |
|---|---|---|---|
| 11409 (47, XY + 21) | rs13182883.1\|Chr.5\|length = 111\|allele = A | 261 | 4.41 |
| | rs13182883.2\|Chr.5\|length = 111\|allele = G | 5918 | |
| | rs740598.1\|Chr.10\|length = 114\|allele = A | 5545 | 7.30 |
| | rs740598.2\|Chr.10\|length = 114\|allele = G | 405 | |
| | rs8078417.1\|Chr.17\|length = 110\|allele = C | 8189 | 6.74 |
| | rs8078417.2\|Chr.17\|length = 110\|allele = T | 121470 | |
| | rs576261.1\|Chr.19\|length = 114\|allele = A | 58342 | 7.62 |
| | rs576261.2\|Chr.19\|length = 114\|allele = C | 4443 | |

Fetal Fraction (Mean ± S.D.) = 6.5 ± 1.5

| Sample ID | | | |
|---|---|---|---|
| 95133 (47, XX + 18) | rs1109037.1\|Chr.2\|length = 126\|allele = A | 12229 | 2.15 |
| | rs1109037.2\|Chr.2\|length = 126\|allele = G | 263 | |
| | rs13218440.1\|Chr.6\|length = 139\|allele = A | 55949 | 3.09 |
| | rs13218440.2\|Chr.6\|length = 139\|allele = G | 1729 | |
| | rs7041158.1\|Chr.9\|length = 117\|allele = C | 7281 | 4.12 |
| | rs7041158.2\|Chr.9\|length = 117\|allele = T | 300 | |
| | rs7205345.1\|Chr.16\|length = 116\|allele = C | 53999 | 2.14 |
| | rs7205345.2\|Chr.16\|length = 116\|allele = G | 1154 | |

Fetal Fraction (Mean ± S.D.) = 2.9 ± 0.9

| Sample ID | | | |
|---|---|---|---|
| 51236 (46, XY + 13) | rs13218440.1\|Chr.6\|length = 139\|allele = A | 1119 | 1.65 |
| | rs13218440.2\|Chr.6\|length = 139\|allele = G | 67756 | |
| | rs560681.1\|Chr.1\|length = 111\|allele = A | 14123 | 5.18 |
| | rs560681.2\|Chr.1\|length = 111\|allele = G | 732 | |
| | rs7205345.1\|Chr.16\|length = 116\|allele = C | 18176 | 1.63 |
| | rs7205345.2\|Chr.16\|length = 116\|allele = G | 296 | |
| | rs9866013.1\|Chr.3\|length = 121\|allele = C | 117 | 2.33 |
| | rs9866013.2\|Chr.3\|length = 121\|allele = T | 5024 | |

Fetal Fraction (Mean ± S.D.) = 2.7 ± 1.7

| Sample ID | | | |
|---|---|---|---|
| 54430 (45, XO) | rs1109037.1\|Chr.2\|length = 126\|allele = A | 19841 | 1.80 |
| | rs1109037.2\|Chr.2\|length = 126\|allele = G | 357 | |
| | rs9866013.1\|Chr.3\|length = 121\|allele = C | 12931 | 3.81 |
| | rs9866013.2\|Chr.3\|length = 121\|allele = T | 493 | |
| | rs7041158.1\|Chr.9\|length = 117\|allele = C | 2800 | 4.25 |
| | rs7041158.2\|Chr.9\|length = 117\|allele = T | 119 | |
| | rs740598.1\|Chr.10\|length = 114\|allele = A | 12903 | 4.87 |
| | rs740598.2\|Chr.10\|length = 114\|allele = G | 628 | |
| | rs10773760.1\|Chr.12\|length = 128\|allele = A | 46324 | 4.65 |
| | rs10773760.2\|Chr.12\|length = 128\|allele = G | 2154 | |

Fetal Fraction (Mean ± S.D.) = 3.9 ± 1.2

Table 12 provides the number of sequence tags that mapped to the SNP genome for the informative SNPs identified from sequencing an enriched library derived from plasma samples of pregnant women each carrying a T21, a T13, a T18 and a monosomy X fetus, respectively. Fetal fraction was calculated as follows:

% fetal fraction allele$_x$=(($\Sigma$Fetal sequence tags for allele$_x$)/($\Sigma$Maternal sequence tags for allele$_x$))×100

Table 4 also provides the number of the sequence tags mapped to the human reference genome. Tags mapped to the human reference genome were used to determine the presence or absence of aneuploidy using the same plasma Example 8

Identification of SNPs by Massively Parallel Sequencing: Enrichment of Fetal and Maternal Nucleic Acids for Polymorphic Nucleic Acids in a Purified cfDNA Sample and Determination of Fetal Fraction To enrich the fetal and maternal cfDNA contained in a purified sample of cfDNA extracted from a maternal plasma sample, a portion of the purified cfDNA was used for amplifying polymorphic target nucleic acid sequences each comprising one SNP chosen from the panel of SNPs given in Table 9.

The method corresponds to workflow 2 diagrammed in FIG. 4. Cell-free plasma was obtained from a maternal blood sample, and cfDNA was purified from the plasma sample as described in Example 4. The final concentration was determined to be 92.8 pg/µl. cfDNA contained in 5 µl of purified cfDNA was amplified in a reaction volume of 50 µl containing 7.5 µl of a 1 uM primer mix (Table 9), 10 µl of NEB 5× Mastermix and 27 µl water. Thermal cycling was performed with the Gene Amp9700 (Applied Biosystems). Using the following cycling conditions: incubating at 95° C. for 1 minute, followed by 30 cycles at 95° C. for 20 seconds, 68° C. for 1 minute, and 68° C. for 30s, which was followed by a final incubation at 68° C. for 5 minutes. A final hold at 4° C. was added until the samples were removed for combining with the unamplified portion of the purified cfDNA sample. The amplified product was purified using the Agencourt AMPure XP PCR purification system (Part No. A63881; Beckman Coulter Genomics, Danvers, Mass.), and the concentration quantified using the Nanodrop 2000 (Thermo Scientific, Wilmington, Del.). The purified amplification product was diluted 1:10 in water and 0.9 µl (371 pg) added to 40 µl of purified cfDNA sample to obtain a 10% spike. The enriched fetal and maternal cfDNA present in the purified cfDNA sample was used for preparing a sequencing library, and was sequenced as described in Example 4.

Table 13 provides the tag counts obtained for each of chromosomes 21, 18, 13, X and Y i.e. sequence tag density, and the tag counts obtained for the informative polymorphic sequences contained in the SNP reference genome. i.e. SNP tag density. The data show that sequencing information can be obtained from sequencing a single library constructed from a purified maternal cfDNA sample that has been enriched for sequences comprising SNPs to simultaneously determine the presence or absence of aneuploidy and the fetal fraction. The presence or absence of aneuploidy was determined using the number of tags mapped to chromosomes as described in pending U.S. patent application Ser. Nos. 12/958,352. In the example given, the data show that the fraction of fetal DNA in plasma sample AFR105 was quantifiable from the sequencing results of five informative SNPs and determined to be 3.84%. Sequence tag densities are provided for chromosomes 21, 13, 18, X and Y.

The example shows that the enrichment protocol provides the requisite tag counts for determining aneuploidy and fetal fraction from a single sequencing process.

TABLE 13

Determination of Fetal Fraction by Massively Parallel Sequencing: Enrichment of Fetal and Maternal Nucleic Acids for Polymorphic Nucleic Acids in a Purified cfDNA sample

| Aneuploidy | | | | | |
|---|---|---|---|---|---|
| | Chromosome 21 | Chromosome 18 | Chromosome 13 | Chromosome X | Chromosome Y |
| Sequence Tag Density | 178763 | 359529 | 388204 | 572330 | 2219 |
| Karyotype | Unaffected | Unaffected | Unaffected | Unaffected | Unaffected |

| Fetal Fraction | | |
|---|---|---|
| SNP | SNP TAG DENSITY | FETAL FRACTION (%) |
| rs10773760.1|Chr.12|length = 128|allele = A | 18903 | 2.81 |
| rs10773760.2|Chr.12|length = 128|allele = G | 532 | |
| rs1109037.1|Chr.2|length = 126|allele = A | 347 | 5.43 |
| rs1109037.2|Chr.2|length = 126|allele = G | 6394 | |
| rs2567608.1|Chr.20|length = 110|allele = A | 94503 | 1.74 |
| rs2567608.2|Chr.20|length = 110|allele = G | 1649 | |
| rs7041158.1|Chr.9|length = 117|allele = C | 107 | 5.61 |
| rs7041158.2|Chr.9|length = 117|allele = T | 6 | |
| rs8078417.1|Chr.17|length = 110|allele = C | 162668 | 3.61 |
| rs8078417.2|Chr.17|length = 110|allele = T | 5877 | |

Fetal Fraction (Mean ± S.D.) = 3.8 ± 1.7

Example 9

Identification of SNPs by Massively Parallel Sequencing: Enrichment of Fetal and Maternal Nucleic Acids for Polymorphic Nucleic Acids in a Plasma Sample and Determination of Fetal Fraction To enrich the fetal and maternal cfDNA contained in an original plasma sample derived from a pregnant woman, a portion the original plasma sample was used for amplifying polymorphic target nucleic acid sequences each comprising one SNP chosen from the panel of SNPs given in Table 9, and a portion of the amplified product was combined with the remaining original plasma sample.

The method corresponds to workflow 1 diagrammed in FIG. 5. cfDNA contained in 15 µl of cell-free plasma was amplified in a reaction volume of 50 µl containing 9 ul of a 1 µM mixture of primers (15 plex Table 9), 1 µl of Phusion blood DNA polymerase, 25 ul of the 2× Phusion blood PCR buffer containing deoxynucleotide triphosphates (dNTPs: dATP, dCTP, dGTP and dTTP). Thermal cycling was performed with the Gene Amp9700 (Applied Biosystems) using the following cycling conditions: incubating at 95° C. for 3 minutes, followed by 35 cycles at 95° C. for 20 seconds, 55° C. for 30s, and 70° C. for 1 minute, which was followed by a final incubation at 68° C. for 5 minutes. A final hold at 4° C. was added until the samples were removed for combining with the unamplified portion of the cell-free plasma. The amplified product was diluted 1:2 with water and analyzed using the Bioanalyzer. An additional 3 µl of amplified product was diluted with 11.85 µl of water to obtain a final concentration of 2 ng/µl. 2.2 µl of the diluted amplified product was combined with the remaining plasma sample. The enriched fetal and maternal cfDNA present in the plasma sample was purified as described in Example 4, and used for preparing a sequencing library. Sequencing and analysis of the sequencing data was performed as described in Example 4.

The results are given in Table 14. In the example given, the data show that the fraction of fetal DNA in plasma sample SAC2517 was quantifiable from the sequencing results of one informative SNP and determined to be 9.5%. In the example given, sample SAC2517 was shown by karyotyping to be unaffected for aneuploidies of chromosomes 21, 13, 18, X and Y. Sequence tag densities are provided for chromosomes 21, 13, 18, X and Y. The presence or absence of aneuploidy was determined using tag counts as described in U.S. Provisional Applications 61/407,017 and 61/455,849, which are herein incorporated by reference in their entirety.

The example demonstrates that enriching the mixture of fetal and maternal cfDNA present in a plasma sample for nucleic acid sequences that comprise at least one informative SNP can be used to provide the requisite sequence and SNP tag counts for determining aneuploidy and fetal fraction from a single sequencing process by massively parallel sequencing a library prepared from cfDNA contained in a plasma sample that is enriched for polymorphic nucleic acids.

rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672. The primers used for amplifying the target sequences comprising the tandem SNPs are designed to encompass both SNP sites. For example, the forward primer is designed to encompass the first SNP, and the reverse primer is designed to encompass the second of the tandem SNP pair i.e. each of the SNP sites in the tandem pair is encompassed within the 36 bp generated by the sequencing method. Paired-end sequencing can be used to identify all sequences encompassing the tandem SNP sites. Exemplary sets of primers that are used to amplify the tandem SNPs disclosed herein are rs7277033-rs2110153_F: TCCTGGAAACAAAAGTATT (SEQ ID NO:197) and rs7277033-rs2110153_R: AACCTTACAACAAAGCTA-GAA (SEQ ID NO:198), set rs2822654-rs1882882_F: ACT-AAGCCTTGGGGATCCAG (SEQ ID NO:199) and rs2822654-rs1882882_R: TGCTGTG-GAAATACTAAAAGG (SEQ ID NO:200), set rs368657-rs376635_F:CTCCAGAGGTAATCCTGTGA (SEQ ID

TABLE 14

Determination of Fetal Fraction by Massively Parallel Sequencing: Enrichment of Fetal and Maternal Nucleic Acids for Polymorphic Nucleic Acids Comprising a SNP in a Plasma Sample

| Aneuploidy | | | | | |
|---|---|---|---|---|---|
| | Chromosome 21 | Chromosome 18 | Chromosome 13 | Chromosome X | Chromosome Y |
| Sequence Tag Density | 183851 | 400582 | 470526 | 714055 | 2449 |
| Karyotype | Unaffected | Unaffected | Unaffected | Unaffected | Unaffected |

| Fetal Fraction | | |
|---|---|---|
| SNP | TAG COUNTS | FETAL FRACTION (%) |
| rs10773760.1|Chr.12|length = 128|allele = A | 8536 | 9.5 |
| rs10773760.2|Chr.12|length = 128|allele = G | 89924 | |

To determine the fraction of fetal cfDNA in a maternal sample, target polymorphic nucleic acid sequences each comprising a pair of tandem SNPs are amplified and used for preparing a target library for sequencing in a massively parallel fashion. Pairs of tandem SNPs can be selected from rs7277033-rs2110153; rs2822654-rs1882882; rs368657-rs376635; rs2822731-rs2822732; rs1475881-rs7275487; rs1735976-rs2827016; rs447340-rs2824097; rs418989-rs13047336; rs987980- rs987981; rs4143392- rs4143391; rs1691324- rs13050434; rs11909758-rs9980111; rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102- rs458848; rs961301-rs2830208; rs2174536-rs458076; rs11088023-rs11088024; rs1011734-rs1011733; rs2831244-rs9789838; rs8132769-rs2831440; rs8134080-rs2831524; rs4817219-rs4817220; rs2250911-rs2250997; rs2831899-r52831900; rs2831902-rs2831903; rs11088086-rs2251447; rs2832040-rs11088088; rs2832141-

NO:201) and rs368657-rs376635_R:TGGTGTGAGATGG-TATCTAGG (SEQ ID NO:202), rs2822731-rs2822732_F: GTATAATCCATGAATCTTGTTT (SEQ ID NO:203) and rs2822731-rs2822732_R:TTCAAATTGTATATAAGA-GAGT (SEQ ID NO:204), rs1475881-rs7275487_F:GCA-GGAAAGTTATTTTTAAT (SEQ ID NO:205) and rs1475881-rs7275487_R:TGCTT-GAGAAAGCTAACACTT (SEQ ID NO:206), rs1735976-rs2827016_F:CAGTGTTTGGAAATTGTCTG (SEQ ID NO:207) and rs1735976-rs2827016_R:GGCACTGGGA-GATTATTGTA (SEQ ID NO:208), rs447349-rs2824097_F: TCCIGTTGTTAAGTACACAT (SEQ ID NO:209) and rs447349-rs2824097_R:GGGCCGTAATTACTTTTG (SEQ ID NO:210), rs418989-rs13047336_F:ACTCAGTAG-GCACTTIGTGTC (SEQ ID NO:211) and rs418989-rs13047336_R:TCTTCCACCACACCAATC (SEQ ID NO:212), rs987980-rs987981_F:TGGCTTTTTCAAAGG-TAAAA (SEQ ID NO:213) and rs987980-rs987981_R: GCAACGTTAACATCTGAATTT (SEQ ID NO:214), rs4143392-rs4143391_F: rs4143392- rs4143391 (SEQ ID NO:215) and rs4143392-rs4143391_R:ATTTTATATGT-CATGATCTAAG (SEQ ID NO:216), rs1691324-rs13050434_F: AGAGATTACAGGTGTGAGC (SEQ ID NO:217) and rs1691324-rs13050434_R: ATGATCCT-CAACTGCCTCT (SEQ ID NO:218), rs11909758-rs9980111_F: TGAAACTCAAAAGAGAAAAG (SEQ ID NO:219) and rs11909758-rs9980111_R: ACAGATTTC-TACTTAAAATT (SEQ ID NO:220), rs2826842-rs232414_F: TGAAACTCAAAAGAGAAAAG (SEQ ID NO:221) and rs2826842-rs232414_R: ACAGATTTCTACT-TAAAATT (SEQ ID NO:222), rs2826842-rs232414_F: GCAAAGGGGTACTCTATGTA (SEQ ID NO:223) and rs2826842-rs232414_R: TATCGGGTCATCTTGTTAAA (SEQ ID NO:224), rs1980969-rs1980970_F: TCTAACAAAGCTCTGTCCAAAA (SEQ ID NO:225) and rs1980969-rs1980970_R: CCACACTGAATAACTG-GAACA (SEQ ID NO:226), rs9978999-rs9979175_F: GCAAGCAAGCTCTCTACCTTC (SEQ ID NO:227) and rs9978999-rs9979175_R: TGTTCTTCCAAAATTCA-CATGC (SEQ ID NO:228), rs1034346-rs12481852_F: ATTTCACTATTCCTTCATTTT (SEQ ID NO:229) and rs1034346-rs12481852_R: TAATTGTTGCACACTAAAT-TAC (SEQ ID NO:230), rs4817013-rs7277036_F: AAAAAGCCACAGAAATCAGTC (SEQ ID NO:231) and rs4817013-rs7277036_R: TTCTTATATCT-CACTGGGCATT (SEQ ID NO:232), rs9981121-rs2829696_F: GGATGGTAGAAGAGAAGAAAGG (SEQ ID NO:233) and rs9981121-rs2829696_R: GGATGGTA-GAAGAGAAGAAAGG (SEQ ID NO:234), rs455921-rs2898102_F: TGCAAAGATGCAGAACCAAC (SEQ ID NO:235) and rs455921-rs2898102_R: TTTTGTTCCTT-GTCCTGGCTGA (SEQ ID NO:236), rs2898102-rs458848_F: TGCAAAGATGCAGAACCAAC (SEQ ID NO:237) and rs2898102- rs458848_R: GCCTCCAGCTC-TATCCAAGTT (SEQ ID NO:238), rs961301-rs2830208_F: CCTTAATATCTTCCCATGTCCA (SEQ ID NO:239) and rs961301-rs2830208_R: ATTGTTAGTGCCTCTTCT-GCTT (SEQ ID NO:240), rs2174536-rs458076_F: GAGAAGTGAGGTCAGCAGCT (SEQ ID NO:241) and rs2174536-rs458076_R: TTTCTAAATTTCCATT-GAACAG (SEQ ID NO:242), rs11088023-rs11088024_F: GAAATTGGCAATCTGATTCT (SEQ ID NO:243) and rs11088023-rs11088024_R: CAACTTGTCCTTTATT-GATGT (SEQ ID NO:244), rs1011734-rs1011733_F: CTATGTTGATAAAACATTGAAA (SEQ ID NO:245) and rs1011734-rs1011733_R: GCCTGTCTGGAATATAGTTT (SEQ ID NO:246), rs2831244-rs9789838_F: CAGGGCATATAATCTAAGCTGT (SEQ ID NO:247) and rs2831244-rs9789838_R: CAATGACTCTGAGTTGAG-CAC (SEQ ID NO:248), rs8132769-rs2831440_F: ACTCTCTCCCTCCCCTCT (SEQ ID NO:249) and rs8132769-rs2831440_R: TATGGCCCCAAAACTATTCT (SEQ ID NO:250), rs8134080-rs2831524_F: ACAAG-TACTGGGCAGATTGA (SEQ ID NO:251) and rs8134080-rs2831524_R: GCCAGGTTTAGCTTTCAAGT (SEQ ID NO:252), rs4817219-rs4817220_F: TTTTATATCAGGA-GAAACACTG (SEQ ID NO:253) and rs4817219-rs4817220_R: CCAGAATTTTGGAGGTTTAAT (SEQ ID NO:254), rs2250911-rs2250997_F: TGTCATTCCTCCTT-TATCTCCA (SEQ ID NO:255) and rs2250911-rs2250997_R: TTCTTTTGCCTCTCCCAAAG (SEQ ID NO:256), rs2831899-rs2831900_F: ACCCTGGCACAGT-GTTGACT (SEQ ID NO:257) and rs2831899-rs2831900_R: TGGGCCTGAGTTGAGAAGAT (SEQ ID NO:258), rs2831902-rs2831903_F: AATTTGTAAGTAT-GTGCAACG (SEQ ID NO:259) and rs2831902-rs2831903_R: TTTTTCCCATTTCCAACTCT (SEQ ID NO:260), rs11088086-rs2251447_F: AAAAGAT-GAGACAGGCAGGT (SEQ ID NO:261) and rs11088086-rs2251447_R: ACCCCTGTGAATCTCAAAAT (SEQ ID NO:262), rs2832040-rs11088088_F: GCACTTGCTTCT-ATTGTTTGT (SEQ ID NO:263) and rs2832040-rs11088088_R: CCCTTCCTCTCTTCCATTCT (SEQ ID NO:264), rs2832141-rs2246777_F: AGCACTGCAGGTA (SEQ ID NO:265) and rs2832141-rs2246777_R: ACAGA-TACCAAAGAACTGCAA (SEQ ID NO:266), rs2832959-rs9980934_F: TGGACACCTTTCAACTTAGA (SEQ ID NO:267) and rs2832959-rs9980934_R: GAACAGTAAT-GTTGAACTTTTT (SEQ ID NO:268), rs2833734-rs2833735_F: TCTTGCAAAAAGCTTAGCACA (SEQ ID NO:269) and rs2833734-rs2833735_R: AAAAAGATCT-CAAAGGGTCCA (SEQ ID NO:270), rs933121-rs933122_F: GCTTTTGCTGAACATCAAGT (SEQ ID NO:271) and rs933121-rs933122_R: CCTTCCAGCAG-CATAGTCT (SEQ ID NO:272), rs2834140-rs12626953_F: AAATCCAGGATGTGCAGT (SEQ ID NO:273) and rs2834140-rs12626953_R: ATGATGAGGTCAGTGGTGT (SEQ ID NO:274), rs2834485-rs3453_F: CATCACAGAT-CATAGTAAATGG (SEQ ID NO:275) and rs2834485-rs3453_R: AATTATTATTTTGCAGGCAAT (SEQ ID NO:276), rs9974986-rs2834703_F: CATGAG-GCAAACACCTTTCC (SEQ ID NO:277) and rs9974986-rs2834703_R: GCTGGACTCAGGATAAAGAACA (SEQ ID NO:278), rs2776266-rs2835001_F: TGGAAGCCT-GAGCTGACTAA (SEQ ID NO:279) and rs2776266-rs2835001_R:CCTTCTTTTCCCCCAGAATC (SEQ ID NO:280), rs1984014-rs1984015_F:TAGGAGAACA-GAAGATCAGAG (SEQ ID NO:281) and rs1984014-rs1984015_R:AAAGACTATTGCTAAATGCTTG (SEQ ID NO:282), rs7281674-rs2835316_F: TAAGCGTAGGGCT-GTGTGTG (SEQ ID NO:283) and rs7281674-rs2835316_R: GGACGGATAGACTCCAGAAGG (SEQ ID NO:284), rs13047304-rs13047322_F: GAATGACCT-TGGCACTTTTATCA (SEQ ID NO:285) and rs13047304-rs13047322_R: AAGGATAGAGATATACAGAT-GAATGGA (SEQ ID NO:286), rs2835735-rs2835736_F: CATGCACCGCGCAAATAC (SEQ ID NO:287) and rs2835735-rs2835736_R: ATGCCTCACCCACAAACAC (SEQ ID NO:288), rs13047608-rs2835826_F: TCCAAGC-CCTTCTCACTCAC (SEQ ID NO:289) and rs13047608-rs2835826_R: CTGGGACGGTGACATTTTCT (SEQ ID NO:290), rs2836550-rs2212596_F: CCCAGGAAGAGTG-GAAAGATT (SEQ ID NO:291) and rs2836550-rs2212596_R: TTAGCTTGCATGTACCTGTGT (SEQ ID NO:292), rs2836660-rs2836661_F: AGCTAGATGGGGT-GAATTTT (SEQ ID NO:293) and _R: TGGGCT-GAGGGGAGATTC (SEQ ID NO:294), rs465612-rs8131220_F: ATCAAGCTAATTAATGTTATCT (SEQ ID NO:295) and rs465612-rs8131220_R: AAT-GAATAAGGTCCTCAGAG (SEQ ID NO:296), rs9980072-rs8130031_F:TTTAATCTGATCATTGCCCTA (SEQ ID NO:297) and rs9980072-rs8130031_R: AGCT-GTGGGTGACCTTGA (SEQ ID NO:298), rs418359-rs2836926_F: TGTCCCACCATTGTGTATTA (SEQ ID NO:299) and rs418359-rs2836926_R: TCAGACTT-GAAGTCCAGGAT (SEQ ID NO:300), rs7278447-rs7278858_F: GCTTCAGGGGTGTTAGTTTT (SEQ ID NO:301) and rs7278447-rs7278858_R: CTTTGT-GAAAAGTCGTCCAG (SEQ ID NO:302), rs385787-rs367001_F:CCATCATGGAAAGCATGG (SEQ ID NO:303) and rs385787-rs367001_R: TCATCTCCAT-GACTGCACTA (SEQ ID NO:304), rs367001-rs386095_F: GAGATGACGGAGTAGCTCAT (SEQ ID NO:305) and rs367001-rs386095_R: CCCAGCTGCACTGTCTAC (SEQ ID NO:306), rs2837296-rs2837297_F: TCTTGTTCCAAT-CACAGGAC (SEQ ID NO:307) and rs2837296-rs2837297_R: ATGCTGTTAGCTGAAGCTCT (SEQ ID NO:308), and rs2837381-rs4816672_F: TGAAAGCTC-CTAAAGCAGAG (SEQ ID NO:309) and rs2837381-rs4816672_R:TTGAAGAGATGTGCTATCAT (SEQ ID NO:310). Polynucleotide sequences e.g. GC clamp sequences, can be included to ensure specific hybridization of AT-rich primers (Ghanta et al., PLOS ONE 5(10): doi10.1371/journal.pone.0013184 [2010], available on the world wide web at plosone.org). An example of a GC clamp sequence that can be included either 5' of the forward primer or 3' of the reverse primer is GCCGCCTGCAGCCCGCGC-CCCCCGTGCCCCCGCCCCGCCGCCGGCCCGGGCGC C (SEQ ID NO:311). Polymorphic sequences can be used alone or in combination with unamplified cfDNA to determine either fetal fraction or the presence or absence of aneuploidy and fetal fraction in a maternal sample as described for polymorphic SNP sequences. Sample preparation and enrichment of cfDNA sequencing library, a purified cfDNA sample, and a plasma sample is performed according to the method described in Examples 7, 8, and 9, respectively.

All sequencing libraries are prepared as described in Example 4b., and sequencing is performed as described in Example 4c. Analysis of the sequencing data for the determination of fetal aneuploidy is performed as described in pending U.S. patent application Ser. No. 12/958,352, filed on Dec. 1, 2010. Concomitant to the analysis for determining aneuploidy, the sequencing data is analyzed to determine the fetal fraction as follows. Following the transfer of the image and base call files to the Unix server running the Illumina "Genome Analyzer Pipeline" software version 1.51 as described in Example 4d., the 36 bp reads are aligned to a 'tandem SNP genome' using the BOWTIE program. The tandem SNP genome is identified as the grouping of the DNA sequences that encompass the alleles of the 58 tandem SNP pairs disclosed above. Only reads that mapped uniquely to the tandem SNP genome are used for the analysis of fetal fraction. Reads that match perfectly to the tandem SNP genome are counted as tags and filtered. Of the remaining reads, only reads having one or two mismatches are counted as tags and included in the analysis. Tags mapped to each of the tandem SNP alleles are counted, and the fetal fraction is determined essentially as described in Example 9 above but accounting for tags mapped to the two tandem SNP alleles x and y present on each of the amplified polymorphic target nucleic acid sequences that are amplified to enrich the samples i.e.

% fetal fraction $allele_x = ((\Sigma Fetal\ sequence\ tags\ for\ allele_{x+y})/(\Sigma Maternal\ sequence\ tags\ for\ allele_{x+y})) \times 100$ Only informative tandem SNPs are used to determine the fetal fraction.

Optionally, the fraction of fetal nucleic acids in the mixture of fetal and maternal nucleic acids is calculated for each of the informative allele ($allele_{x+y}$) as follows:

% fetal fraction $allele_{x+y} = ((2 \times \Sigma Fetal\ sequence\ tags\ for\ allele_{x+y})/(\Sigma Maternal\ sequence\ tags\ for\ allele_{x+y})) \times 100$, to compensate for the presence of 2 sets of tandem fetal alleles, one being masked by the maternal background.

The percent fetal fraction is calculated for at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or more informative sets of tandem alleles. In one embodiment, the fetal fraction is the average fetal fraction determined for at least 3 informative sets of tandem alleles.

Example 11

Identification of Fetal STRs by Massively Parallel Sequencing: Determination of Fetal Fraction To determine the fraction of fetal cfDNA in a maternal sample, target polymorphic nucleic acid sequences each comprising an STR are amplified and used for preparing a target library for sequencing in a massively parallel fashion.

Peripheral blood samples are obtained from pregnant subjects, and cfDNA is purified from the plasma fraction as described in Example 4. STRs that are amplified are chosen from the codis and non-codis STRs disclosed in Table 14, and amplification of the polymorphic STR sequences is obtained using the corresponding sets of primers provided. For example, the STRs listed in Table 15 are amplified using the corresponding primers (SEQ ID NOs: 113-197), and the amplified product is used to generate a target sequencing library. The STR target sequencing library is prepared as described for the preparation of the SNP target library as described in Example 8. STRs CSF1PO, D13S317, D16S539, D18S51, D21S11, D2S1338, D7S820, and FGA have been analyzed previously for determining fetal fraction, and are disclosed in US Provisional applications 61/296,358 and 61/360,837.

TABLE 15

CODIS and NON-CODIS miniSTRs

| STR Locus (Marker Name) | Chromosome Location | Size Range (bp) | GenBank Accession | Primer Sequences (Forward/Reverse) |
|---|---|---|---|---|
| Codis minoSTR loci* | | | | |
| CSF1PO | 5q33.1 | 89-129 | X14720 | ACAGTAACTGCCTTCATAGATAG (CSF1PO_F; SEQ ID NO: 113) GTGTCAGACCCTGTTCTAAGTA (CSF1PO_R; SEQ ID NO: 114) |
| FGA | 4q31.3 | 125-281 | M64982 | AAATAAAATTAGGCATATTTACAAGC (FGA_F; SEQ ID NO: 115) GCTGAGTGATTTGTCTGTAATTG (FGA_R; SEQ ID NO: 116) |

TABLE 15-continued

CODIS and NON-CODIS miniSTRs

| STR Locus (Marker Name) | Chromosome Location | Size Range (bp) | GenBank Accession | Primer Sequences (Forward/Reverse) |
|---|---|---|---|---|
| TH01 | 11p15.5 | 51-98 | D00269 | CCTGTTCCTCCCTTATTTCCC (TH01_F; SEQ ID NO: 117) GGGAACACAGACTCCATGGTG (TH01_R; SEQ ID NO: 118) |
| TPOX | 2p25.3 | 65-101 | M68651 | CTTAGGGAACCCTCACTGAATG (TPOX_F; SEQ ID NO: 119) GTCCTTGTCAGCGTTTATTTGC (TPOX_R; SEQ ID NO: 120) |
| vWA | 12p13.31 | 88-148 | M25858 | AATAATCAGTATGTGACTTGGATTGA (vWA_F; SEQ ID NO: 121) ATAGGATGGATGGATAGATGGA (vWA_R; SEQ ID NO: 122) |
| D3S1358 | 3p21.31 | 72-120 | NT_005997 | CAGAGCAAGACCCTGTCTCAT (D3S1358_F; SEQ ID NO: 123) TCAACAGAGGCTTGCATGTAT (D3S1358_R; SEQ ID NO: 124) |
| D5S818 | 5q23.2 | 81-117 | AC008512 | GGGTGATTTTCCTCTTTGGT (D5S818_F; SEQ ID NO: 125) AACATTTGTATCTTTATCTGTATCCTTATTTAT (D5S818_R; SEQ ID NO: 126) |
| D7S820 | 7q21.11 | 136-176 | AC004848 | GAACACTTGTCATAGTTTAGAACGAAC (D7S820_F; SEQ ID NO: 127) TCATTGACAGAATTGCACCA (D7S820_R; SEQ ID NO: 128) |
| D8S1179 | 8q24.13 | 86-134 | AF216671 | TTTGTATTTCATGTGTACATTCGTATC (D7S820_F; SEQ ID NO: 129) ACCTATCCTGTAGATTATTTTCACTGTG (D7S820_R; SEQ ID NO: 130) |
| D13S317 | 13q31.1 | 88-132 | AL353628 | TCTGACCCATCTAACGCCTA (D13S317_F; SEQ ID NO: 131) CAGACAGAAAGATAGATAGATGATTGA (D13S317_R; SEQ ID NO: 132) |
| D16S539 | 16q24.1 | 81-121 | AC024591 | ATACAGACAGACAGACAGGTG (D16S539_F; SEQ ID NO: 133) GCATGTATCTATCATCCATCTCT (D16S539_R; SEQ ID NO: 134) |
| D18S51 | 18q21.33 | 113-193 | AP001534 | TGAGTGACAAATTGAGACCTT (D18S51_F; SEQ ID NO: 135) GTCTTACAATAACAGTTGCTACTATT (D18S51_R; SEQ ID NO: 136) |
| D21S11 | 21q21.1 | 153-221 | AP000433 | ATTCCCCAAGTGAATTGC (D21S11_F; SEQ ID NO: 137) GGTAGATAGACTGGATAGATAGACGA (D21S11_R; SEQ ID NO: 138) |
| D2S1338 | 2q35 | 90-142 | AC01036 | TGGAAACAGAAATGGCTTGG (D2S1338_F; SEQ ID NO: 139) GATTGCAGGAGGGAAGGAAG (D2S1338_R; SEQ ID NO: 140) |
| Penta D | 21q22.3 | 94-167 | AP001752 | GAGCAAGACACCATCTCAAGAA (Penta D_F; SEQ ID NO: 141) GAAATTTTACATTTATGTTTATGATTCTCT (Penta D_R; SEQ ID NO: 142) |
| Penta E | 15q26.2 | 80-175 | AC027004 | GGCGACTGAGCAAGACTC (Penta E_F; SEQ ID NO: 143) GGTTATTAATTGAGAAAACTCCTTACA (Penta E_R; SEQ ID NO: 144) |

TABLE 15-continued

CODIS and NON-CODIS miniSTRs

| STR Locus (Marker Name) | Chromosome Location | Size Range (bp) | GenBank Accession | Primer Sequences (Forward/Reverse) |
|---|---|---|---|---|
| colspan="5" | Non-Codis miniSTR loci* |

| STR Locus (Marker Name) | Chromosome Location | Size Range (bp) | GenBank Accession | Primer Sequences (Forward/Reverse) |
|---|---|---|---|---|
| D22S1045 | 22q12.3 | 82-115 | AL022314 (17) | ATTTTCCCCGATGATAGTAGTCT (D22S1045_F; SEQ ID NO: 145) GCGAATGTATGATTGGCAATATTTTT (D22S1045_R; SEQ ID NO: 146) |
| D20S1082 | 20q13.2 | 73-101 | SL158015 | ACATGTATCCCAGAACTTAAAGTAAAC (D20S1082_F; SEQ ID NO: 147) GCAGAAGGGAAAATTGAAGCTG (D20S1082_R; SEQ ID NO: 148) |
| D20S482 | 20p13 | 85-126 | AL121781 (14) | CAGAGACACCGAACCAATAAGA (D20S482_F; SEQ ID NO: 149) GCCACATGAATCAATTCCTATAATAAA (D20S482_R; SEQ ID NO: 150) |
| D18S853 | 18p11.31 | 82-104 | AP005130 (11) | GCACATGTACCCTAAAACTTAAAAT (D18S853_F; SEQ ID NO: 151) GTCAACCAAAACTCAACAAGTAGTAA (D18S853_R; SEQ ID NO: 152) |
| D17S1301 | 17q25.1 | 114-139 | AC016888 (12) | AAGATGAAATTGCCATGTAAAAATA (D17S1301_F; SEQ ID NO: 153) GTGTGTATAACAAAATTCCTATGATGG (D17S1301_R; SEQ ID NO: 154) |
| D17S974 | 17p13.1 | 114-139 | AC034303 (10) | GCACCCAAAACTGAATGTCATA (D17S974_F; SEQ ID NO: 155) GGTGAGAGTGAGACCCTGTC (D17S974_R; SEQ ID NO: 156) |
| D14S1434 | 14q32.13 | 70-98 | AL121612 (13) | TGTAATAACTCTACGACTGTCTGTCTG (D14S1434_F; SEQ ID NO: 157) GAATAGGAGGTGGATGGATGG (D14S1434_R; SEQ ID NO: 158) |
| D12ATA63 | 12q23.3 | 76-106 | AC009771 (13) | GAGCGAGACCCTGTCTCAAG (D12ATA63_F; SEQ ID NO: 159) GGAAAAGACATAGGATAGCAATTT (D12ATA63_R; SEQ ID NO: 160) |
| D11S4463 | 11q25 | 88-116 | AP002806 (14) | TCTGGATTGATCTGTCTGTCC (D11S4463_F; SEQ ID NO: 161) GAATTAAATACCATCTGAGCACTGAA (D11S4463_R; SEQ ID NO: 162) |
| D10S1435 | 10p15.3 | 82-139 | AL354747 (11) | TGTTATAATGCATTGAGTTTTATTCTG (D10S1435_F; SEQ ID NO: 163) GCCTGTCTCAAAAATAAAGAGATAGACA (D10S1435_R; SEQ ID NO: 164) |
| D10S1248 | 10q26.3 | 79-123 | AL391869 (13) | TTAATGAATTGAACAAATGAGTGAG (D10S1248_F; SEQ ID NO: 165) GCAACTCTGGTTGTATTGTCTTCAT (D10S1248_R; SEQ ID NO: 166) |
| D9S2157 | 9q34.2 | 71-107 | AL162417 (10) | CAAAGCGAGACTCTGTCTCAA (D9S2157_F; SEQ ID NO: 167) GAAAATGCTATCCTCTTTGGTATAAAT (D9S2157_R; SEQ ID NO: 168) |
| D9S1122 | 9q21.2 | 93-125 | AL161789 (12) | GGGTATTTCAAGATAACTGTAGATAGG (D9S1122_F; SEQ ID NO: 169) GCTTCTGAAAGCTTCTAGTTTACC (D9S1122_R; SEQ ID NO: 170) |
| D8S1115 | 8p11.21 | 63-96 | AC090739 (9) | TCCACATCCTCACCAACAC (D8S1115_F; SEQ ID NO: 171) GCCTAGGAAGGCTACTGTCAA (D8S1115_R; SEQ ID NO: 172) |

TABLE 15-continued

CODIS and NON-CODIS miniSTRs

| STR Locus (Marker Name) | Chromosome Location | Size Range (bp) | GenBank Accession | Primer Sequences (Forward/Reverse) |
|---|---|---|---|---|
| D6S1017 | 6p21.1 | 81-110 | AL035588 (10) | CCACCCGTCCATTTAGGC (D6S1017_F; SEQ ID NO: 173) GTGAAAAAGTAGATATAATGGTTGGTG (D6S1017_R; SEQ ID NO: 174) |
| D6S474 | 6q21 | 107-136 | AL357514 (17) | GGTTTTCCAAGAGATAGACCAATTA (D6S474_F; SEQ ID NO: 175) GTCCTCTCATAAATCCCACTCATATC (D6S474_R; SEQ ID NO: 176) |
| D5S2500 | 5q11.2 | 85-126 | AC008791 (17) | CTGTTGGTACATAATAGGTAGGTAGGT (D5S2500_F; SEQ ID NO: 177) GTCGTGGGCCCCATAAATC (D5S2500_R; SEQ ID NO: 178) |
| D4S2408 | 4p15.1 | 85-109 | AC110763 (9) | AAGGTACATAACAGTTCAATAGAAAGC (D4S2408_F; SEQ ID NO: 179) GTGAAATGACTGAAAAATAGTAACCA (D4S2408_R; SEQ ID NO: 180) |
| D4S2364 | 4q22.3 | 67-83 | AC022317 (9) | CTAGGAGATCATGTGGGTATGATT (D4S236U_F; SEQ ID NO: 181) GCAGTGAATAAATGAACGAATGGA (D4S2364_R; SEQ ID NO: 182) |
| D3S4529 | 3p12.1 | 111-139 | AC117452 (13) | CCCAAAATTACTTGAGCCAAT (D3S452_F; SEQ ID NO: 183) GAGACAAAATGAAGAAACAGACAG (D3S452_R; SEQ ID NO: 184) |
| D3S3053 | 3q26.31 | 84-108 | AC069259 (9) | TCTTTGCTCTCATGAATAGATCAGT (D3S3053_F; SEQ ID NO: 185) GTTTGTGATAATGAACCCACTCAG (D3S3053_R; SEQ ID NO: 186) |
| D2S1776 | 2q24.3 | 127-161 | AC009475 (11) | TGAACACAGATGTTAAGTGTGTATATG (D2S1776_F; SEQ ID NO: 187) GTCTGAGGTGGACAGTTATGAAA (D2S1776_R; SEQ ID NO: 188) |
| D2S441 | 2p14 | 78-110 | AC079112 (12) | CTGTGGCTCATCTATGAAAACTT (D2S441_F; SEQ ID NO: 189) GAAGTGGCTGTGGTGTTATGAT (D2S441_R; SEQ ID NO: 190) |
| D1S1677 | 1q23.3 | 81-117 | AL513307 (15) | TTCTGTTGGTATAGAGCAGTGTTT (D1S1677_F; SEQ ID NO: 191) GTGACAGGAAGGACGGAATG (D1S1677_R; SEQ ID NO: 192) |
| D1S1627 | 1p21.1 | 81-100 | AC093119 (13) | CATGAGGTTTGCAAATACTATCTTAAC (D1S1627_F; SEQ ID NO: 193) GTTTTAATTTTCTCCAAATCTCCA (D1S1627_R; SEQ ID NO: 194) |
| D1GATA113 | 1p36.23 | 81-105 | Z97987 (11) | TCTTAGCCTAGATAGATACTTGCTTCC (D1GATA113_F; SEQ ID NO: 195) GTCAACCTTTGAGGCTATAGGAA (D1GATA113_R; SEQ ID NO: 196) |

*(Butler et al., J Forensic Sci 5: 1054-1064; Hill et al., Poster #44-17th International Symposium on Human Identification-2006)

Sequencing of the library enriched for polymorphic STR sequences is performed using a NGS technology e.g. sequencing by synthesis. Sequence reads of lengths that encompass the STRs e.g. miniSTRs of at least 100 bp, to a reference STR genome consisting of the polymorphic sequences which were amplified in the sample. Informative STR alleles are identified by differences in the length of the repeats, and the number of STR sequence tags are counted, and used to determine the fetal fraction. Optionally, amplification of the polymorphic STR sequences is performed to enrich a plasma sample, a purified cfDNA sample or a cfDNA sequencing library sample, as described in Examples 5, 6, and 7, respectively.

Example 12

Identification of Fetal STRs by Capillary Electrophoresis: Determination of Fetal Fraction To determine fetal fraction in maternal samples comprising fetal and maternal cfDNA, peripheral blood samples were collected from volunteer pregnant women carrying either male or female fetuses. Peripheral blood samples were obtained and processed to provide purified cfDNA.2.

Ten microliters of cfDNA samples were analyzed using the AmpFlSTR® MiniFiler™ PCR amplification kit (Applied Biosystems, Foster City, Calif.) according to the manufacturer's instructions. Briefly, cfDNA contained in 10 ml was amplified in a reaction volume of 25 µl containing 5 µL fluorescently labeled primers (AmpF/STR® MiniFiler™ Primer Set), and the AmpF/STR® MiniFiler™ Master Mix, which includes AmpliTaq Gold® DNA polymerase and associated buffer, salt (1.5 mM MgC12), and 200 µM deoxynucleotide triphosphates (dNTPs: dATP, dCTP, dGTP and dTTP). The fluorescently labeled primers are forward primers that are labeled with 6FAM™, VIC™, NED™, and PET™ dyes. Thermal cycling was performed with the Gene Amp9700 (Applied Biosystems) using the following cycling conditions: incubating at 95° C. for 10 minutes, followed by 30 cycles at 94° C. for 20 seconds, 59° C. for 2 minute, and 72° C. for 1 minute, which was followed by a final incubation at 60° C. for 45 minutes. A final hold at 4° C. was added until the samples were removed for analysis. The amplified product was prepared by diluting 1 ul of amplified product in 8.7 ul Hi-DiTM formamide (Applied Biosystems) and 0.3 µl GeneScanTM-500 LIZ_internal size standard (Applied Biosystems), and analyzed with an ABI PRISM3130x1 Genetic Analyzer (Applied Biosystems) using Data Collection HID_G5_POP4 (Applied Biosystems), and a 36-cm capillary array. All genotyping was performed with GeneMapper_ID v3.2 software (Applied Biosystems) using manufacturer provided allelic ladders and bins and panels.

All genotyping measurement were performed on the Applied Biosystems 3130xl Genetic Analyzer, using a ±0.5-nt "window" around the size obtained for each allele to allow for detection and correct assignment of alleles. Any sample allele whose size was outside the ±0.5-nt window was determined to be OL i.e. "Off Ladder". OL alleles are alleles of a size that is not represented in the AmpFlSTR® MiniFiler™ Allelic Ladder or an allele that does not correspond to an allelic ladder, but whose size is just outside a window because of measurement error. The minimum peak height threshold of >50 RFU was set based on validation experiments performed to avoid typing when stochastic effects are likely to interfere with accurate interpretation of mixtures. The calculation of fetal fraction is based on averaging all informative markers. Informative markers are identified by the presence of peaks on the electropherogram that fall within the parameters of preset bins for the STRs that are analyzed.

Calculations of fetal fraction were performed using the average peak height for major and minor alleles at every STR locus determined from triplicate injections. The rules applied to the calculation are:

1. off-ladder allele (OL) data for alleles are not included in the calculation; and
2. only peak heights derived from >50 RFU (relative fluorescence units) are included in the calculation
3. if only one bin is present the marker is deemed non-informative; and
4. if a second bin is called but the peaks of the first and second bins are within 50-70% of their relative fluorescence units (RFU) in peak height, the minority fraction is not measured and the marker is deemed not informative.

The fraction of the minor allele for any given informative marker is calculated by dividing the peak height of the minor component by the sum of the peak height for the major component, and expressed as a percent was first calculated for each informative locus as fetal fraction=(Σpeak height of minor allele/Σ peak height of major allele(s))×100, The fetal fraction for a sample comprising two or more informative STRs, would be calculated as the average of the fetal fractions calculated for the two or more informative markers.

Table 16 provides the data obtained from analyzing cfDNA of a subject pregnant with a male fetus.

TABLE 16

Detection of Fetal STR Alleles and Use for Determination of Fetal Fraction

| STR | Allele 1 | Allele 2 | Allele 3 | Allele 1 Height | Allele 2 Height | Allele 3 Height | Fetal Fraction | Fetal Fraction (Mean/STR) |
|---|---|---|---|---|---|---|---|---|
| AMEL | X | Y | | 3599 | 106 | | 2.9 | |
| AMEL | X | Y | | 3602 | 110 | | 3.1 | |
| AMEL | X | Y | | 3652 | 109 | | 3.0 | 3.0 |
| CSF1PO | 11 | 12 | | 2870 | 2730 | | | |
| CSF1PO | 11 | 12 | | 2924 | 2762 | | | |
| CSF1PO | 11 | 12 | | 2953 | 2786 | | | |
| D13S317 | 11 | 12 | | 2621 | 2588 | | | |
| D13S317 | 11 | 12 | | 2680 | 2619 | | | |
| D13S317 | 11 | 12 | | 2717 | 2659 | | | |
| D16S539 | 9 | 11 | | 1056 | 1416 | | | |
| D16S539 | 9 | 11 | | 1038 | 1394 | | | |
| D16S539 | 9 | 11 | | 1072 | 1437 | | | |
| D18S51 | 13 | 15 | | 2026 | 1555 | | | |
| D18S51 | 13 | 15 | | 2006 | 1557 | | | |
| D18S51 | 13 | 15 | | 2050 | 1578 | | | |
| D21S11 | 28 | 31.2 | | 2450 | 61 | | 2.5 | |
| D21S11 | 28 | 31.2 | | 2472 | 62 | | 2.5 | |
| D21S11 | 28 | 31.2 | | 2508 | 67 | | 2.7 | 2.6 |
| D2S1338 | 20 | 23 | | 3417 | 3017 | | | |
| D2S1338 | 20 | 23 | | 3407 | 3020 | | | |
| D2S1338 | 20 | 23 | | 3493 | 3055 | | | |
| D7S820 | 9 | 12 | 13 | 2373 | 178 | 1123 | 5.1 | |
| D7S820 | 9 | 12 | 13 | 2411 | 181 | 1140 | 5.1 | |

TABLE 16-continued

Detection of Fetal STR Alleles and Use for Determination of Fetal Fraction

| STR | Allele 1 | Allele 2 | Allele 3 | Allele 1 Height | Allele 2 Height | Allele 3 Height | Fetal Fraction | Fetal Fraction (Mean/STR) |
|---|---|---|---|---|---|---|---|---|
| D7S820 | 9 | 12 | 13 | 2441 | 182 | 1156 | 5.1 | 5.1 |
| FGA | 17.2 | 22 | 25 | 68 | 1140 | 896 | 3.3 | |
| FGA | 17.2 | 22 | 25 | 68 | 1144 | 909 | 3.1 | |
| FGA | 17.2 | 22 | 25 | 68 | 1151 | 925 | 3.3 | 3.2 |

Fetal Fraction = 3.5

The results show that STRs can be identified in maternal cfDNA and can be used for determining the presence or absence of fetal DNA as indicated by the detection of a minor component at one or more STR alleles, for determining the percent fetal fraction, and for determining fetal gender as indicated by the presence or absence of the Amelogenin allele.

Example 13

Whole Genome Amplification of cfDNA and Detection of Fetal STRs by Capillary Electrophoresis To improve the sensitivity of the STR capillary electrophoresis assay in detecting and quantifying the STR alleles in the minor contributor of the cfDNA sample, the number of starting genomes in the artificial samples was increased by a modified whole genome amplification strategy.

Peripheral blood samples were collected and processed as described in Example 2. Cell-free DNA was extracted from 1 ml cell-free plasma using the Roche MagNA Pure Compact Nucleic Acid Isolation Kit I—Large Volume (Roche Applied Science, IN) using the MagNA Pure Compact Instrument, and eluted in 50 µl of elution buffer. Ten microliters of the extracted cfDNA were used to quantify the cfDNA, and the remainder was stored (see storage instructions WI0035 Clinical Sample Storage). The concentration of the plasma extracted cfDNA was determined by fluorescence-based quantitation with UV absorbance measurements using the Qubit™ Quantitation Platform (Invitrogen).

The concentration of cfDNA quantified in plasma samples prepared using the MagnaPure Nucleic Acid Isolation Kit I from 16 pregnant subjects was determined to range between 20 and 100 pg/µl. As the fetal component of plasma cfDNA is known to contribute 3-10% of the total plasma cfDNA, artificial plasma samples were created by spiking aliquots of cfDNA derived from plasma of female volunteer subjects with cfDNA extracted from plasma of male volunteer subjects to mimic the ratios of fetal to maternal cfDNA found in the pregnant subjects. Artificial samples were created to contain 200-1000 pg of extracted female cfDNA that was spiked with 45-150 pg of extracted male cfDNA in a total volume of 10 µl. Each artificial sample was spiked to contain 3%, 5% and 10% male cfDNA.

Artificial samples having concentrations of total cfDNA of less than approximately 50 pg/µl, were pre-amplified using the modified improved primer extension amplification PCR (mIPEP) amplification according to the method of Hanson and Ballantyne, (Hanson and Ballantyne, Analytical Biochem 346:246-257 [2005]) as follows. Ten microliters of spiked plasma cfDNA were amplified in a 25 µl reaction volume containing 1 mM dNTPs, 2.5 mM $MgCl_2$ (Applied Biosystems), 1× Expand High Fidelity Buffer (No. 3), 10.5U Expand High Fidelity Enzyme Mix (Roche Diagnostics), and 40 µM PEP primer (5'-NNNNNNNNNNNNNNNN-3', Qiagen). The amplification was performed in a GeneAmp PCR System 9700 Thermocycler under the following conditions: (1) 20 and 30 cycles of 94° C. for 1 minute, 37° C. for 2 minutes, and 0.1° C./s ramp to 55° C. for 4 minutes. The amplification product was purified using a Qiagen column. The concentration of the amplification product was determined using the Qubit™ Quantitation Platform as described above. STR analysis was performed as described in Example 9 above, except that only peak heights >100 RFU were included in the calculations.

The results are shown in Tables 17, 18, and 19. The results provided in Table 17 show that the cfDNA contained in 10 µl cfDNA of artificial samples ART23 and ART24 having a starting concentration of cfDNA of 46.2 and 50.2 pg/µl, respectively, was amplified by approximately 5 and 10 fold following 20 and 30 cycles of PCR amplification, respectively.

These data indicate that a pre-amplification of cfDNA using the mIPEP method provided enhanced levels of total cfDNA rendering the level of the minor component more amenable to the STR analysis.

TABLE 17

Whole Genome Amplification of cfDNA by mIPEP

| SAMPLE | cfDNA without mIEP (pg/µl) | cfDNA with mIPEP:20 PCR cycles (pg/50 µl) | cfDNA with mIPEP:30 PCR cycles (pg/50 µl) |
|---|---|---|---|
| ART23 | 46.2 | 2265 | 4125 |
| ART24 | 50.2 | 2085 | 3875 |

Table 18 shows triplicate measurements profiling 9 loci of the cfDNA of spiked samples ART23 and ART24 following the mIPEP procedure with 20 and 30 cycles of amplification, as described above.

The data in Table 19 indicate that pre-amplification of cfDNA enables the detection and quantification of the minor component at most loci tested in artificially mixed samples having a starting cfDNA concentration that would otherwise not permit an accurate analysis of the minor STR alleles.

TABLE 18 mIPEP Preamplification and Detection of Minor Fetal Component

| STR Locus | Allele | ART23 (453 pg) mIPEP amplified 20 cycles Allele Height | ART23 (825 pg) mIPEP amplified 20 cycles Allele Height | ART23 (462 pg) Extracted unamplified cfDNA Allele Height | Allele | ART24 (417 pg) mIPEP amplified 30 cycles Allele Height | ART24 (775 pg) mIPEP amplified 30 cycles Allele Height | ART24 (502 pg) Extracted unamplified cfDNA Allele Height |
|---|---|---|---|---|---|---|---|---|
| AMEL | X/Y | 291/95 | 397/170 | 535/832 | X/Y | 695/359 | 1878/1148 | 1564/1959 |
| AMEL | X/Y | 425/147 | 428/188 | 675/1048 | X/Y | 1216/619 | 1551/954 | 1573/1943 |
| AMEL | X/Y | 267/94 | 455/203 | 664/1043 | X/Y | 718/363 | 1479/924 | 1621/2024 |
| CSF1PO | 10/11 | 800/979 | 725/1009 | 1429/1325 | 11/12 | 2029/1317 | 4159/2317 | 2990/3083 |
| CSF1PO | 10/11 | 1147/1432 | 789/1102 | 1779/1650 | 11/12 | 3449/2223 | 3460/113/1890 | 2996/3118 |
| CSF1PO | 10/11 | 729/906 | 831/1162 | 1783/1657 | 11/12 | 2006/1309 | 3362/1840 | 3072/3183 |
| D13S317 | 12 | 743 | 515 | 1229 | 11 | 955 | 1490 | 3634 |
| D13S317 | 12 | 1079 | 563 | 1534 | 11 | 1631 | 1198 | 3631 |
| D13S317 | 12 | 668 | 583 | 1520 | 11 | 968 | 1170 | 3795 |
| D16S539 | 9/10 | 239/140 | 370/466 | 835/676 | 10/11 | 513/512 | 1173/1472 | 1678/973 |
| D16S539 | 9/10 | 347/203 | 64*(OL)/391/489 | 1046/864 | 10/11 | 859/870 | 973/1212 | 1730/999 |
| D16S539 | 9/10 | 227/134 | 441/515 | 1055/860 | 10/11 | 530/513 | 960/1183 | 1784/1044 |
| D18S51 | 14/15 | 359/464 | 363/220 | 785/541 | 12/18 | 1044/576 | 1840/786 | 2559/1507 |
|  |  | 512/645 | 391/226 | 999/672 | 12/18 | 1769/994 | 1511/643 | 2565/1469 |
|  |  | 313/402 | 409/245 | 994/685 | 12/18 | 1033/567 | 1496/631 | 2643/1523 |
| D21S11 | 29/32 | 103/104 | 114/173 | 605/413 | 31.2 | 381 | 661 | 3276 |
|  |  | 149/153 | 130/182 | 759/523 | 31.2 | 650 | 536 | 3028 |
|  |  | 85/86 | 131/196 | 760/525 | 31.2 | 380 | 520 | 3282 |
| D2S1338 | 18/20 | 572/383 | 428/363 | 1116/1013 | 19/20 | 1066/433 | 2315/1243 | 2962/2968 |
|  |  | 827/553 | 454/386 | 1428/1279 | 19/20 | 1821/757 | 1901/101 | 2942/2942 |
|  |  | 530/351 | 482/408 | 1431/1275 | 19/20 | 1063/444 | 1859/1012 | 3072/3067 |
| D7S820 | 11/12 | 262/167 | 149/270 | 557/627 | 11/12 | 256/138 | 520/322 | 1550/1548 |
|  |  | 62/366/231 | 162/292 | 699/775 | 11/12 | 448/236 | 419/258 | 1484/1466 |
|  |  | 224/146 | 169/307 | 689/779 | 11/12 | 253/141 | 406/250 | 1579/1573 |
| FGA | 21/23 | 263/146 | 181/88 | 596/365 | 22/24 | 228/244 | 375/429 | 1272/1064 |
|  |  | 384/215 | 191/92 | 762/450 | 22/24 | 409/425 | 303/345 | 1221/1023 |
|  |  | 230/136 | 202/102 | 749/456 | 22/24 | 232/250 | 297/348 | 1298/1087 |

*"OL" means "Off Ladder measurement"

TABLE 19

Identification of fetal STRs following mIPEP amplification of cfDNA in a maternal sample

| STR marker | Allele 1/ Height | Allele 2/ Height | Allele 3/ Height | Allele 4/ Height | Percent minor fraction/STR - minor >100 RFU | Percent minor fraction/STR - minor <100 RFU |
|---|---|---|---|---|---|---|
| Amelogenin | X/2799 | Y/207 |  |  |  |  |
| Amelogenin | X/2751 | Y/198 |  |  |  |  |
| Amelogenin | X/3109 | Y/232 |  |  |  |  |
|  | X/2886 | Y/212 |  |  |  | 7 |
| CSF1PO | 10/2377 | 11/1869 | 12/508 |  |  |  |
| CSF1PO | 10/2299 | 11/1814 | 12/498 |  |  |  |
| CSF1PO | 10/2616 | 11/206 | 12/562 |  |  |  |
|  | 10/2431 | 11/1917 | 12/523 |  | 12 |  |
| D13S317 | 10/1232 | 11/1600 | 13/186 |  |  |  |
| D13S317 | 10/1208 | 11/1548 | 13/182 |  |  |  |
| D13S317 | 10/1386 | 11/1758 | 13/212 |  |  |  |
|  | 10/1275 | 11/1635 | 13/193 |  | 12 |  |
| D16S539 | 11/757 | 12/933 |  |  |  |  |
| D16S539 | 11/729 | 12/885 |  |  |  |  |
| D16S539 | 11/836 | 12/1031 |  |  |  |  |
|  | 11/774 | 12/950 |  |  | 12 |  |
| D18S51 | OL/80 | 14/3137 | 15/371 |  |  |  |
| D18S51 | 11/73 | 14/3082 | 15/362 |  |  |  |
| D18S51 | OL/83 | 14/3488 | 15/413 |  |  |  |
|  | OL | 14/3236 | 15/382 |  |  |  |
| D21S11 | 29/953 | 30/941 |  |  |  |  |
| D21S11 | 29/921 | 30/908 |  |  |  |  |
| D21S11 | 29/1046 | 30/1045 |  |  |  |  |
|  | 29/973 | 30/965 |  |  |  |  |
| D2S1338 | 17/461 | 18/366 | 20/2280 | 24/1760 |  |  |
| D2S1338 | 17/460 | 18/360 | 20/2240 | 24/1712 |  |  |
| D2S1338 | 17/508 | 18/409 | 20/2563 | 24/1971 |  |  |
|  | 17/476 | 18/378 | 20/2361 | 24/1814 | 20 |  |
| D7S820 | 8/1409 | 9/60 | 12/1059 |  |  |  |
| D7S820 | 8/1380 | 9/60 | 12/1036 |  |  |  |

TABLE 19-continued

Identification of fetal STRs following mIPEP amplification of cfDNA in a maternal sample

| STR marker | Allele 1/ Height | Allele 2/ Height | Allele 3/ Height | Allele 4/ Height | Percent minor fraction/STR - minor >100 RFU | Percent minor fraction/STR - minor <100 RFU |
|---|---|---|---|---|---|---|
| D7S820 | 8/1561 | 9/69 | 12/1166 | | | |
|  | 8/1450 | 9/63 | 12/1087 | | | 2 |
| FGA | 19/825 | 21/850 | 25/279 | | | |
| FGA | 19/807 | 21/841 | 25/265 | | | |
| FGA | 19/913 | 21/958 | 25/306 | | | |
|  | 19/848 | 21/883 | 25/283 | | 16 | |
| % fetal fraction >100 RFU for minor allele →12 | | | | | 12 | |
| % fetal fraction including <100 RFU for minor allele →11 | | | | | | 11 |

Example 14

Identification of a Partial Chromosomal Deletion

The use of sequence doses was applied for assessing partial chromosomal deletion in a biological test sample of cfDNA that was prepared from blood plasma, and sequenced as described in Example 4. The sample was confirmed by karyotyping to have been derived from a subject with a partial deletion of chromosome 11.

Figure 6:
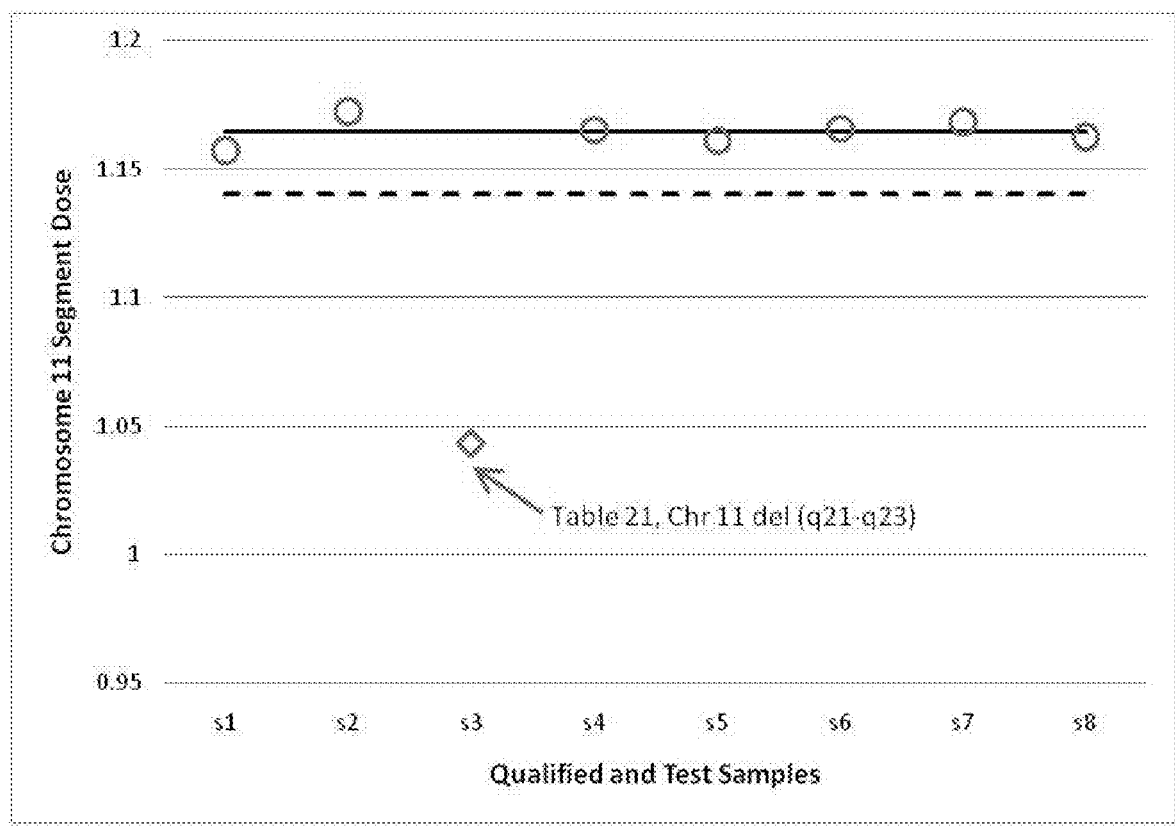
FIG. 6 shows sequence doses (Y-axis) for a segment of human chromosome 11 (81000082-103000103 bp) determined from sequencing cfDNA extracted from a set of 7 qualified samples (O) obtained and 1 test sample (♦) from pregnant human subjects. A sample from a subject carrying a fetus with a partial aneuploidy of chromosome 11 (♦) was identified.

Analysis of the sequencing data for the partial aneuploidy (partial deletion of chromosome 11 i.e. q21-q23) was performed as described for the chromosomal aneuploidies in the previous examples. Mapping of the sequence tags to chromosome 11 in a test sample revealed a noticeable loss of tag counts between base pairs 81000082-103000103 in the q arm of the chromosome relative to the tag counts obtained for corresponding sequence on chromosome 11 in the qualified samples (data not shown). Sequence tags mapped to the sequence of interest on chromosome 11 (810000082-103000103 bp) in each of the qualified samples, and sequence tags mapped to all 20 megabase segments in the entire genome in the qualified samples i.e. qualified sequence tag densities, were used to determine qualified sequence doses as ratios of tag densities in all qualified samples. The average sequence dose, standard deviation, and coefficient of variation were calculated for all 20 megabase segments in the entire genome, and the 20-megabase sequence having the least variability was the identified normalizing sequence on chromosome 5 (13000014-33000033 bp) (See Table 8), which was used to calculate the dose for the sequence of interest in the test sample (see Table 9). Table 20 provides the sequence dose for the sequence of interest on chromosome 11 (810000082-103000103 bp) in the test sample that was calculated as the ratio of sequence tags mapped to the sequence of interest and the sequence tags mapped to the identified normalizing sequence. FIG. 6 shows the sequence doses for the sequence of interest in the 7 qualified samples (0) and the sequence dose for the corresponding sequence in the test sample (0). The mean is shown by the solid line, and the calculated threshold for the positive diagnosis of partial aneuploidy that was set 5 standard deviations from the mean is shown by the dashed line. A diagnosis for partial aneuploidy was based on the sequence dose in the test sample being less than the set threshold. The test sample was verified by karyotyping to have deletion q21-q23 on chromosome 11.

Therefore, massively parallel sequencing of samples comprising a mixture of cfDNA from two genomes can identify polymorphisms including chromosomal deletions.

TABLE 20

Qualified Normalizing Sequence, Dose and Variance for Sequence Chr11: 81000082-103000103 (qualified samples n = 7)

| | Chr11: 81000082-103000103 | | |
|---|---|---|---|
| | Avg | Stdev | CV |
| Chr5: 13000014-33000033 | 1.164702 | 0.004914 | 0.42 |

TABLE 21

Sequence Dose for Sequence of Interest (81000082-103000103) on Chromosome 11 (test sample 11206)

| Chromosome Segment | Sequence Tag Density | Chromosome Segment Dose for Chr 11 (q21-q23) | Threshold |
|---|---|---|---|
| Chr11: 81000082-103000103 | 27,052 | 1.0434313 | 1.1401347 |
| Chr5: 13000014-33000033 | 25,926 | | |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for identifying multiple fetal polymorphisms in a fetal genome of a blood sample obtained from a pregnant woman comprising a mixture of cfDNA of a fetal and a maternal genome, said method comprising steps:
    (a) performing whole genome sequencing on at least a portion of said mixture of cfDNA, thereby obtaining a plurality of sequence tags, wherein said mixture is unenriched for said multiple polymorphisms, and wherein said sequencing is massively parallel sequencing of clonally amplified cfDNA molecules or of single cfDNA molecules;
    (b) mapping the sequences of said plurality of sequence tags to the sequences of multiple reference polymorphisms, to identify sequence tags mapped to each of said multiple reference polymorphisms;
    (c) for each of said multiple reference polymorphisms;
      (i) quantifying mapped sequence tags that map to a first allele of the reference polymorphism to obtain a quantitative value for the first allele;
      (ii) quantifying mapped sequence tags that map to the second allele of the reference polymorphism to obtain a quantitative value for the second allele;
      (iii) determining a parameter from the quantitative value for the first allele and the quantitative value for the second allele;
      (iv) comparing the parameter to one or more cutoff values associated with the relative abundance of fetal cfDNA in the material sample; and
      (v) classifying each allele as a (i) minor allele or (ii) major allele, based on the comparison of the parameter to the one or more cutoff values:
    whereby a minor allele is identified as a fetal polymorphism in the maternal sample:
    wherein the identification of fetal polymorphisms originating from the fetal genome in the mixture is performed without genotyping the maternal alleles in a maternal sample that is substantially free of fetal nucleic acids.

2. The method of claim 1, wherein said multiple fetal polymorphisms in said fetal genome are associated with at least one disorder.

3. The method of claim 1, wherein each of said multiple fetal polymorphisms comprise at least one single nucleotide polymorphism (SNP), a tandem SNP, or a short tandem repeat (STR).

4. The method of claim 3, wherein said at least one SNP is a tag SNP.

5. The method of claim 3, wherein said at least one STR is a tag STR.

6. The method of claim 1, wherein said sequencing is massively parallel sequencing of clonally amplified cfDNA molecules.

7. The method of claim 1, wherein said sequencing is performed using massively parallel sequencing-by-synthesis with reversible dye terminators.

8. The method of claim 1, wherein said sequencing is performed using massively parallel sequencing-by-ligation.

9. The method of claim 1, wherein said sample is a plasma sample.

10. A method of identifying fetal alleles in a maternal sample, comprising:
    (a) performing massively parallel whose genome sequencing on a mixture of fetal and maternal cfDNA from a maternal sample, and providing digital sequence information comprising sequence reads obtained from the massively parallel whole genome sequencing,
       wherein the digital sequence information comprises a plurality of polymorphic sequence reads; and
       wherein said multiple polymorphic sequence are not specifically enriched in said mixture;
    (b) mapping a plurality of the sequence reads to polymorphic sites in a reference genome to obtain a plurality of mapped sequence tags;
    (c) for each of a plurality of polymorphic sites in the reference genome:
       (i) quantifying mapped sequence tags that map to a first allele of the polymorphic site to obtain a quantitative value for the first allele;
       (ii) quantifying mapped sequence tags that map to the second allele of the polymorphic site to obtain a quantitative value for the second allele;
       (iii) determining a parameter from the quantitative value for the first allele and the quantitative value for the second allele;
       (iv) comparing the parameter to one or more cutoff values associated with the relative abundance of fetal cfDNA in the maternal sample; and
       (v) classifying each allele at the polymorphic site as a (i) minor allele or (ii) major allele, based on the comparison of the parameter to the one or more cutoff values;
    whereby a minor allele is identified as a fetal allele in the maternal sample;
    wherein the identification of fetal alleles is performed without genotyping the maternal alleles in a maternal sample that is substantially free of fetal nucleic acids.

* * * * *

UNITED STATES PATENT AND TRADEMARK OFFICE
CERTIFICATE OF CORRECTION

PATENT NO. : 10,662,474 B2
APPLICATION NO. : 13/009718
DATED : May 26, 2020
INVENTOR(S) : Richard P. Rava Page 1 of 1

It is certified that error appears in the above-identified patent and that said Letters Patent is hereby corrected as shown below:

On the Title Page

Column 2, item (74), (Attorney, Agent or Firm), Line 1, delete "Inc;" and insert -- Inc.; --, therefor.

In the Claims

Column 197, Line 26, in Claim 1, delete "polymorphisms;" and insert -- polymorphisms: --, therefor.
Column 197, Line 38, in Claim 1, delete "material" and insert -- maternal --, therefor.
Column 197, Line 41, in Claim 1, delete "values:" and insert -- values; --, therefor.
Column 197, Line 43, in Claim 1, delete "sample:" and insert -- sample; --, therefor.
Column 198, Line 23, in Claim 10, delete "whose" and insert -- whole --, therefor.
Column 198, Line 30, in Claim 10, delete "sequence" and insert -- sequences --, therefor.

Signed and Sealed this
Fifteenth Day of September, 2020

Andrei Iancu
*Director of the United States Patent and Trademark Office*

SEQUENCE LISTING

<160> NUMBER OF SEQ ID NOS: 317

<210> SEQ ID NO 1
<211> LENGTH: 111

<212> TYPE: DNA
<213> ORGANISM: Homo sapiens

<400> SEQUENCE: 1
cacatgcaca gccagcaacc ctgtcagcag gagttcccac cagtttcttt ctgagaacat    60
ctgttcaggt ttctctccat ctctatttac tcaggtcaca ggaccttggg g            111

<210> SEQ ID NO 2
<211> LENGTH: 111
<212> TYPE: DNA
<213> ORGANISM: Homo sapiens

<400> SEQUENCE: 2
cacatgcaca gccagcaacc ctgtcagcag gagttcccac cagtttcttt ctgagaacat    60
ctgttcaggt ttctctccat ctctgtttac tcaggtcaca ggaccttggg g            111

<210> SEQ ID NO 3
<211> LENGTH: 126
<212> TYPE: DNA
<213> ORGANISM: Homo sapiens

<400> SEQUENCE: 3
tgaggaagtg aggctcagag ggtaagaaac tttgtcacag agctggtggt gagggtggag    60
attttacact ccctgcctcc cacaccagtt tctccagagt ggaaagactt tcatctcgca   120
ctggca                                                             126

<210> SEQ ID NO 4
<211> LENGTH: 126
<212> TYPE: DNA
<213> ORGANISM: Homo sapiens

<400> SEQUENCE: 4
tgaggaagtg aggctcagag ggtaagaaac tttgtcacag agctggtggt gagggtggag    60
attttacact ccctgcctcc cacaccagtt tctccggagt ggaaagactt tcatctcgca   120
ctggca                                                             126

<210> SEQ ID NO 5
<211> LENGTH: 121
<212> TYPE: DNA
<213> ORGANISM: Homo sapiens

<400> SEQUENCE: 5
gtgccttcag aacctttgag atctgattct attttttaaag cttcttagaa gagagattgc    60
aaagtgggtt gtttctctag ccagacaggg caggcaaata ggggtggctg gtgggatggg   120
a                                                                   121

<210> SEQ ID NO 6
<211> LENGTH: 121
<212> TYPE: DNA
<213> ORGANISM: Homo sapiens

<400> SEQUENCE: 6
gtgccttcag aacctttgag atctgattct attttttaaag cttcttagaa gagagattgc    60
aaagtgggtt gtttctctag ccagacaggg caggtaaata ggggtggctg gtgggatggg   120
a                                                                   121

<210> SEQ ID NO 7

```
<211> LENGTH: 111
<212> TYPE: DNA
<213> ORGANISM: Homo sapiens

<400> SEQUENCE: 7
aggtgtgtct ctcttttgtg aggggagggg tcccttctgg cctagtagag ggcctggcct      60
gcagtgagca ttcaaatcct caaggaacag ggtggggagg tgggacaaag g              111

<210> SEQ ID NO 8
<211> LENGTH: 111
<212> TYPE: DNA
<213> ORGANISM: Homo sapiens

<400> SEQUENCE: 8
aggtgtgtct ctcttttgtg aggggagggg tcccttctgg cctagtagag ggcctggcct      60
gcagtgagca ttcaaatcct cgaggaacag ggtggggagg tgggacaaag g              111

<210> SEQ ID NO 9
<211> LENGTH: 139
<212> TYPE: DNA
<213> ORGANISM: Homo sapiens

<400> SEQUENCE: 9
cctcgcctac tgtgctgttt ctaaccatca tgcttttccc tgaatctctt gagtcttttt      60
ctgctgtgga ctgaaacttg atcctgagat tcacctctag tccctctgag cagcctcctg     120
gaatactcag ctgggatgg                                                  139

<210> SEQ ID NO 10
<211> LENGTH: 139
<212> TYPE: DNA
<213> ORGANISM: Homo sapiens

<400> SEQUENCE: 10
cctcgcctac tgtgctgttt ctaaccatca tgcttttccc tgaatctctt gagtcttttt      60
ctgctgtgga ctgaaacttg atcctgagat tcacctctag tccctctggg cagcctcctg     120
gaatactcag ctgggatgg                                                  139

<210> SEQ ID NO 11
<211> LENGTH: 117
<212> TYPE: DNA
<213> ORGANISM: Homo sapiens

<400> SEQUENCE: 11
aattgcaatg gtgagaggtt gatggtaaaa tcaaacggaa cttgttattt tgtcattctg      60
atggactgga actgaggatt ttcaatttcc tctccaaccc aagacacttc tcactgg        117

<210> SEQ ID NO 12
<211> LENGTH: 117
<212> TYPE: DNA
<213> ORGANISM: Homo sapiens

<400> SEQUENCE: 12
aattgcaatg gtgagaggtt gatggtaaaa tcaaacggaa cttgttattt tgtcattctg      60
atggactgga actgaggatt ttcaatttcc tttccaaccc aagacacttc tcactgg        117

<210> SEQ ID NO 13
<211> LENGTH: 114
<212> TYPE: DNA
<213> ORGANISM: Homo sapiens
```

<400> SEQUENCE: 13
gaaatgcctt ctcaggtaat ggaaggttat ccaaatattt ttcgtaagta tttcaaatag    60
caatggctcg tctatggtta gtctcacagc cacattctca gaactgctca aacc         114

<210> SEQ ID NO 14
<211> LENGTH: 114
<212> TYPE: DNA
<213> ORGANISM: Homo sapiens

<400> SEQUENCE: 14
gaaatgcctt ctcaggtaat ggaaggttat ccaaatattt ttcgtaagta tttcaaatag    60
caatggctcg tctatggtta gtctcgcagc cacattctca gaactgctca aacc         114

<210> SEQ ID NO 15
<211> LENGTH: 128
<212> TYPE: DNA
<213> ORGANISM: Homo sapiens

<400> SEQUENCE: 15
acccaaaaca ctggaggggc ctcttctcat tttcggtaga ctgcaagtgt tagccgtcgg    60
gaccagcttc tgtctggaag ttcgtcaaat tgcagttaag tccaagtatg ccacatagca   120
gataaggg                                                            128

<210> SEQ ID NO 16
<211> LENGTH: 128
<212> TYPE: DNA
<213> ORGANISM: Homo sapiens

<400> SEQUENCE: 16
acccaaaaca ctggaggggc ctcttctcat tttcggtaga ctgcaagtgt tagccgtcgg    60
gaccagcttc tgtctggaag ttcgtcaaat tgcagttagg tccaagtatg ccacatagca   120
gataaggg                                                            128

<210> SEQ ID NO 17
<211> LENGTH: 110
<212> TYPE: DNA
<213> ORGANISM: Homo sapiens

<400> SEQUENCE: 17
gcaccagaat ttaaacaacg ctgacaataa atatgcagtc gatgatgact tcccagagct    60
ccagaagcaa ctccagcaca cagagaggcg ctgatgtgcc tgtcaggtgc              110

<210> SEQ ID NO 18
<211> LENGTH: 110
<212> TYPE: DNA
<213> ORGANISM: Homo sapiens

<400> SEQUENCE: 18
gcaccagaat ttaaacaacg ctgacaataa atatgcagtc gatgatgact tcccagagct    60
ccagaagcaa ctccagcaca cggagaggcg ctgatgtgcc tgtcaggtgc              110

<210> SEQ ID NO 19
<211> LENGTH: 116
<212> TYPE: DNA
<213> ORGANISM: Homo sapiens

<400> SEQUENCE: 19

```
tgactgtata ccccaggtgc acccttgggt catctctatc atagaactta tctcacagag    60
tataagagct gatttctgtg tctgcctctc acactagact tccacatcct tagtgc       116
```

<210> SEQ ID NO 20
<211> LENGTH: 116
<212> TYPE: DNA
<213> ORGANISM: Homo sapiens

<400> SEQUENCE: 20

```
tgactgtata ccccaggtgc acccttgggt catctctatc atagaactta tctcacagag    60
tataagagct gatttctgtg tctgcctgtc acactagact tccacatcct tagtgc       116
```

<210> SEQ ID NO 21
<211> LENGTH: 110
<212> TYPE: DNA
<213> ORGANISM: Homo sapiens

<400> SEQUENCE: 21

```
tgtacgtggt caccagggga cgcctggcgc tgcgagggag gccccgagcc tcgtgccccc    60
gtgaagcttc agctcccctc cccggctgtc cttgaggctc ttctcacact              110
```

<210> SEQ ID NO 22
<211> LENGTH: 110
<212> TYPE: DNA
<213> ORGANISM: Homo sapiens

<400> SEQUENCE: 22

```
tgtacgtggt caccagggga cgcctggcgc tgcgagggag gccccgagcc tcgtgccccc    60
gtgaagcttc agctcccctc cctggctgtc cttgaggctc ttctcacact              110
```

<210> SEQ ID NO 23
<211> LENGTH: 114
<212> TYPE: DNA
<213> ORGANISM: Homo sapiens

<400> SEQUENCE: 23

```
cagtggaccc tgctgcacct ttcctcccct cccatcaacc tcttttgtgc ctcccctcc     60 gtgtaccacc ttctctgtca ccaaccctgg cctcacaact ctctcctttg ccac         114
```

<210> SEQ ID NO 24
<211> LENGTH: 114
<212> TYPE: DNA
<213> ORGANISM: Homo sapiens

<400> SEQUENCE: 24

```
cagtggaccc tgctgcacct ttcctcccct cccatcaacc tcttttgtgc ctcccctcc     60 gtgtaccacc ttctctgtca ccaccctgg cctcacaact ctctcctttg ccac          114
```

<210> SEQ ID NO 25
<211> LENGTH: 110
<212> TYPE: DNA
<213> ORGANISM: Homo sapiens

<400> SEQUENCE: 25

```
cagtggcata gtagtccagg ggctcctcct cagcacctcc agcaccttcc aggaggcagc    60
agcgcaggca gagaacccgc tggaagaatc ggcggaagtt gtcggagagg              110
```

<210> SEQ ID NO 26
<211> LENGTH: 110

```
<212> TYPE: DNA
<213> ORGANISM: Homo sapiens

<400> SEQUENCE: 26
cagtggcata gtagtccagg ggctcctcct cagcacctcc agcaccttcc aggaggcagc      60
agcgcaggca gagaacccgc tggaaggatc ggcggaagtt gtcggagagg                110

<210> SEQ ID NO 27
<211> LENGTH: 129
<212> TYPE: DNA
<213> ORGANISM: Homo sapiens

<400> SEQUENCE: 27
aggtctgggg gccgctgaat gccaagctgg gaatcttaaa tgttaaggaa caaggtcata      60
caatgaatgg tgtgatgtaa aagcttggga ggtgatttct gagggtaggt gctgggttta     120
atgggagga                                                             129

<210> SEQ ID NO 28
<211> LENGTH: 129
<212> TYPE: DNA
<213> ORGANISM: Homo sapiens

<400> SEQUENCE: 28
aggtctgggg gccgctgaat gccaagctgg gaatcttaaa tgttaaggaa caaggtcata      60
caatgaatgg tgtgatgtaa aagcttggga ggtgattttt gagggtaggt gctgggttta     120
atgggagga                                                             129

<210> SEQ ID NO 29
<211> LENGTH: 107
<212> TYPE: DNA
<213> ORGANISM: Homo sapiens

<400> SEQUENCE: 29
acggttctgt cctgtagggg agaaaagtcc tcgttgttcc tctgggatgc aacatgagag      60
agcagcacac tgaggcttta tggattgccc tgccacaagt gaacagg                   107

<210> SEQ ID NO 30
<211> LENGTH: 107
<212> TYPE: DNA
<213> ORGANISM: Homo sapiens

<400> SEQUENCE: 30
acggttctgt cctgtagggg agaaaagtcc tcgttgttcc tctgggatgc aacatgagag      60
agcagcacac tgaggcttta tgggttgccc tgccacaagt gaacagg                   107

<210> SEQ ID NO 31
<211> LENGTH: 127
<212> TYPE: DNA
<213> ORGANISM: Homo sapiens

<400> SEQUENCE: 31
gcgcagtcag atgggcgtgc tggcgtctgt cttctctctc tcctgctctc tggcttcatt      60
tttctctcct tctgtctcac cttctttcgt gtgcctgtgc acacacgt ttgggacaag       120 ggctgga                                                               127

<210> SEQ ID NO 32
<211> LENGTH: 127
<212> TYPE: DNA
```

<213> ORGANISM: Homo sapiens

<400> SEQUENCE: 32

| gcgcagtcag atgggcgtgc tggcgtctgt cttctctctc tcctgctctc tggcttcatt | 60 |
| tttctctcct tctgtctcac cttctttcgt gtgcctgtgc atacacacgt ttgggacaag | 120 |
| ggctgga | 127 |

<210> SEQ ID NO 33
<211> LENGTH: 130
<212> TYPE: DNA
<213> ORGANISM: Homo sapiens

<400> SEQUENCE: 33

| gccggacctg cgaaatccca aaatgccaaa cattcccgcc tcacatgatc ccagagagag | 60 |
| gggacccagt gttcccagct tgcagctgag gagcccgagg ttgccgtcag atcagagccc | 120 |
| cagttgcccg | 130 |

<210> SEQ ID NO 34
<211> LENGTH: 130
<212> TYPE: DNA
<213> ORGANISM: Homo sapiens

<400> SEQUENCE: 34

| gccggacctg cgaaatccca aaatgccaaa cattcccgcc tcacatgatc ccagagagag | 60 |
| gggacccagt gttcccagct tgcagctgag gagcccgagt tgccgtcag atcagagccc | 120 |
| cagttgcccg | 130 |

<210> SEQ ID NO 35
<211> LENGTH: 121
<212> TYPE: DNA
<213> ORGANISM: Homo sapiens

<400> SEQUENCE: 35

| agcagcctcc ctcgactagc tcacactacg ataaggaaaa ttcatgagct ggtgtccaag | 60 |
| gagggctggg tgactcgtgg ctcagtcagc atcaagattc ctttcgtctt tcccctctgc | 120 |
| c | 121 |

<210> SEQ ID NO 36
<211> LENGTH: 121
<212> TYPE: DNA
<213> ORGANISM: Homo sapiens

<400> SEQUENCE: 36

| agcagcctcc ctcgactagc tcacactacg ataaggaaaa ttcatgagct ggtgtccaag | 60 |
| gagggctggg tgactcgtgg ctcagtcagc gtcaagattc ctttcgtctt tcccctctgc | 120 |
| c | 121 |

<210> SEQ ID NO 37
<211> LENGTH: 138
<212> TYPE: DNA
<213> ORGANISM: Homo sapiens

<400> SEQUENCE: 37

| tggcattgcc tgtaatatac atagccatgg tttttatag gcaatttaag atgaatagct | 60 |
| tctaaactat agataagttt cattacccca ggaagctgaa ctatagctac tttacccaaa | 120 |
| atcattagaa tggtgctt | 138 |

```
<210> SEQ ID NO 38
<211> LENGTH: 138
<212> TYPE: DNA
<213> ORGANISM: Homo sapiens

<400> SEQUENCE: 38
tggcattgcc tgtaatatac atagccatgg ttttttatag gcaatttaag atgaatagct      60
tctaaactat agataagttt cattacccca ggaagctgaa ctatagctac tttccccaaa     120
atcattagaa tggtgctt                                                   138

<210> SEQ ID NO 39
<211> LENGTH: 136
<212> TYPE: DNA
<213> ORGANISM: Homo sapiens

<400> SEQUENCE: 39
atgaagcctt ccaccaactg cctgtatgac tcatctgggg acttctgctc tatactcaaa      60
gtggcttagt cactgccaat gtatttccat atgagggacg atgattacta aggaaatata     120
gaaacaacaa ctgatc                                                     136

<210> SEQ ID NO 40
<211> LENGTH: 136
<212> TYPE: DNA
<213> ORGANISM: Homo sapiens

<400> SEQUENCE: 40
atgaagcctt ccaccaactg cctgtatgac tcatctgggg acttctgctc tatactcaaa      60
gtggcttagt cactgccaat gtatttccat atgagggacg gtgattacta aggaaatata     120
gaaacaacaa ctgatc                                                     136

<210> SEQ ID NO 41
<211> LENGTH: 118
<212> TYPE: DNA
<213> ORGANISM: Homo sapiens

<400> SEQUENCE: 41
acaacagaat caggtgattg gagaaaagat cacaggccta ggcacccaag gcttgaagga      60
tgaaagaatg aaagatggac ggaacaaaat taggaccttaa attctttgtt cagttcag     118

<210> SEQ ID NO 42
<211> LENGTH: 118
<212> TYPE: DNA
<213> ORGANISM: Homo sapiens

<400> SEQUENCE: 42
acaacagaat caggtgattg gagaaaagat cacaggccta ggcacccaag gcttgaagga      60
tgaaagaatg aaagatggac ggaagaaaat taggacctta attctttgtt cagttcag     118

<210> SEQ ID NO 43
<211> LENGTH: 150
<212> TYPE: DNA
<213> ORGANISM: Homo sapiens

<400> SEQUENCE: 43
ttggggtaaa ttttcattgt catatgtgga atttaaatat accatcatct acaaagaatt      60
ccacagagtt aaatatctta agttaaacac ttaaaataag tgtttgcgtg atattttgat     120
```

```
gacagataaa cagagtctaa ttcccacccc                                            150

<210> SEQ ID NO 44
<211> LENGTH: 150
<212> TYPE: DNA
<213> ORGANISM: Homo sapiens

<400> SEQUENCE: 44
ttggggtaaa ttttcattgt catatgtgga atttaaatat accatcatct acaaagaatt            60
ccacagagtt aaatatctta agttaaacac ttaaaataag tgtttgcgtg atattttgat           120
gatagataaa cagagtctaa ttcccacccc                                            150

<210> SEQ ID NO 45
<211> LENGTH: 145
<212> TYPE: DNA
<213> ORGANISM: Homo sapiens

<400> SEQUENCE: 45
tgcaattcaa atcaggaagt atgaccaaaa gacagagatc ttttttggat gatccctagc            60
ctagcaatgc ctggcagcca tgcaggtgca atgtcaacct taaataatgt attgcaaact           120
cagagctgac aaacctcgat gttgc                                                 145

<210> SEQ ID NO 46
<211> LENGTH: 145
<212> TYPE: DNA
<213> ORGANISM: Homo sapiens

<400> SEQUENCE: 46
tgcaattcaa atcaggaagt atgaccaaaa gacagagatc ttttttggat gatccctagc            60
ctagcaatgc ctggcagcca tgcaggtgca atgtcaacct taaataatgt attgcaaatt           120
cagagctgac aaacctcgat gttgc                                                 145

<210> SEQ ID NO 47
<211> LENGTH: 124
<212> TYPE: DNA
<213> ORGANISM: Homo sapiens

<400> SEQUENCE: 47
ctgtgctctg cgaatagctg cagaagtaac ttggggaccc aaaataaagc agaatgctaa            60
tgtcaagtcc tgagaaccaa gccctgggac tctggtgcca tttcggattc tccatgagca           120
tggt                                                                        124

<210> SEQ ID NO 48
<211> LENGTH: 124
<212> TYPE: DNA
<213> ORGANISM: Homo sapiens

<400> SEQUENCE: 48
ctgtgctctg cgaatagctg cagaagtaac ttggggaccc aaaataaagc agaatgctaa            60
tgtcaagtcc tgagaaccaa gccctgggac tctggtgcca ttttggattc tccatgagca           120
tggt                                                                        124

<210> SEQ ID NO 49
<211> LENGTH: 118
<212> TYPE: DNA
<213> ORGANISM: Homo sapiens

<400> SEQUENCE: 49
```

```
tttttccagc caactcaagg ccaaaaaaaa tttcttaata tagttattat gcgaggggag     60
gggaagcaaa ggagcacagg tagtccacag aataagacac aagaaacctc aagctgtg     118
```

<210> SEQ ID NO 50
<211> LENGTH: 118
<212> TYPE: DNA
<213> ORGANISM: Homo sapiens

<400> SEQUENCE: 50

```
tttttccagc caactcaagg ccaaaaaaaa tttcttaata tagttattat gcgaggggag     60
gggaagcaaa ggagcacagg tagtccacag aataggacac aagaaacctc aagctgtg     118
```

<210> SEQ ID NO 51
<211> LENGTH: 110
<212> TYPE: DNA
<213> ORGANISM: Homo sapiens

<400> SEQUENCE: 51

```
tcttctcgtc ccctaagcaa acaacatccg cttgcttctg tctgtgtaac cacagtgaat     60
gggtgtgcac gcttgatggg cctctgagcc cctgttgcac aaaccagaaa              110
```

<210> SEQ ID NO 52
<211> LENGTH: 110
<212> TYPE: DNA
<213> ORGANISM: Homo sapiens

<400> SEQUENCE: 52

```
tcttctcgtc ccctaagcaa acaacatccg cttgcttctg tctgtgtaac cacagtgaat     60
gggtgtgcac gcttggtggg cctctgagcc cctgttgcac aaaccagaaa              110
```

<210> SEQ ID NO 53
<211> LENGTH: 110
<212> TYPE: DNA
<213> ORGANISM: Homo sapiens

<400> SEQUENCE: 53

```
cacatggggg cattaagaat cgcccaggga ggaggaggga gaacgcgtgc ttttcacatt     60
tgcatttgaa ttttcgagtt cccaggatgt gttttttgtgc tcatcgatgt             110
```

<210> SEQ ID NO 54
<211> LENGTH: 110
<212> TYPE: DNA
<213> ORGANISM: Homo sapiens

<400> SEQUENCE: 54

```
cacatggggg cattaagaat cgcccaggga ggaggaggga gaacgcgtgc ttttcacatt     60
tgcatttgaa tttttgagtt cccaggatgt gttttttgtgc tcatcgatgt             110
```

<210> SEQ ID NO 55
<211> LENGTH: 128
<212> TYPE: DNA
<213> ORGANISM: Homo sapiens

<400> SEQUENCE: 55

```
gggctctgag gtgtgtgaaa taaaaacaaa tgtccatgtc tgtcctttta tggcattttg     60
ggactttaca tttcaaacat ttcagacatg tatcacaaca cgaaggaata acagttccag    120
ggatatct                                                            128
```

<210> SEQ ID NO 56
<211> LENGTH: 128
<212> TYPE: DNA
<213> ORGANISM: Homo sapiens

<400> SEQUENCE: 56
gggctctgag gtgtgtgaaa taaaaacaaa tgtccatgtc tgtccttttta tggcattttg        60 ggactttaca tttcaaacat ttcagacatg tatcacaaca cgagggaata acagttccag       120
ggatatct                                                                128

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cacatgcaca gccagcaacc c                                                   21

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ccccaaggtc ctgtgacctg agt                                                 23

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tgaggaagtg aggctcagag ggt                                                 23

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tgccagtgcg agatgaaagt cttt                                                24

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gtgccttcag aacctttgag atctgat                                             27

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tcccatccca ccagccaccc                                          20

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
aggtgtgtct ctcttttgtg agggg                                    25

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cctttgtccc acctccccac c                                        21

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cctcgcctac tgtgctgttt ctaacc                                   26

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ccatcccagc tgagtattcc aggag                                    25

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
aattgcaatg gtgagaggtt gatggt                                   26

```
<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ccagtgagaa gtgtcttggg ttgg                                              24

<210> SEQ ID NO 69
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gaaatgcctt ctcaggtaat ggaaggt                                           27

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ggtttgagca gttctgagaa tgtggct                                           27

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
acccaaaaca ctggaggggc ct                                                22

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cccttatctg ctatgtggca tacttgg                                           27

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gcaccagaat ttaaacaacg ctgacaa                                           27

<210> SEQ ID NO 74
```

<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
gcacctgaca ggcacatcag cg                                              22

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
tgactgtata ccccaggtgc accc                                            24

<210> SEQ ID NO 76
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
gcactaagga tgtggaagtc tagtgtg                                         27

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
tgtacgtggt caccagggga cg                                              22

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
agtgtgagaa gagcctcaag gacagc                                          26

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
cagtggaccc tgctgcacct t                                               21

<210> SEQ ID NO 80
<211> LENGTH: 24

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gtggcaaagg agagagttgt gagg                                            24

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
cagtggcata gtagtccagg ggct                                            24

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cctctccgac aacttccgcc g                                               21

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
aggtctgggg gccgctgaat                                                 20

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tcctcccatt aaacccagca cct                                             23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
acggttctgt cctgtagggg aga                                             23

<210> SEQ ID NO 86
<211> LENGTH: 22
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 86
cctgttcact tgtggcaggg ca                                              22

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gcgcagtcag atgggcgtgc                                                 20

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88 tccagcccctt gtcccaaacg tgt                                            23

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gccggacctg cgaaatccca a                                               21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
cgggcaactg gggctctgat c                                               21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
agcagcctcc ctcgactagc t                                               21

<210> SEQ ID NO 92
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 92
ggcagagggg aaagacgaaa gga                                            23

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
tggcattgcc tgtaatatac atag                                           24

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
aagcaccatt ctaatgattt tgg                                            23

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
atgaagcctt ccaccaactg                                                20

<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gatcagttgt tgtttctata tttcctt                                        27

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
acaacagaat caggtgattg ga                                             22

<210> SEQ ID NO 98
<211> LENGTH: 25
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 98
ctgaactgaa caaagaatta aggtc                                        25

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ttggggtaaa ttttcattgt ca                                           22

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ggggtgggaa ttagactctg                                              20

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tgcaattcaa atcaggaagt atg                                          23

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gcaacatcga ggtttgtcag                                              20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ctgtgctctg cgaatagctg                                              20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 104
accatgctca tggagaatcc                                              20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 105
tttttccagc caactcaagg                                              20

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 106
cacagcttga ggtttcttgt g                                            21

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 107
tcttctcgtc ccctaagcaa                                              20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 108
tttctggttt gtgcaacagg                                              20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 109
cacatggggg cattaagaat                                              20

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

```
<400> SEQUENCE: 110
acatcgatga gcacaaaaac ac                                          22

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gggctctgag gtgtgtgaaa                                             20

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
agatatccct ggaactgtta ttcc                                        24

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
acagtaactg ccttcataga tag                                         23

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gtgtcagacc ctgttctaag ta                                          22

<210> SEQ ID NO 115
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
aaataaaatt aggcatattt acaagc                                      26

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 116
gctgagtgat tgtctgtaa ttg                                          23

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
cctgttcctc ccttatttcc c                                           21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gggaacacag actccatggt g                                           21

<210> SEQ ID NO 119
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
cttagggaac cctcactgaa tg                                          22

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
gtccttgtca gcgtttattt gc                                          22

<210> SEQ ID NO 121
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
aataatcagt atgtgacttg gattga                                      26

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
```
ataggatgga tggatagatg ga                                            22

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
cagagcaaga ccctgtctca t                                             21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
tcaacagagg cttgcatgta t                                             21

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gggtgatttt cctctttggt                                               20

<210> SEQ ID NO 126
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
aacatttgta tctttatctg tatccttatt tat                                33

<210> SEQ ID NO 127
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gaacacttgt catagtttag aacgaac                                       27

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tcattgacag aattgcacca                                            20

<210> SEQ ID NO 129
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
tttgtatttc atgtgtacat tcgtatc                                    27

<210> SEQ ID NO 130
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
acctatcctg tagattattt tcactgtg                                   28

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
tctgacccat ctaacgccta                                            20

<210> SEQ ID NO 132
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
cagacagaaa gatagataga tgattga                                    27

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
atacagacag acagacaggt g                                          21

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gcatgtatct atcatccatc tct                                        23

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
tgagtgacaa attgagacct t                                              21

<210> SEQ ID NO 136
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gtcttacaat aacagttgct actatt                                         26

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
attccccaag tgaattgc                                                  18

<210> SEQ ID NO 138
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ggtagataga ctggatagat agacga                                         26

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
tggaaacaga aatggcttgg                                                20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gattgcagga gggaaggaag                                                20

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
gagcaagaca ccatctcaag aa                                            22

<210> SEQ ID NO 142
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
gaaattttac atttatgttt atgattctct                                    30

<210> SEQ ID NO 143
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
ggcgactgag caagactc                                                 18

<210> SEQ ID NO 144
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
ggttattaat tgagaaaact ccttaca                                       27

<210> SEQ ID NO 145
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
attttccccg atgatagtag tct                                           23

<210> SEQ ID NO 146
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
gcgaatgtat gattggcaat attttt                                        26

```
<210> SEQ ID NO 147
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
acatgtatcc cagaacttaa agtaaac                                          27

<210> SEQ ID NO 148
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
gcagaaggga aaattgaagc tg                                               22

<210> SEQ ID NO 149
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cagagacacc gaaccaataa ga                                               22

<210> SEQ ID NO 150
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gccacatgaa tcaattccta taataaa                                          27

<210> SEQ ID NO 151
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
gcacatgtac cctaaaactt aaaat                                            25

<210> SEQ ID NO 152
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
gtcaaccaaa actcaacaag tagtaa                                           26

<210> SEQ ID NO 153
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
aagatgaaat tgccatgtaa aaata                                          25

<210> SEQ ID NO 154
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
gtgtgtataa caaaattcct atgatgg                                        27

<210> SEQ ID NO 155
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
gcacccaaaa ctgaatgtca ta                                             22

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
ggtgagagtg agaccctgtc                                                20

<210> SEQ ID NO 157
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
tgtaataact ctacgactgt ctgtctg                                        27

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
gaataggagg tggatggatg g                                              21

<210> SEQ ID NO 159
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
gagcgagacc ctgtctcaag                                              20

<210> SEQ ID NO 160
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
ggaaaagaca taggatagca attt                                         24

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
tctggattga tctgtctgtc c                                            21

<210> SEQ ID NO 162
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
gaattaaata ccatctgagc actgaa                                       26

<210> SEQ ID NO 163
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
tgttataatg cattgagttt tattctg                                      27

<210> SEQ ID NO 164
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gcctgtctca aaaataaaga gatagaca                                     28

<210> SEQ ID NO 165
<211> LENGTH: 25
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 165
ttaatgaatt gaacaaatga gtgag                                          25

<210> SEQ ID NO 166
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
gcaactctgg ttgtattgtc ttcat                                          25

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
caaagcgaga ctctgtctca a                                              21

<210> SEQ ID NO 168
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gaaaatgcta tcctctttgg tataaat                                        27

<210> SEQ ID NO 169
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
gggtatttca agataactgt agatagg                                        27

<210> SEQ ID NO 170
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gcttctgaaa gcttctagtt tacc                                           24

<210> SEQ ID NO 171
<211> LENGTH: 19
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 171
tccacatcct caccaacac                                                    19

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gcctaggaag gctactgtca a                                                 21

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
ccacccgtcc atttaggc                                                     18

<210> SEQ ID NO 174
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
gtgaaaaagt agatataatg gttggtg                                           27

<210> SEQ ID NO 175
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
ggttttccaa gagatagacc aatta                                             25

<210> SEQ ID NO 176
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gtcctctcat aaatccctac tcatatc                                           27

<210> SEQ ID NO 177
<211> LENGTH: 27
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 177
ctgttggtac ataataggta ggtaggt                                           27

<210> SEQ ID NO 178
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
gtcgtgggcc ccataaatc                                                   19

<210> SEQ ID NO 179
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
aaggtacata acagttcaat agaaagc                                           27

<210> SEQ ID NO 180
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
gtgaaatgac tgaaaatag taacca                                             26

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
ctaggagatc atgtgggtat gatt                                              24

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
gcagtgaata aatgaacgaa tgga                                              24

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 183
cccaaaatta cttgagccaa t                                           21

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
gagacaaaat gaagaaacag acag                                        24

<210> SEQ ID NO 185
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
tctttgctct catgaataga tcagt                                       25

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
gtttgtgata atgaacccac tcag                                        24

<210> SEQ ID NO 187
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
tgaacacaga tgttaagtgt gtatatg                                     27

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
gtctgaggtg gacagttatg aaa                                         23

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 189
ctgtggctca tctatgaaaa ctt                                            23

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
gaagtggctg tggtgttatg at                                             22

<210> SEQ ID NO 191
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
ttctgttggt atagagcagt gttt                                           24

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
gtgacaggaa ggacggaatg                                                20

<210> SEQ ID NO 193
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
catgaggttt gcaaatacta tcttaac                                        27

<210> SEQ ID NO 194
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
gttttaattt tctccaaatc tcca                                           24

<210> SEQ ID NO 195
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 195
tcttagccta gatagatact tgcttcc                                          27

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gtcaaccttt gaggctatag gaa                                              23

<210> SEQ ID NO 197
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
tcctggaaac aaaagtatt                                                   19

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
aaccttacaa caaagctaga a                                                21

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
actaagcctt ggggatccag                                                  20

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
tgctgtggaa atactaaaag g                                                21

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
```

```
ctccagaggt aatcctgtga                                              20
```

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202

```
tggtgtgaga tggtatctag g                                            21
```

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203

```
gtataatcca tgaatcttgt tt                                           22
```

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204

```
ttcaaattgt atataagaga gt                                           22
```

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205

```
gcaggaaagt tatttttaat                                              20
```

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206

```
tgcttgagaa agctaacact t                                            21
```

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
cagtgtttgg aaattgtctg                                               20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
ggcactggga gattattgta                                               20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
tcctgttgtt aagtacacat                                               20

<210> SEQ ID NO 210
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
gggccgtaat tacttttg                                                 18

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
actcagtagg cactttgtgt c                                             21

<210> SEQ ID NO 212
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
tcttccacca caccaatc                                                 18

<210> SEQ ID NO 213
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
tggcttttca aaggtaaaa                                                19

```
<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
gcaacgttaa catctgaatt t                                            21

<210> SEQ ID NO 215

<400> SEQUENCE: 215

000

<210> SEQ ID NO 216
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
attttatatg tcatgatcta ag                                           22

<210> SEQ ID NO 217
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
agagattaca ggtgtgagc                                               19

<210> SEQ ID NO 218
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
atgatcctca actgcctct                                               19

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
tgaaactcaa aagagaaaag                                              20

<210> SEQ ID NO 220
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 220
acagatttct acttaaaatt                                              20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
tgaaactcaa aagagaaaag                                              20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
acagatttct acttaaaatt                                              20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
gcaaaggggt actctatgta                                              20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
tatcgggtca tcttgttaaa                                              20

<210> SEQ ID NO 225
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
tctaacaaag ctctgtccaa aa                                           22

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 226
ccacactgaa taactggaac a                                              21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
gcaagcaagc tctctacctt c                                              21

<210> SEQ ID NO 228
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
tgttcttcca aaattcacat gc                                             22

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
atttcactat tccttcattt t                                              21

<210> SEQ ID NO 230
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
taattgttgc acactaaatt ac                                             22

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
aaaaagccac agaaatcagt c                                              21

<210> SEQ ID NO 232
<211> LENGTH: 22
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 232
ttcttatatc tcactgggca tt                                              22

<210> SEQ ID NO 233
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
ggatggtaga agagaagaaa gg                                              22

<210> SEQ ID NO 234
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
ggatggtaga agagaagaaa gg                                              22

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
tgcaaagatg cagaaccaac                                                 20

<210> SEQ ID NO 236
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
ttttgttcct tgtcctggct ga                                              22

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
tgcaaagatg cagaaccaac                                                 20

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 238
gcctccagct ctatccaagt t                                              21

<210> SEQ ID NO 239
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
ccttaatatc ttcccatgtc ca                                             22

<210> SEQ ID NO 240
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
attgttagtg cctcttctgc tt                                             22

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
gagaagtgag gtcagcagct                                                20

<210> SEQ ID NO 242
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
tttctaaatt tccattgaac ag                                             22

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
gaaattggca atctgattct                                                20

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
```
caacttgtcc tttattgatg t       21

<210> SEQ ID NO 245
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
ctatgttgat aaaacattga aa       22

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
gcctgtctgg aatatagttt       20

<210> SEQ ID NO 247
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
cagggcatat aatctaagct gt       22

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
caatgactct gagttgagca c       21

<210> SEQ ID NO 249
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
actctctccc tcccctct       18

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250

-continued tatggcccca aaactattct                                              20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
acaagtactg ggcagattga                                              20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
gccaggttta gctttcaagt                                              20

<210> SEQ ID NO 253
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
ttttatatca ggagaaacac tg                                           22

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
ccagaatttt ggaggtttaa t                                            21

<210> SEQ ID NO 255
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
tgtcattcct cctttatctc ca                                           22

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
ttcttttgcc tctcccaaag                                              20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
accctggcac agtgttgact                                                    20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
tgggcctgag ttgagaagat                                                    20

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
aatttgtaag tatgtgcaac g                                                  21

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
tttttcccat ttccaactct                                                    20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
aaaagatgag acaggcaggt                                                    20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
acccctgtga atctcaaaat                                                    20

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
gcacttgctt ctattgtttg t                                               21

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
cccttcctct cttccattct                                                 20

<210> SEQ ID NO 265
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
agcactgcag gta                                                        13

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
acagatacca aagaactgca a                                               21

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
tggacaccct tcaacttaga                                                 20

<210> SEQ ID NO 268
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
gaacagtaat gttgaacttt tt                                              22

```
<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
tcttgcaaaa agcttagcac a                                              21

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
aaaaagatct caaagggtcc a                                              21

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
gcttttgctg aacatcaagt                                                20

<210> SEQ ID NO 272
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
ccttccagca gcatagtct                                                 19

<210> SEQ ID NO 273
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
aaatccagga tgtgcagt                                                  18

<210> SEQ ID NO 274
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
atgatgaggt cagtggtgt                                                 19

<210> SEQ ID NO 275
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
catcacagat catagtaaat gg                                              22

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
aattattatt ttgcaggcaa t                                               21

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
catgaggcaa acacctttcc                                                 20

<210> SEQ ID NO 278
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
gctggactca ggataaagaa ca                                              22

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
tggaagcctg agctgactaa                                                 20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280 ccttctttc ccccagaatc                                                  20

<210> SEQ ID NO 281
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
taggagaaca gaagatcaga g                                              21

<210> SEQ ID NO 282
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
aaagactatt gctaaatgct tg                                             22

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
taagcgtagg gctgtgtgtg                                                20

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
ggacggatag actccagaag g                                              21

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
gaatgacctt ggcactttta tca                                            23

<210> SEQ ID NO 286
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
aaggatagag atatacagat gaatgga                                        27

<210> SEQ ID NO 287
<211> LENGTH: 18
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 287
catgcaccgc gcaaatac                                                 18

<210> SEQ ID NO 288
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
atgcctcacc cacaaacac                                                19

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
tccaagccct tctcactcac                                               20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
ctgggacggt gacattttct                                               20

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
cccaggaaga gtggaaagat t                                             21

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
ttagcttgca tgtacctgtg t                                             21

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
agctagatgg ggtgaatttt                                               20

<210> SEQ ID NO 294
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
tgggctgagg ggagattc                                                 18

<210> SEQ ID NO 295
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
atcaagctaa ttaatgttat ct                                            22

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
aatgaataag gtcctcagag                                               20

<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
tttaatctga tcattgccct a                                             21

<210> SEQ ID NO 298
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
agctgtgggt gaccttga                                                 18

<210> SEQ ID NO 299
<211> LENGTH: 20
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 299
tgtcccacca ttgtgtatta                                              20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
tcagacttga agtccaggat                                              20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
gcttcagggg tgttagtttt                                              20

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
ctttgtgaaa agtcgtccag                                              20

<210> SEQ ID NO 303
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
ccatcatgga aagcatgg                                                18

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
tcatctccat gactgcacta                                              20

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 305
gagatgacgg agtagctcat                                              20

<210> SEQ ID NO 306
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
cccagctgca ctgtctac                                                18

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
tcttgttcca atcacaggac                                              20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
atgctgttag ctgaagctct                                              20

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
tgaaagctcc taaagcagag                                              20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
ttgaagagat gtgctatcat                                              20

<210> SEQ ID NO 311
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
gccgcctgca gcccgcgccc cccgtgcccc cgccccgccg ccggcccggg cgcc    54

<210> SEQ ID NO 312
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
gttcggcttt caccagtct    19

<210> SEQ ID NO 313
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
ctccatagct ctccccact    19

<210> SEQ ID NO 314
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 314
cgccctgcca tgtggaa    17

<210> SEQ ID NO 315
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
cgcttaacat agcagaagca    20

<210> SEQ ID NO 316
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
agtttcgaac tctggcacct    20

<210> SEQ ID NO 317
<211> LENGTH: 25
<212> TYPE: DNA
<213> ORGANISM: Artificial Sequence
<220> FEATURE:

-continued

```
<223> OTHER INFORMATION: Description of Artificial Sequence: Synthetic
      probe

<400> SEQUENCE: 317
tgtcgcactc tccttgtttt tgaca                                              25
```